US010646481B2

(12) United States Patent
Rowe et al.

(10) Patent No.: US 10,646,481 B2
(45) Date of Patent: May 12, 2020

(54) PHARMACEUTICAL COMPOSITION AND ADMINISTRATIONS THEREOF

(71) Applicant: Vertex Pharmaceuticals Incorporated, Boston, MA (US)

(72) Inventors: William Rowe, Medford, MA (US); Patricia Hurter, Harvard, MA (US); Christopher Young, Waltham, MA (US); Kirk Dinehart, Holliston, MA (US); Marinus Jacobus Verwijs, Framingham, MA (US); Kirk Overhoff, Waltham, MA (US); Peter D. J. Grootenhuis, San Diego, CA (US); Martyn Botfield, Concord, MA (US); Alfredo Grossi, Somerville, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/253,636

(22) Filed: Aug. 31, 2016

(65) Prior Publication Data

US 2017/0087144 A1  Mar. 30, 2017

Related U.S. Application Data

(63) Continuation of application No. 14/135,323, filed on Dec. 19, 2013, now abandoned, which is a continuation of application No. 12/583,066, filed on Aug. 13, 2009, now abandoned.

(60) Provisional application No. 61/088,704, filed on Aug. 13, 2008, provisional application No. 61/088,801, filed on Aug. 14, 2008, provisional application No. 61/090,096, filed on Aug. 19, 2008, provisional application No. 61/146,163, filed on Jan. 21, 2009, provisional application No. 61/181,527, filed on May 27, 2009, provisional application No. 61/183,345, filed on Jun. 2, 2009.

(51) Int. Cl.
*A61K 31/47* (2006.01)
*A61K 9/28* (2006.01)
*A61K 9/00* (2006.01)
*A61K 9/16* (2006.01)
*A61K 31/44* (2006.01)
*A61K 9/20* (2006.01)

(52) U.S. Cl.
CPC .......... *A61K 31/47* (2013.01); *A61K 9/0053* (2013.01); *A61K 9/1635* (2013.01); *A61K 9/1652* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/28* (2013.01); *A61K 9/282* (2013.01); *A61K 9/284* (2013.01); *A61K 31/44* (2013.01)

(58) Field of Classification Search
None
See application file for complete search history.

(56) References Cited

U.S. PATENT DOCUMENTS

| | | |
|---|---|---|
| 3,443,940 A | 5/1969 | Bloom et al. |
| 3,524,858 A | 8/1970 | Kaminsky et al. |
| 3,698,292 A | 10/1972 | Koester |
| 3,812,094 A | 5/1974 | MacLeay et al. |
| 3,931,145 A | 1/1976 | Stanley et al. |
| 3,992,540 A | 11/1976 | Clemence et al. |
| 4,107,310 A | 8/1978 | Allais et al. |
| 4,110,355 A | 8/1978 | Bloom et al. |
| 4,221,779 A | 9/1980 | Graham |
| 4,284,629 A | 8/1981 | Grohe et al. |
| 4,312,870 A | 1/1982 | Yokoyama |
| 4,450,166 A | 5/1984 | Clemence et al. |
| 4,450,167 A | 5/1984 | Le Martret et al. |
| 4,638,067 A | 1/1987 | Culbertson et al. |
| 4,777,252 A | 10/1988 | Slusarchyk et al. |
| 4,786,644 A | 11/1988 | Glamkowski et al. |
| 4,845,105 A | 7/1989 | Clemence et al. |
| 4,908,366 A | 3/1990 | Schriewer et al. |
| 4,956,465 A | 9/1990 | Schriewer et al. |
| 5,026,711 A | 6/1991 | Mendes et al. |
| 5,175,151 A | 12/1992 | Afonso et al. |
| 5,180,400 A | 1/1993 | Baudry et al. |
| 5,254,135 A | 10/1993 | Lang et al. |
| 5,281,612 A | 1/1994 | Domagala et al. |

(Continued)

FOREIGN PATENT DOCUMENTS

| | | |
|---|---|---|
| CA | 1025856 A1 | 2/1978 |
| CA | 2065106 A1 | 10/1992 |

(Continued)

OTHER PUBLICATIONS

Accurso, F. J. et al. (2009) "Final results of a 14- and 28-day study of VX-770 in subjects with CF" *J. Cystic Fibrosis*, vol. 8, Supplement 2, Abstracts of the 32nd European Cystic Fibrosis Conference, Jun. 10-13, 2009, Abstract 97, p. S25.

(Continued)

*Primary Examiner* — Erin E Hirt
(74) *Attorney, Agent, or Firm* — Finnegan, Henderson, Farabow, Garrett & Dunner, LLP

(57) ABSTRACT

The present invention relates to pharmaceutical compositions comprising a solid dispersion of N-[2,4-Bis(1,1-dimethylethyl)-5-hydroxyphenyl]-1,4-dihydro-4-oxoquinoline-3-carboxamide, methods of manufacturing pharmaceutical compositions of the present invention, and methods of administering pharmaceutical compositions of the present invention.

26 Claims, 1 Drawing Sheet

(56) References Cited

U.S. PATENT DOCUMENTS

| | | |
|---|---|---|
| 5,322,847 A | 6/1994 | Marfat et al. |
| 5,352,690 A | 10/1994 | Sofia |
| 5,364,414 A | 11/1994 | Lang et al. |
| 5,378,694 A | 1/1995 | Afonso et al. |
| 5,380,713 A | 1/1995 | Balasubramanian et al. |
| 5,409,503 A | 4/1995 | Clausen et al. |
| 5,412,104 A | 5/1995 | Afonso et al. |
| 5,491,139 A | 2/1996 | Demuth, Jr. et al. |
| 5,527,763 A | 6/1996 | Miyazaki et al. |
| 5,536,727 A | 7/1996 | Witzel et al. |
| 5,573,868 A | 11/1996 | Umemoto et al. |
| 5,610,162 A | 3/1997 | Witzel et al. |
| 5,663,179 A | 9/1997 | Dumaitre et al. |
| 5,708,000 A | 1/1998 | Charvet-Faury et al. |
| 5,728,691 A | 3/1998 | Corpi Constantino |
| 5,744,471 A | 4/1998 | Bare et al. |
| 5,750,754 A | 5/1998 | Mills |
| 5,753,666 A | 5/1998 | Beasley et al. |
| 5,804,588 A | 9/1998 | Dyke et al. |
| 5,807,869 A | 9/1998 | Furuya et al. |
| 5,811,553 A | 9/1998 | Farina et al. |
| 5,834,485 A | 11/1998 | Dyke et al. |
| 5,840,745 A | 11/1998 | Buzzetti et al. |
| 5,874,424 A | 2/1999 | Batchelor et al. |
| 5,891,878 A | 4/1999 | Beasley et al. |
| 5,892,114 A | 4/1999 | Goldmann et al. |
| 5,938,792 A | 8/1999 | Lang et al. |
| 5,948,814 A | 9/1999 | Hwang et al. |
| 6,039,974 A * | 3/2000 | MacLaren ............ A61K 31/445 424/472 |
| 6,069,151 A | 5/2000 | Dyke et al. |
| 6,133,265 A | 10/2000 | Blum et al. |
| 6,194,454 B1 | 2/2001 | Dow |
| 6,215,016 B1 | 4/2001 | Kawai et al. |
| 6,218,393 B1 | 4/2001 | Ryder et al. |
| 6,258,822 B1 | 7/2001 | Geyer et al. |
| 6,316,617 B1 | 11/2001 | Blum et al. |
| 6,362,340 B1 | 3/2002 | Dang |
| 6,395,750 B1 | 5/2002 | Hedlund et al. |
| 6,413,956 B1 | 7/2002 | Albaugh et al. |
| 6,429,207 B1 | 8/2002 | Van Wagenen et al. |
| 6,444,617 B1 | 9/2002 | Takaishi et al. |
| 6,448,254 B1 | 9/2002 | Lubisch et al. |
| 6,515,001 B2 | 2/2003 | Saxena et al. |
| 6,544,987 B2 | 4/2003 | Guo et al. |
| 6,720,344 B2 | 4/2004 | Kerwin et al. |
| 6,723,850 B1 | 4/2004 | Guarna et al. |
| 6,790,858 B2 | 9/2004 | Strehlke et al. |
| 6,849,648 B2 | 2/2005 | Bunker et al. |
| 6,878,713 B2 | 4/2005 | De Souza et al. |
| 6,930,131 B2 | 8/2005 | Sabatucci et al. |
| 6,974,806 B2 | 12/2005 | Terashita et al. |
| 6,977,001 B2 | 12/2005 | Sauter et al. |
| 7,001,770 B1 | 2/2006 | Atencio et al. |
| 7,037,913 B2 | 5/2006 | Wang et al. |
| 7,084,156 B2 | 8/2006 | DeVita et al. |
| 7,105,535 B2 | 9/2006 | Berta et al. |
| 7,112,594 B2 | 9/2006 | Ushio et al. |
| 7,179,839 B2 | 2/2007 | Strobel et al. |
| 7,223,759 B2 | 5/2007 | Zhou et al. |
| 7,407,976 B2 | 8/2008 | Miller et al. |
| 7,495,103 B2 | 2/2009 | Hadida Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,939,558 B2 | 5/2011 | Verkman et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,518,441 B2 | 8/2013 | Higuchi et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |

(56) References Cited

U.S. PATENT DOCUMENTS

| | | |
|---|---|---|
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |
| 9,732,080 B2 | 8/2017 | Hadida-Ruah et al. |
| 9,751,839 B2 | 9/2017 | Demattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,840,499 B2 | 12/2017 | Keshavarz-Shokri et al. |
| 9,931,334 B2 | 4/2018 | Hurter et al. |
| 9,974,781 B2 | 5/2018 | Hadida Ruah et al. |
| 10,022,352 B2 | 7/2018 | Hadida Ruah et al. |
| 10,058,546 B2 | 8/2018 | Alargova et al. |
| 10,071,979 B2 | 9/2018 | Tanoury et al. |
| 10,076,513 B2 | 9/2018 | Verwijs et al. |
| 10,081,621 B2 | 9/2018 | Keshavarz-Shokri et al. |
| 10,206,877 B2 | 2/2019 | Phenix et al. |
| 10,239,867 B2 | 3/2019 | Hadida Ruah et al. |
| 2002/0173520 A1 | 11/2002 | Bjork et al. |
| 2003/0100501 A1 | 5/2003 | Davis et al. |
| 2003/0195191 A1 | 10/2003 | Burton et al. |
| 2003/0195201 A1 | 10/2003 | Bo et al. |
| 2004/0033959 A1 | 2/2004 | Chen et al. |
| 2004/0043983 A1 | 3/2004 | Li |
| 2004/0082798 A1 | 4/2004 | Alonso-Alija et al. |
| 2004/0121005 A1 | 6/2004 | Altreuter et al. |
| 2005/0059035 A1 | 3/2005 | Huang et al. |
| 2005/0113423 A1 | 5/2005 | VanGooor et al. |
| 2005/0147669 A1* | 7/2005 | Lawrence ............ A61K 9/2077 424/464 |
| 2005/0176741 A1 | 8/2005 | Okano et al. |
| 2005/0181041 A1 | 8/2005 | Goldman |
| 2005/0186261 A1 | 8/2005 | Avelar et al. |
| 2005/0187300 A1 | 8/2005 | Bajji et al. |
| 2005/0192315 A1 | 9/2005 | Jansson et al. |
| 2005/0208095 A1 | 9/2005 | Hunter et al. |
| 2005/0222199 A1 | 10/2005 | Hayman et al. |
| 2006/0003005 A1 | 1/2006 | Cao et al. |
| 2006/0148806 A1 | 7/2006 | Watanuki et al. |
| 2006/0178516 A1 | 8/2006 | Johnstone et al. |
| 2008/0317853 A1 | 12/2008 | Kashid et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2009/0274756 A1 | 11/2009 | Ukai et al. |
| 2009/0285887 A1 | 11/2009 | Abu-Baker et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0168094 A1 | 7/2010 | Binch et al. |
| 2010/0168158 A1 | 7/2010 | Binch et al. |
| 2010/0256184 A1 | 10/2010 | Rowe et al. |
| 2011/0008259 A1 | 1/2011 | Binch et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Doukou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0094499 A1 | 4/2014 | Alargova et al. |
| 2014/0112988 A1 | 4/2014 | Rowe et al. |
| 2014/0142138 A1 | 5/2014 | Van Goor et al. |
| 2014/0142312 A1 | 5/2014 | Luisi et al. |
| 2014/0155431 A1 | 6/2014 | Hadida-Ruah et al. |
| 2014/0155626 A1 | 6/2014 | Hadida Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0255483 A1 | 9/2014 | Dokou et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |

(56) References Cited

U.S. PATENT DOCUMENTS

| | | | |
|---|---|---|---|
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0141459 A1 | 5/2015 | Van Goor et al. |
| 2015/0150879 A2 | 6/2015 | Van Goor et al. |
| 2015/0164881 A1 | 6/2015 | Van Goor et al. |
| 2015/0164883 A1 | 6/2015 | Van Goor et al. |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0218122 A1 | 8/2015 | Tanoury et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2015/0336956 A1 | 11/2015 | Hadida-Ruah et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0095858 A1 | 4/2016 | Miller et al. |
| 2016/0096807 A1 | 4/2016 | Strohmeier et al. |
| 2016/0143898 A1 | 5/2016 | Hadida Ruah et al. |
| 2016/0166540 A1 | 6/2016 | Looker et al. |
| 2016/0200712 A1 | 6/2016 | Siesel |
| 2016/0221952 A1 | 8/2016 | Yang et al. |
| 2016/0221995 A1 | 8/2016 | Keshavarz-Shokri et al. |
| 2016/0228414 A1 | 8/2016 | Hadida Ruah et al. |
| 2016/0229806 A1 | 8/2016 | Hurter et al. |
| 2016/0237079 A1 | 8/2016 | Hadida Ruah et al. |
| 2016/0271105 A1 | 9/2016 | Hadida Ruah et al. |
| 2016/0303096 A1 | 10/2016 | Verwijs et al. |
| 2016/0318931 A1 | 11/2016 | Hadida-Ruah et al. |
| 2016/0324788 A1 | 11/2016 | Hadida Ruah et al. |
| 2016/0324846 A1 | 11/2016 | Verwijs et al. |
| 2016/0332997 A1 | 11/2016 | Hadida Ruah et al. |
| 2016/0354316 A1 | 12/2016 | Swinney et al. |
| 2017/0096396 A1 | 4/2017 | DeMattei et al. |
| 2017/0100340 A1 | 4/2017 | Dokou et al. |
| 2017/0107205 A1 | 4/2017 | Hadida Ruah et al. |
| 2017/0107206 A1 | 4/2017 | Hadida Ruah et al. |
| 2017/0107225 A1 | 4/2017 | Hadida Ruah et al. |
| 2017/0266176 A1 | 9/2017 | Alargova et al. |
| 2018/0008546 A1 | 1/2018 | Verwijs et al. |
| 2018/0127398 A1 | 5/2018 | Keshavarz-Shokri et al. |
| 2018/0153874 A1 | 6/2018 | Van Goor et al. |
| 2019/0038615 A1 | 2/2019 | Van Goor et al. |
| 2019/0070162 A1 | 3/2019 | Hurter et al. |
| 2019/0076419 A1 | 3/2019 | Hadida Ruah et al. |
| 2019/0125674 A1 | 5/2019 | Phenix et al. |
| 2019/0144450 A1 | 5/2019 | Hadida Ruah et al. |

FOREIGN PATENT DOCUMENTS

| | | |
|---|---|---|
| CA | 2571949 A | 1/2006 |
| CA | 2769695 A1 | 2/2011 |
| CN | 1473827 A | 2/2004 |
| CN | 101006076 A | 7/2007 |
| CN | 101287732 A | 10/2008 |
| CN | 101374849 A | 2/2009 |
| CN | 101384172 A | 3/2009 |
| CN | 101460489 A | 6/2009 |
| CN | 105884628 A | 8/2016 |
| DE | 2050966 A1 | 4/1971 |
| DE | 2407744 A1 | 8/1974 |
| DE | 2415763 A1 | 10/1974 |
| DE | 3827253 A1 | 3/1989 |
| DE | 279887 A1 | 6/1990 |
| DE | 3903799 A1 | 8/1990 |
| DE | 4017516 A1 | 12/1991 |
| DE | 19601142 A1 | 1/1997 |
| DE | 19532235 A1 | 3/1997 |
| EA | 003945 B1 | 10/2003 |
| EA | 004043 B1 | 12/2003 |
| EP | 0004279 B1 | 12/1982 |
| EP | 0308702 A2 | 3/1989 |
| EP | 0332033 A2 | 9/1989 |
| EP | 0332930 A2 | 9/1989 |
| EP | 0343398 A2 | 11/1989 |
| EP | 0382034 A1 | 1/1990 |
| EP | 0363585 A1 | 4/1990 |
| EP | 0409025 A2 | 1/1991 |
| EP | 0425345 A1 | 5/1991 |
| EP | 0460996 A1 | 12/1991 |
| EP | 0472091 B1 | 11/1994 |
| EP | 0705835 A1 | 4/1996 |
| EP | 1227084131 | 12/2005 |
| EP | 1224172 B1 | 4/2007 |
| EP | 0901786 B1 | 6/2007 |
| EP | 3034497 A1 | 6/2016 |
| FR | 960299 A | 4/1950 |
| FR | 2002888 A1 | 10/1969 |
| FR | 2324304 A2 | 4/1977 |
| FR | 2340092 A2 | 9/1977 |
| FR | 2537140 A1 | 6/1984 |
| GB | 1433774 A | 4/1976 |
| GB | 2372986 A | 9/2002 |
| IN | 5333/CHE/2015 | 7/2016 |
| JP | 50-24296 A | 3/1975 |
| JP | 50-29574 A | 3/1975 |
| JP | 55-81878 A | 6/1980 |
| JP | 56-110612 A | 9/1981 |
| JP | 58-18361 A | 2/1983 |
| JP | 1-287066 A | 11/1989 |
| JP | 2-138260 A | 5/1990 |
| JP | 3-34977 A | 2/1991 |
| JP | 3-193725 A | 8/1991 |
| JP | 6-72979 A | 3/1994 |
| JP | 6-509061 A | 10/1994 |
| JP | 7-33729 A | 2/1995 |
| JP | 7-82498 A | 3/1995 |
| JP | 7-179407 A | 7/1995 |
| JP | 8-301849 A | 11/1996 |
| JP | 9-71534 A | 3/1997 |
| JP | 11-116502 A | 4/1999 |
| JP | 11-513021 A | 9/1999 |
| JP | 2000-16982 A | 1/2000 |
| JP | 2000-505450 A | 5/2000 |
| JP | 2000-256358 A | 9/2000 |
| JP | 2001-502683 A | 2/2001 |
| JP | 2001-199965 A | 7/2001 |
| JP | 2001-233859 A | 8/2001 |
| JP | 2002-212179 A | 7/2002 |
| JP | 2002-322054 A | 11/2002 |
| JP | 2002-322154 A | 11/2002 |
| JP | 2002-326935 A | 11/2002 |
| JP | 2003-12667 A | 1/2003 |
| JP | 2003-238413 A | 8/2003 |
| JP | 2004-189738 A | 7/2004 |
| JP | 2004-532209 A | 10/2004 |
| JP | 2005-533770 A | 11/2005 |
| JP | 2006-206612 A | 8/2006 |
| JP | 2008-504291 A | 2/2008 |
| JP | 2009-522278 A | 6/2009 |
| JP | 2012-107069 A | 6/2012 |
| JP | 4947658 B2 | 6/2012 |
| JP | 2013-173750 A | 9/2013 |
| MX | a/2013/002353 | 9/2013 |
| RU | 2047614 C1 | 11/1995 |
| RU | 2155754 C2 | 9/2000 |
| RU | 2270186 C2 | 2/2006 |
| RU | 2389495 C2 | 10/2008 |
| SU | 1360584 A3 | 12/1987 |

(56) References Cited

FOREIGN PATENT DOCUMENTS

| | | |
|---|---|---|
| SU | 1779243 A3 | 11/1992 |
| SU | 1796623 A1 | 2/1993 |
| WO | WO 1991/05783 A1 | 5/1991 |
| WO | WO 1992/14714 A1 | 9/1992 |
| WO | WO 1992/18093 A1 | 10/1992 |
| WO | WO 1992/18483 A1 | 10/1992 |
| WO | WO 1994/14797 A1 | 7/1994 |
| WO | WO 1995/11244 A1 | 4/1995 |
| WO | WO 1995/32948 A1 | 12/1995 |
| WO | WO 1996/15099 A1 | 5/1996 |
| WO | WO 1996/19239 A1 | 6/1996 |
| WO | WO 1997/04779 A1 | 2/1997 |
| WO | WO 1997/23462 A1 | 7/1997 |
| WO | WO 1997/30999 A1 | 8/1997 |
| WO | WO 1998/17648 A1 | 4/1998 |
| WO | WO 1998/026127 A1 | 6/1998 |
| WO | WO 1998/031226 A1 | 7/1998 |
| WO | WO 1999/05096 A2 | 2/1999 |
| WO | WO 1999/32436 A1 | 7/1999 |
| WO | WO 1999/46237 A1 | 9/1999 |
| WO | WO 1999/46267 A1 | 9/1999 |
| WO | WO 2000/40561 A1 | 7/2000 |
| WO | WO 2000/68202 A1 | 11/2000 |
| WO | WO 2001/21159 A2 | 3/2001 |
| WO | WO 2001/30757 A1 | 5/2001 |
| WO | WO 2001/34570 A1 | 5/2001 |
| WO | WO 2001/40217 A1 | 6/2001 |
| WO | WO 2001/47924 A1 | 7/2001 |
| WO | WO 2001/87806 A2 | 11/2001 |
| WO | WO 2002/003938 A1 | 1/2002 |
| WO | WO 2002/038126 A2 | 5/2002 |
| WO | WO 2002/078693 A2 | 10/2002 |
| WO | WO 2002/094809 A1 | 11/2002 |
| WO | WO 2003/043992 A1 | 5/2003 |
| WO | WO 2003/063821 A2 | 8/2003 |
| WO | WO 2003/101454 A1 | 12/2003 |
| WO | WO 2004/039783 A1 | 5/2004 |
| WO | WO 2004/048314 A1 | 6/2004 |
| WO | WO 2004/105779 A2 | 12/2004 |
| WO | WO 2005/035514 A2 | 4/2005 |
| WO | WO 2005/046696 A1 | 5/2005 |
| WO | WO 2005/049018 A1 | 6/2005 |
| WO | WO 2005/075435 A1 | 8/2005 |
| WO | WO 2005/094805 A1 | 10/2005 |
| WO | WO 2005/120497 A2 | 12/2005 |
| WO | WO 2006/002421 A2 | 1/2006 |
| WO | WO 2006/034420 A2 | 3/2006 |
| WO | WO 2006/101740 A2 | 9/2006 |
| WO | WO 2006/127588 A2 | 11/2006 |
| WO | WO 2007/021982 A2 | 2/2007 |
| WO | WO 2007/056341 A1 | 5/2007 |
| WO | WO 2007/067559 A2 | 6/2007 |
| WO | WO 2007/075901 A2 | 7/2007 |
| WO | WO 2007/075946 A1 | 7/2007 |
| WO | WO 2007/079139 A2 | 7/2007 |
| WO | WO-2007079139 A2 * | 7/2007 ........... C07D 215/56 |
| WO | WO 2007/087066 A2 | 8/2007 |
| WO | WO 2007/106537 A2 | 9/2007 |
| WO | WO 2007/106960 A1 | 9/2007 |
| WO | WO 2007/117715 A2 | 10/2007 |
| WO | WO 2007/124318 A1 | 11/2007 |
| WO | WO 2007/134279 A2 | 11/2007 |
| WO | WO 2008/083130 A2 | 7/2008 |
| WO | WO 2008/127399 A2 | 10/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/073757 A1 | 6/2009 |
| WO | WO 2009/076141 A2 | 6/2009 |
| WO | WO 2009/076593 A1 | 6/2009 |
| WO | WO 2010/019239 A2 | 2/2010 |
| WO | WO 2010/025126 A1 | 3/2010 |
| WO | WO 2010/037066 A2 | 4/2010 |
| WO | WO 2010/048526 A2 | 4/2010 |
| WO | WO 2010/048564 A1 | 4/2010 |
| WO | WO 2010/048573 A1 | 4/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/133951 A1 | 10/2011 |
| WO | WO 2011/133953 A1 | 10/2011 |
| WO | WO 2011/146901 A1 | 11/2011 |
| WO | WO 2011/163614 A2 | 12/2011 |
| WO | WO 2012/027247 A2 | 3/2012 |
| WO | WO 2012/027731 A2 | 3/2012 |
| WO | WO 2013/067410 A1 | 5/2013 |
| WO | WO 2013/185112 A1 | 12/2013 |
| WO | WO 2014/014841 A1 | 1/2014 |
| WO | WO 2016/086103 A1 | 6/2016 |
| WO | WO 2016/086136 A1 | 6/2016 |
| WO | WO 2016/087665 A2 | 6/2016 |
| WO | WO 2016/092561 A2 | 6/2016 |
| WO | WO 2016/160945 A1 | 10/2016 |
| WO | WO 2016/180784 A1 | 11/2016 |
| WO | WO 2016/181414 A1 | 11/2016 |
| WO | WO 2016/185423 A1 | 11/2016 |
| WO | WO 2016/199085 A1 | 12/2016 |

OTHER PUBLICATIONS

American College of Chest Physicians (2004) *Living Well With COPD: Chronic Bronchitis and Emphysema. Patient Education Guide.* Northbrook, IL, USA; Product Code: 5032, 44 pages.

Archimica (Oct. 2006) *Coupling Agent ®T3P—The Water Scavenger. High-Performance Amide/Peptide Bond Formations, Dehydrations and Condensations.* [online] Retrieved Apr. 11, 2011, from the Internet: http://www.archimica.com/PDF/ARCHIMICA_T3P_Brochure.pdf> (20 pages).

Ashizawa, K. (2002) *Polymorphism and Crystallization of the Pharmaceutical Drugs,* pp. 273, 278, 305-317 (Japanese).

Aulton, M.E. (Ed.) (2002) *Pharmaceutics: The Science of Dosage Design.* 2nd Ed. Churchill Livingston; pp. 304-321.

Berge, S.M. et al. (1977) "Pharmaceutical Salts" *J Pharmac Sci,* 66(1):1-19.

Bernstein, J. et al. (1995) "Patterns in Hydrogen Bonding: Functionality and Graph Set Analysis in Crystals" *Angew Chem Int Ed Engl,* 34:1555-1573.

Bombeiri, C. et al. (1998) "Complete mutational screening of the CFTR gene in 120 patients with pulmonary disease" *Human Genet,* 103:718-722.

Brittain, H. (Jul. 2001) "X-ray Diffraction III: Pharmaceutical Applications of X-ray Powder Diffraction" *Spectroscopy,* 16(7):14-18.

Brittain, H.G. (Apr. 1997) "Spectral Methods for the Characterization of Polymorphs and Solvates" *J Pharm Sci,* 86(4):405-412.

Brown, R.K. et al. (1954) "6-Aminoindole" *J Am. Chem Soc,* 76(20):5149-5150.

Brown, R.K. et al. (1955) "Derivatives of Indole, 6-Amino-3-indoleacetic Acid" *J Am Chem Soc,* 77(14):3839-3842.

Brown, R.K. et al. (1956) "Some Indole Derivatives Tested for Antitubercular Activity" *J Org Chem,* 21:261-262.

Burvall, K.M. et al. (2002) "The tyrosine kinase inhibitor genistein increases basal cAMP and potentiates forskolin-induced cAMP accumulation in A549 human airway epithelial cells" *Mol Cell Biol,* 240:131-133.

Byrn, S. et al. (1995) "Pharmaceutical Solids: A Strategic Approach to Regulatory Considerations" *Pharmaceutical Research,* 12(7):945-954.

Cai, Z-W. et al. (2011) "Targeting F508del-CFTR to develop rational new therapies for cystic fibrosis" *Acta Pharmacologica Sinica,* 32(6):693-701.

Caira, M.R. (Jan. 1, 1998) "Crystalline Polymorphism of Organic Compounds" *Topics in Chemistry,* 198:163-208.

(56) References Cited

OTHER PUBLICATIONS

Carta, A. et al. (2003) "Synthesis and Biological Evaluation of Triazolo[4,5-g]Quinolines, Imidazo[4,5-g]Quinolines and Pyriodo[2,3-g]Quinoxalines. Part II" *Heterocycles*, 60(4):833-842.
Chemical Abstracts Service, 'Registry' File, RN 174311-74-1. STN Database [online]. Entry Date: Mar. 19, 1996, retrieved on Apr. 25, 2013.
Chemical Abstracts Service, 'Registry' File, RN 325779-54-2. STN Database [online]. Entry Date: Mar. 6, 2001, retrieved on Jan. 28, 2016.
Chemical Abstracts Service, 'Registry' File, RN 329691-97-6. STN Database [online]. Entry Date: Apr. 2, 2001, retrieved on Jan. 28, 2016.
Chemical Abstracts Service, 'Registry' File, RN 329691-99-8. STN Database [online]. Entry Date: Apr. 2, 2001, retrieved on Jan. 28, 2016.
Chemical Abstracts Service, 'Registry' File, RN 329692-01-5. STN Database [online]. Entry Date: Apr. 2, 2001, retrieved on Jan. 28, 2016.
Chemical Abstracts Service, 'Registry' File, RN 329692-03-7. STN Database [online]. Entry Date: Apr. 2, 2001, retrieved on Jan. 28, 2016.
Chemical Abstracts Service, 'Registry' File, RN 329692-05-9. STN Database [online]. Entry Date: Apr. 2, 2001, retrieved on Jan. 28, 2016.
Chemical Abstracts Service, 'Registry' File, RN 329692-14-0. STN Database [online]. Entry Date: Apr. 2, 2001, retrieved on Jan. 28, 2016.
Chemical Abstracts Service, 'Registry' File, RN 625115-91-5. STN Database [online]. Entry Date: Dec. 9, 2003, retrieved on Apr. 25, 2013.
Chemical Abstracts Service, 'Registry' File, RN 629662-49-3. STN Database [online]. Entry Date: Dec. 22, 2003, retrieved on Jul. 24, 2015.
Chemical Abstracts Service, 'Registry' File, RN 849644-14-0; STN Database SciFinder® [online]. Entry Date: Nov. 2, 2004, retrieved on Mar. 25, 2014.
Clunes, M.T. et al. (2008) "Front-runners for pharmacotherapeutic correction of the airway ion transport defect in cystic fibrosis" *Current Opinion in Pharmacology*, 8(3):292-299.
Collawn, J.F. et al. (2010) "Targets for cystic fibrosis therapy: proteomic analysis and correction of mutant cystic fibrosis transmembrane conductance regulator" *Expert Review of Proteomics*, 7(4):495-506.
Cuthbert, A.W. (2010) "New horizons in the treatment of cystic fibrosis" *Br J Pharmacol*, 163:173-183.
De Meeus, A. et al. (1998) "Genetic Findings in Congenital Bilateral Aplasia of Vas Deferens Patients and Identification of Six Novel Mutations" *Human Mutation, Mutation in Brief*, #138 [online]. DOI: 10.1002/(SICI)1098-1004(1998)11:6<480::AID-HUMU10>3.0.CO;2-Z, 10 pages. Final publication in vol. 11(6), p. 480.
Dhar, T.G. M. et al. (2003) "3-Cyanoindole-based Inhibitors of Inosine Monophosphate Dehydrogenase: Synthesis and Initial Structure-Activity Relationships" *Bioorg. Med. Chem. Lett.*, 13(20):3557-3560.
Dif, F. et al. (2004) "Severe osteopenia in CFRT-null mice" *Bone*, 35:595-603.
Dohmori, R. et al. (1976) "Synthetic Chemotherapeutic Agents. I. Synthesis of 2-Substituted Thiazolo[5,4-f]quinoline Derivatives" *Chem Pharm Bull*, 24:130-135.
Eckford, P.D.W. et al. (2012) "Cystic Fibrosis Transmembrane Conductance Regulator (CFTR) Potentiator VX-770 (Ivacaftor) Opens the Defective Channel Gate of Mutant CFTR in a Phosphorylation-dependent but ATP-independent Manner" *J Biol Chem*, 287(44):36639-36649.
Erlinger, S. (2011) "Molecular repair of a defective CFTR protein in cystic fibrosis" *Clinics and Research in Hepatology and Gastroenterology*, 35:254-256.

Flume, P. A. et al. (2012) "Ivacaftor in Subjects With Cystic Fibrosis Who Are Homozygous for the F508del-CFTR Mutation" *Chest*, 142:718-724.
Galietta, L.J.V. et al. (2001) "Novel CFTR Chloride Channel Activators Identified by Screening of Combinatorial Libraries Based on Flavone and Benzoquinolizinium Lead Compounds" *J Biol Chem*, 276(23):19723-19728.
Grant, D.J.W. (1999) "Theory and Origin of Polymorphism" in *Polymorphism in Pharmaceutical Solids*, H.G. Brittain, Ed.; Ch.1, pp. 1-10.
Grohe, K. et al. (1987) "Synthese von 1-amino-4-chinolon-3-carbonsauren" *Liebigs Annalen Der Chemie*, 10:871-879.
Guillory, J.K. (1999) "Generation of Polymorphs, Hydrates, Solvates, and Amorphous Solids" in *Polymorphism in Pharmaceutical Solids*. H.G. Brittain, Ed.; Ch.5, pp. 183-226.
Guo, J-H. (Jun. 2004) "Lactose in Pharmaceutical Applications" *Drug Delivery*, vol. 4, No. 5 (7 pages).
Hama, T. et al. (2003) "Palladium-Catalyzed α-Arylation of Esters and Amides under More Neutral Conditions" *J Am Chem Soc*, 125(37):11176-11177.
Hancock, B.C. et al. (2000) "What is the True Solubility Advantage for Amorphous Pharmaceuticals?" *Pharmaceutical Research*, 17(4):397-404.
*Handbook for Preparing Crystal of Organic Compound—Principle and Know-how*, Maruzen Co., Ltd Jul. 25, 2008, pp. 57-84 (Japanese).
Hansen, K.T. et al. (Aug. 1991) "Carbamate ester prodrugs of dopaminergic compounds: synthesis, stability, and bioconversion" *J Pharm Sci*, 80(8):793-798.
Haynes, R.K. et al. (1972) "Amine Oxidation and the Chemistry of Quinone Imines. Part I. 3-Methoxy-4-t-butylaniline" *J Chem Soc, Perkins Trans*, 1:396-408.
Heilbron, I.M. et al. (1928) "The Intermolecular Condensation of Acetylmethylanthranilic Acid by Means of Phosphorus Pentachloride and the Formation of a Complex isoCyanine Dye" *J Chem Soc*, pp. 934-941.
Hennequin, L.F. et al. (1999) "Design and Structure-Activity Relationship of a New Class of Potent VEGF Receptor Tyrosine Kinase Inhibitors" *J Med Chem*, 42(26):5369-5389.
Hester, J.B. et al. (1964) "Enzyme Inhibitory Activity of 3-(2-Aminobutyl)indole Derivatives" *J Med Chem*, 7(3):274-279.
Hoffman, H.E. et al. (2005) "Allele-Specific Inhibitors of Protein Tyrosine Phosphatases" *J Am Chem Soc*, 127(9):2824-2825.
Imanishi, T. et al. (1996) "Evidence that a Hybrid Molecule of Norfloxacin and Biphenylacetic Acid is a Potent Antagonist at the GABAA Receptor" *Neuropharmacology*, 35(9/10):1271-1277.
International Patent Application No. PCTUS2005/022768, filed Jun. 24, 2005, by Vertex Pharmaceuticals Incorporated: International Search Report and Written Opinion, dated Jul. 25, 2006.
International Patent Application No. PCT/US2006/048810, filed Dec. 21, 2006, by Vertex Pharmaceuticals Incorporated: International Search Report and Written Opinion, dated Jul. 26, 2007.
International Patent Application No. PCT/US2006/048900, filed Dec. 21, 2006, by Vertex Pharmaceuticals Incorporated: International Search Report and Written Opinion, dated May 25, 2007.
International Patent Application No. PCT/US2006/049421, filed Dec. 28, 2006, by Vertex Pharmaceuticals, Inc.: International Search Report and Written Opinion, dated Sep. 25, 2007.
International Patent Application No. PCT/US2007/068857, filed May 14, 2007, by Vertex Pharmaceuticals Incorporated: International Search Report and Written Opinion, dated Sep. 9, 2008.
International Patent Application No. PCT/US2008/010728, filed Sep. 15, 2008, by Vertex Pharmaceuticals Incorporated: International Search Report and Written Opinion, dated Jul. 14, 2010.
International Patent Application No. PCT/US2009/004629, filed Aug. 13, 2009, by Vertex Pharmaceuticals Incorporated: International Search Report and Written Opinion, dated Mar. 24, 2011.
International Patent Application No. PCT/US2010/024609, filed Feb. 18, 2010, by Vertex Pharmaceuticals Incorporated: International Search Report and Written Opinion, dated Jun. 1, 2010.
International Patent Application No. PCT/US2010/028062, filed Mar. 19, 2010, by Vertex Pharmaceuticals Incorporated: International Search Report and Written Opinion, dated May 27, 2010.

(56) References Cited

OTHER PUBLICATIONS

International Patent Application No. PCT/US2010/028069, filed Mar. 19, 2010, by Vertex Pharmaceuticals Incorporated: International Search Report and Written Opinion, dated Aug. 25, 2010.
International Patent Application No. PCT/US2010/059920, filed Dec. 10, 2010, by Vertex Pharmaceuticals Incorporated: International Search Report and Written Opinion, dated Feb. 3, 2011.
International Patent Application No. PCT/US2011/029276, filed Mar. 21, 2011, by Vertex Pharmaceuticals Incorporated: International Search Report and Written Opinion, dated May 11, 2011.
International Patent Application No. PCT/US2011/033687, filed Apr. 22, 2011, by Vertex Pharmaceuticals Incorporated: International Search Report and Written Opinion, dated Aug. 30, 2011.
International Patent Application No. PCT/US2011/033689, filed Apr. 22, 2011, by Vertex Pharmaceuticals Incorporated: International Search Report and Written Opinion, dated Aug. 30, 2011.
International Patent Application No. PCT/US2011/033693, filed Apr. 22, 2011, by Vertex Pharmaceuticals Incorporated: International Search Report and Written Opinion, dated Aug. 30, 2011.
International Patent Application No. PCT/US2011/037457, filed May 20, 2011, by Vertex Pharmaceuticals Incorporated: International Search Report and Written Opinion, dated Jul. 13, 2011.
International Patent Application No. PCT/US2011/049467, filed Aug. 26, 2011, by Vertex Pharmaceuticals Incorporated: International Search Report and Written Opinion, dated Apr. 2, 2012.
International Patent Application No. PCT/US2012/034578, filed Apr. 20, 2012, by Vertex Pharmaceuticals Incorporated: International Search Report and Written Opinion, dated Mar. 21, 2013.
International Patent Application No. PCT/US2012/063398, filed Nov. 2, 2012, by Vertex Pharmaceuticals Incorporated: International Search Report and Written Opinion, dated Jan. 23, 2013.
International Patent Application No. PCT/US2013/028097, filed Feb. 27, 2013, by Vertex Pharmaceuticals Incorporated: International Search Report and Written Opinion, dated May 10, 2013.
International Patent Application No. PCT/US2013/044838, filed Jun. 7, 2013, by Vertex Pharmaceuticals Incorporated: International Search Report and Written Opinion, dated Aug. 5, 2013.
International Patent Application No. PCT/US2015/054565, filed Oct. 7, 2015, by Vertex Pharmaceuticals Incorporated: International Search Report and Written Opinion, dated Jan. 11, 2016.
International Search Report and Written Opinion dated Jan. 11, 2016, in International Patent Application No. PCT/US2015/054577.
Irie, K. et al. (1995) "Synthesis of 6-Substituted Indolactams by Microbial Conversion" *Tetrahedron*, 51(22):6255-6266.
Iskandarani, B. et al. (1993) "Simultaneous Optimization of Capsule and Tablet Formulation Using Response Surface Methodology" *Drug Dev Industrial Pharmacy*, 19(16):2089-2101.
Ito, Y. et al. (1996) "Inhibition of GABAA Receptor Chloride Channel by Quinolones and Norfloxacin-Biphenylacetic Acid Hybrid Compounds" *Neuropharmacology*, 35(9/10):1263-1269.
Jivraj, M. et al. (Feb. 2000) "An overview of the different excipients useful for the direct compression of tablets" *PSTT*, 3(2):58-63.
Johannesson, J. et al. (Aug. 2012) "CFTR Regulates Early Pathogenesis of Chronic Obstructive Lung Disease in βENaC-Overexpressing Mice" *PLoS ONE*, 7(8):e44059 (11 pages).
Johnson, H.E. et al. (1963) "Reactions of Indole. IV. The Synthesis of Some Aminoindoles" *J Org Chem*, 28(10):2794-2797.
Jones, A.M. and J.M. Helm (2009) "Emerging Treatments in Cystic Fibrosis" *Drugs*, 69(14)1903-1910.
Kaminsky, D. et al. (1968) "Quinolone Antibacterial Agents. Oxolinic Acid and Related Compounds" *J Med Chem*, 11(1):160-163.
Kapranov, N.I. et al. (2004) "Cystic fibrosis: Recent Progress and Problems" *Medical Genetics*, 3(9):398-412, with English translation.
Kurata, H. et al. (2004) "A novel class of apical sodium-dependent bile acid transporter inhibitors: the amphiphilic 4-oxo-1-phenyl-1,4-dihydroquinoline derivatives" *Bioorg. Med. Chem. Lett.*, 14:1183-1186.

Levine, M.H. et al. (2005) "CFTR-Regulated Chloride Transport at the Ocular Surface in Living Mice Measured by Potential Differences" *Invest Ophthal Vis Sci*, 46(4):1428-1434.
Loo, T.W. et al. (2011) "Corrector-mediated rescue of misprocessed CFTR mutants can be reduced by the P-glycoprotein drug pump" *Biochem Pharmacol*, 83(3):345-354.
Ma, T. et al. (2002) "High-affinity Activators of Cystic Fibrosis Transmembrane Conductance Regulator (CFTR) Chloride Conductance Identified by High-Throughput Screening" *J. Biol. Chem.*, 277(40):37235-37241.
Mall, M. et al. (2000) "Effect of genistein on native epithelial tissue from normal individuals and CF patients and on ion channels expressed in Xenopus oocytes" *Br J Pharmacol*, 130:1884-1892.
Mandour, A.H. et al. (1999) "Aminolysis and Hydrolysis of Indolyl Oxazolones" *Egyptian J Chem*, 42(3):251-266.
Marivingt-Mounir, C. et al. (Feb. 2004) "Synthesis, SAR, crystal structure, and biological evaluation of benzoquinoliziniums as activators of wild-type and mutant cystic fibrosis transmembrane conductance regulator channels" *J Med Chem*, 47(4):962-972.
Mashkovskiy, M.D., *Medicaments. Manual for Doctors*. vol. 1, 14th Edition. Moscow: LLC "Novaya Volna", 2001; p. 11.
Miles, E.W. and R.S. Phillips (1985) "Photoinactivation and photoaffinity labeling of tryptophan synthase $\alpha_2\beta_2$ complex by the product analogue 6-azido-L-tryptophan" *Biochem*, 24(17):4694-4703.
Motherwell, W.D.S. et al. (2000) "Automated assignment of graph-set descriptors for crystallographically symmetric molecules" *Acta Cryst*, B56:466-473.
Nishikawa, Y. et al. (1989) "Synthesis and Antiallergic Activity of N-[4-(4-Diphenylmethyl-1-piperazinyl)butyl]-1,4-dihydro-4-oxopyridine-3-carboxamides" *Chem Pharm Bull*, 37(5):1256-1259.
Noone, P.G. et al. (2001) "'CFTR-opathies': disease phenotypes associated with cystic fibrosis transmembrane regulator gene mutations" *Respiratory Research*, 2(6):1-5.
Nosova, E.V., et al. (2002) "Synthesis of new fluorinated derivatives of Quinolinecarboxylic acids" *Chem. of Heter. Compounds*, 38(8):922-928. Translated from: *Khimiya Geterotsiklicheskikh Soedinenii*, No. 8, pp. 1060-1066.
Notice of Allowance and Fee(s) Due for U.S. Appl. No. 13/290,491, dated Oct. 25, 2012.
Notice of Allowance and Fee(s) Due for U.S. Appl. No. 13/871,349, dated Apr. 17, 2015.
Notice of Allowance and Fee(s) Due for U.S. Appl. No. 13/871,349, dated Aug. 12, 2014.
Notice of Allowance and Fee(s) Due for U.S. Appl. No. 13/871,349, dated Oct. 13, 2015.
Notice of Allowance and Fee(s) Due for U.S. Appl. No. 13/887,839, dated Feb. 2, 2015.
Notice of Allowance and Fee(s) Due for U.S. Appl. No. 13/887,839, dated Jul. 7, 2014.
Notice of Allowance and Fee(s) Due for U.S. Appl. No. 13/887,839, dated Oct. 16, 2014.
Notice of Allowance and Fee(s) Due for U.S. Appl. No. 13/887,839, dated Sep. 30, 2015.
Notice of Allowance and Fee(s) Due for U.S. Appl. No. 14/031,360, dated Aug. 14, 2014.
Notice of Allowance and Fee(s) Due for U.S. Appl. No. 14/298,245, dated Jul. 21, 2015.
Notice of Allowance and Fee(s) Due for U.S. Appl. No. 14/298,245, dated Nov. 12, 2015.
Notice of Allowance and Fee(s) Due for U.S. Appl. No. 14/326,930, dated Aug. 14, 2015.
Notice of Allowance and Fee(s) Due for U.S. Appl. No. 14/326,930, dated Dec. 8, 2015.
Notice of Allowance and Fee(s) Due for U.S. Appl. No. 14/334,902, dated Feb. 18, 2016.
Notice of Allowance and Fee(s) Due for U.S. Appl. No. 14/334,902, dated Oct. 19, 2015.
Notice of Allowance and Fee(s) Due for U.S. Appl. No. 14/532,791, dated Jul. 24, 2015.
Notice of Allowance and Fee(s) Due for U.S. Appl. No. 14/532,791, dated Mar. 1, 2016.
Notice of Allowance and Fee(s) Due for U.S. Appl. No. 14/532,791, dated Nov. 6, 2015.

(56) References Cited

OTHER PUBLICATIONS

Notice of Allowance and Fee(s) Due for U.S. Appl. No. 14/567,475, dated Jan. 5, 2016.
Notice of Allowance and Fee(s) Due for U.S. Appl. No. 14/567,475, dated Sep. 21, 2015.
Notice of Allowance and Fee(s) Due for U.S. Appl. No. 14/579,098, dated Feb. 1, 2016.
Notice of Allowability for U.S. Appl. No. 14/579,098, dated Apr. 18, 2016.
Notice of Allowance and Fee(s) Due for U.S. Appl. No. 14/579,098, dated May 12, 2016.
Notice of Allowance and Fee(s) Due for U.S. Appl. No. 14/656,043, dated Aug. 4, 2016.
Notice of Allowance and Fee(s) Due for U.S. Appl. No. 14/687286, dated Feb. 10, 2016.
Notice of Allowance and Fee(s) Due for U.S. Appl. No. 14/687,286, dated May 19, 2016.
Notice of Allowance and Fee(s) Due for U.S. Appl. No. 14/687,286, dated Sep. 28, 2016.
Notice of Allowance and Fee(s) Due for U.S. Appl. No. 14/877,914, dated Jul. 27, 2016.
Notice of Allowance and Fee(s) Due for U.S. Appl. No. 14/877,914, dated Nov. 14, 2016.
Notice of Allowance and Fee(s) Due for U.S. Appl. No. 14/925,804, dated May 17, 2016, Celia C. Chang.
Notice of Allowance and Fee(s) Due for U.S. Appl. No. 15/001,036, dated Feb. 10, 2017.
Notice of Allowance and Fee(s) Due for U.S. Appl. No. 15/073,591, dated Sep. 28, 2016, Celia C. Chang.
Paranjape, S.M. et al. (2008) "Atypical Cystic fibrosis and CFTR-Related Diseases" *Clinic Rev Allerg Immunol*, 35(3):116-123.
Paritala, H. et al. (2009) "Benzo(h)quinoline derivatives as G-quadruplex binding agents" *Bioorg Med Chem Lett*, 19(8):1584-1587.
Pedemonte, N. et al. (2005) "Phenylglycine and sulfonamide correctors of defective ΔF508 and G551D cystic fibrosis transmembrane conductance regulator chloride-channel gating" *Molecular Pharmacology*, 67(5):1797-1807.
Pedemonte, N. et al. (2005) "Small-molecule correctors of defective ΔF508-CFTR cellular processing identified by high-throughput screening" *J Clin Invest*, 115(9):2564-2571.
Pencharz, P.D. and P.R. Durie (2000) "Pathogenesis of malnutrition in cystic fibrosis, and its treatment" *Clin Nutr*, 19(6):387-394.
Pérez-Guille, B. et al. (2004) "Pharmacokinetics of a cephalone (CQ-M-EPCA) in rats after oral, intraduodenal and intravenous administration" *Intl J Pharm*, 282(1-2):87-94.
Porst, H. and L. Kny (1985) "Zur Struktur der Abbauprodukte von Neostigminbromid (On the Structure of Degradation Products of Neostigmine bromide" *Pharmazie*, 40(5):325-328. German with English translation.
Pubchem Compound No. CID 29877; Database Record No. 19962-04-0; Create Date Jul. 19, 2005 [online]. Retrieved from: http://pubchem.ncbi.nlm.nih.gov/summary/summary.cgi?cid=29877; on Jan. 16, 2014 (4 pages).
Roberts, R.M. (1949) "The reaction of diarylformamidines with ethyl malonate" *J Org Chem*, 14(2):277-284.
Sashida, H. et al. (1990) "Studies of Seven Membered Heterocycles. XXXII. Synthesis of N-Unsubstituted 1H-1, 4-Benzodiazepines Stabilized by Intramolecular Hydrogen Bonding" *Chem Pharm Bull*, 38(11):2919-2925.
Sen, A.B. et al. (1947) "Synthesis of Substituted Dinitrophenyl Ketones, and Phenylacetic Acids. Part I." *J. Indian Chem. Soc.*, 24:268-270.
Sen, A.B., et al. (1948) "Synthesis of Substituted Dinitro Phenylketones and Phenylacetic Acids. Part III." *J Indian Chem Soc*, 25:282-284.
Sen, A.B., et al. (1948) "Synthesis of Substituted Dinitrophenyl Ketones and Phenylacetic Acids. Part IV." *J Indian Chem Soc*, 25(8):403-404.
Settimj, G. et al. (1988) "β-Carbolines as agonistic or antagonistic benzodiazepine receptor ligands. 1. Synthesis of some 5-, 6- and 7-amino derivatives of 3-methoxycarbonyl-β-carboline (β-CCM) and of 3-ethoxycarbonyl-β-carboline (β-CCE)" *J Heterocyclic Chem*, 25(5):1391-1397.
Shead et al. (2007) "Cystic fibrosis transmembrane conductance regulator (CFTR) is expressed in human bone" *Thorax*, 62:650-651.
Shioji, Y. (Jan. 27, 2003) *Manufacture Technology of Solid Preparation*. CMC Publishing Co., Ltd.; pp. 9, 12, and 13 (Japanese).
Showalter, H.D.H. et al. (1996) "Concise Syntheses of the Novel 1H-Pyrrolo[3,2-g]quinazoline Ring System and its [2,3-f] Angular Isomer" *J Org Chem*, 61(3):1155-1158.
Silverman, R.B. (1992) *The Organic Chemistry of Drug Design and Drug Action*. San Diego, CA: Academic Press; pp. 5-51.
Sloane, P.A. et al. (2010) "Translational readthrough of premature stop codons combined with CFTR potentiation: potential for combination CFTR therapy" *Pediatric Pulmonology*, 45(33):313, Abstract 264.
Sloane, P.A. et al. (2012) "A Pharmacologic Approach to Acquired Cystic Fibrosis Transmembrane Conductance Regulator Dysfunction in Smoking Related Lung Disease" *PLoS ONE*, 7(6):e39809 (13 pages).
Srivastava, S.K. et al. (2000) "Quinolones: Novel Probes in Antifilarial Chemotheraphy" *J Med Chem*, 43(11):2275-2279.
Thomson, S.A. et al. (2009) "Minitablets: New Modality to Deliver Medicines to Preschool-Aged Children" *Pediatrics*, 123:e235 (6 pages).
Thomson Scientific, Database WPI, Accession No. 2001-425173; Week 200145.
Tissen, C. et al. (2011) "Development of mini-tablets with 1 mm and 2 mm diameter" *Int J Pharmaceutics*, 416:164-170.
Tonghui, M.A. et al. (2002) "High-affinity Activators of Cystic Fibrosis Transmembrane Conductance Regulator (CFTR) Chloride Conductance Identified by High-throughput Screening" *J Biol Chem*, 277(40):37235-37241.
Tsui, L-C. (1992) "Mutations and Sequence Variations Detected in the Cystic Fibrosis Transmembrane Conductance Regulator (CFTR) Gene: A Report From the Cystic Fibrosis Genetic Analysis Consortium" *Human Mutation*, 1:197-203.
Tzetis, M. et al. (2001) "CFTR gene mutations—including three novel nucleotide substitutions—and haplotype background in patients with asthma, disseminated bronchiectasis and chronic obstructive pulmonary disease" *Hum Genet*, 108:216-221.
U.S. Department of Health and Human Services, Food and Drug Administration (Dec. 2002) *Guidance for Industry. Food-Effect Bioavailability and Fed Bioequivalence Studies*. (9 pages).
U.S. Appl. No. 15/234,877, filed Aug. 11, 2016, by Hadida-Ruah et al.
U.S. Appl. No. 15/342,999, filed Nov. 3, 2016, by Alargova et al.
Van Es, T. et al. (2001) "N,1-Dialkyl-7-(alkylamino)-4-(alkylimino)-1,4-dihydroquinoline-3-carboxamides and their 4-oxo derivatives: Synthesis and properties" *S. Afr. J. Chem.*, 54:102-117.
Van Es, T. et al. (2002) "1-alkyl-1,4-dihydro-4-iminoquinoline-3-carboxylic acids: Synthesis, Structure, and Properties" *S. Afr. J. Chem.*, 55:13-33.
Van Goor, F. et al. (2006) "Rescue of ΔF580-CFTR trafficking and gating in human cystic fibrosis airway primary cultures by small molecules" *Am J Physiol Lung Cell Mol Physiol*, 290(6)L1117-L1130.
Van Goor, F. et al. (2009) "Rescue of CF airway epithelial cell function in vitro by a CFTR potentiator, VX-770" *J. Cystic Fibrosis*, vol. 8, Supplement 2, Abstracts of the 32nd European Cystic Fibrosis Conference Jun. 10-13, 2009, Abstract 67, p. S17.
Van Goor, F. et al. (2009) "Rescue of CF airway epithelial cell function in vitro by a CFTR potentiator, VC-770" *PNAS*, 106(44):18825-18830.
Vertex Pharmaceuticals, Inc. (May 17, 2006) "Vertex Pharmaceuticals Initiates Phase I Development for VX-770 in Cystic Fibrosis" [online]. Retrieved from: http://files.shareholder.com/downloads/VRTX/641260063x0x84745/fc8ddd6d-3713-48bb-b689-0444fc7ad623/VRTX_News_2006_5_17_General.pdf (2 pages).
Vertex Pharmaceuticals, Inc. (Aug. 5, 2009) "Study of VX-770 in Cystic Fibrosis Subjects Age 12 and Older Homozygous for the F508del-CFTR Mutation" [online]. *ClinicalTrials.gov*, Identifier:

(56) References Cited

OTHER PUBLICATIONS

NCT00953706. Retrieved from the Internet: http://clinicaltrials.gov/archive/NCT00953706/2009_08_05, on Jul. 10, 2013 (2 pages).

Vertex Pharmaceuticals, Inc. (Jul. 12, 2010) "Study of the Effect of VX-770 on Hyperpolarized Helium-3 Magnetic Resonance Imaging in Subjects Wth Cystic Fibrosis and the G551D Mutation" [online]. *ClinicalTrials.gov*, Identifier: NCT01161537. Retrieved from the Internet: hftp://clinicaltrials.gov/archive/NCT01262352/2010_12_16, on Jul. 9, 2013 (2 pages).

Vertex Pharmaceuticals, Inc. (Oct. 31, 2011) "Study of VX-809 Alone and in Combination With VX-770 in Cystic Fibrosis (CF) Patients Homozygous or Heterozygous for the F508del-CFTR Mutation" [online]. *ClinicalTrials.gov*, Identifier: NCT01225211. Retrieved from the Internet: http://clinicaltrials.gov/archive/NCT01225211/2011_10_31, on Jul. 10, 2013 (2 pages).

Vertex Pharmaceuticals, Inc. (Jan. 2012) *KALYDECO™(ivacaftor) Tablets. Patient Information.* Reference ID: 3079771 (13 pages).

Vestner, A. et al. (2008) "Neue Therapieansatze bei Cystischer Fibrose (New Therapy Approaches in Cystic Fibrosis)" *Pharmazie in unserer Zeit*, 37(5): 354-355. doi:10.1002/pauz.200890069, with English translation.

Wentland, M.P. et al. (1993) "Mammalian Topoisomerase II Inhibitory Activity of 1-Cyclopropyl-6,8-difluoro-1,4-dihydro-7-(2,6-dimethyl-4-pyridinyl)-4-oxo-3-quinolinecarboxylic Acid and Related Derivatives" *J Med Chem*, 36:2801-2809.

Yu, H. et al. (2010) "VX-770, an investigational CFTR potentiator, acts on multiple CFTR forms in vitro" *Pediatric Pulmonology*, 45(33):318-319, Abstract 280.

Yu, H. et al. (2012) "Ivacaftor potentiation of multiple CFTR channels with gating mutations" *J Cystic Fibrosis*, 11(3):237-245.

Akama, T. et al. (Jun. 1997) "Design and synthesis of potent antitumor 5,4'-diaminoflavone derivatives based on metabolic considerations" *J Med Chem*, 40(12):1894-1900.

Alhalaweh, A. et al. (2015) "Physical stability of drugs after storage above and below the glass transition temperature: Relationship to glass-forming ability" Int J Pharm, 495(1):312-317.

Baghel, S. et al. (2016) "Polymeric Amorphous Solid Dispersions: A Review of Amorphization, Crystallization, Stabilization, Solid-State Characterization, and Aqueous Solubilization of Biopharmaceutical Classification System Class II Drugs" J Pharm Sci, 105(9):2527-2544.

Bombieri et al., "Recommendations for the classification of diseases of CFTR-related disorders," *J. Cyst Fibros* 10:2 S86-S102 (2011).

Cheung, J. et al. (Feb. 2008) "Misfolding of the cystic fibrosis transmembrane conductance regulator and disease" *Biochemistry*, 47(6):1465-1473.

Clemence, F. et al. (Jul. 1988) "4-Hydroxy-3-quinolinecarboxamides with antiarthritic and analgesic activities" *J Med Chem*, 31(7):1453-1462.

Cystic Fibrosis Centre at the Hospital for Sick Children in Toronto, *Cystic Fibrosis Mutation Database*. [online] Retrieved from: http://www.genet.sickkids.on.ca/cftr/app, on Jul. 20, 2018.

Dean, M. et al. (Jun. 1990) "Multiple mutations in highly conserved residues are found in mildly affected cystic fibrosis patients" Cell, 61:863-870.

Hancock, B. and Zografi, G. (1997) "Characteristics and significance of the amorphous state in pharmaceutical systems" J Pharm Sci, 86(1):1-12.

Huang, Y. and Dai, W. G. (2014) "Fundamental aspects of solid dispersion technology for poorly soluble drugs" Acta Pharm Sin B, 4(1):18-25.

Jermain, S. V. et al. (2018) "Amorphous solid dispersions and nanocrystal technologies for poorly water-soluble drug delivery—An update" Int J Pharm, 535(1-2):379-392.

Leusen, F.J.J. (1996) "Ab initio prediction of polymorphs" *J Crystal Growth*, 166:900-903.

Martínez-Ohárriz, M.C. (1994) "Polymorphism of diflunisal: Isolation and solid-state characteristics of a new crystal form" *J Pharm Sci*, 83:174-177.

Newman, A. et al. (2012) "Assessing the performance of amorphous solid dispersions" J Pharm Sci, 101(4):1355-1377.

Notice of Allowance and Fee(s) Due for U.S. Appl. No. 14/027,791, dated Jul. 31, 2015.

Notice of Allowance and Fee(s) Due for U.S. Appl. No. 14/687,286, dated Dec. 1, 2017.

Notice of Allowance and Fee(s) Due for U.S. Appl. No. 14/687,286, dated May 9, 2018.

Notice of Allowance and Fee(s) Due for U.S. Appl. No. 15/001,036, dated May 1, 2018.

Notice of Allowance and Fee(s) Due for U.S. Appl. No. 15/152,092, dated May 17, 2018.

Notice of Allowance and Fee(s) Due for U.S. Appl. No. 15/342,999, dated Apr. 17, 2018.

Notice of Allowance and Fee(s) Due for U.S. Appl. No. 14/676,205, dated May 24, 2018.

Patel, H. et al. (Aug. 2011) "New pharmaceutical excipients in solid dosage forms—A review" *Intl J Pharm & Life Sci*, 2(8):1006-1019.

Rahman, Z. et al. (2013) "Tacrolimus Properties and Formulations: Potential Impact of Product Quality on Safety and Efficacy" 1-39.

Swanepoel, E. et al. (2003) "Quality evaluation of generic drugs by dissolution test: changing the USP dissolution medium to distinguish between active and non-active mebendazole polymorphs" *Eur J Pharma Biopharma*, 55:345-349.

Tao, T. (Dec. 31, 2011) "The progress and applications of flavoring and taste-masking technologies in new oral dosage forms" *Shanghai Medical & Pharmaceutical Journal*, 32(5):252-255 (Chinese; English Abstract on p. 252).

U.S. Appl. No. 15/898,683, filed Feb. 19, 2018, by Frederick F. Van Goor, et al.

U.S. Appl. No. 15/937,564, filed Mar. 27, 2018, by Frederick F. Van Goor, et al.

U.S. Appl. No. 15/949,404, filed Apr. 10, 2018, by Sara Sabina Hadida Ruah.

Wu, L-S. et al. (1994) "Investigation of moricizine hydrochloride polymorphs" J Pharm Sci, 83(10):1404-1406. Xu, W. et al. (Dec. 31, 2005) "Drug administration and dosage forms for children" Journal of Pharmaceutical Practice, 23(2):119-120 (Chinese).

Xu, W. et al. (Dec. 31, 2005) "Drug administration and dosage forms for children" *Journal of Pharmaceutical Practice*, 23(2):119-120 (Chinese).

Aulton, M.E. (Ed.) (2002) *Pharmaceutics: The Science of Dosage Design*. 2nd Ed. Churchill Livingston; p. 116.

Aulton, M.E. (Ed.) (2007) *Pharmaceutics: The Science of Dosage Design*. 3rd Ed. Churchill Livingston; p. 340.

Aungst, B.J. et al. (1987) "Prodrugs for improved oral nalbuphine bioavailability: inter-species differences in the disposition of nalbuphine and its acetylsalicylate and anthranilate esters" *Int. J. Pharm.*, 38:199-209.

Bauer, K.H. et al. (2007) *Lehrbuch der Pharmazeutischen Technologie.* Stuttgart: Wissenschaftliche Verlagsgesellschaft mbH; pp. 214-217, with English translation.

Chiou, W.L. et al. (1971) "Pharmaceutical Applications of Solid Dispersion Systems" *J Pharm Sci*, 60(9):1281-1302.

Gardner, C.R. et al. (2004) "Drugs as Materials: Valuing Physical Form in Drug Discovery" *Nat Rev Drug Discov*, 3:926-934.

Hegde, S. et al. (2006) "To Market, to Market—2005" *Annu Rep Med Chem*, 41:439-477.

Mullins, J.D. et al. (1960) "Some Pharmaceutical Properties of Novobiocin" *J. Am. Pharm. Assoc*. 49(4):245-248.

Notice of Opposition for EP Patent Application No. 06848237.1, dated Nov. 11, 2017.

Shangari, N. et al. (2005) "Sulfation and Glucuronidation of Phenols: Implications in Coenzyme Q Metabolism" *Methods Enzymol*, 400:342-359.

Stella, V.J. et al. (1999) "Aqueous Solubility and Dissolution Rate Does Not Adequately Predict in vivo Performance: A probe Utilizing Some N-Acyloxymethyl Phenytoin Prodrugs" *J Pharm Sci*, 88(8):775-779.

Summary of Product Characteristics for Telxir® and Agenerase®.

Tanno, F. et al. (2004) "Evaluation of Hypromellose Acetate Succinate (HPMCAS) as a Carrier in Solid Dispersions" *Drug Dev Ind Pharm*, 30(1):9-17.

(56) References Cited

OTHER PUBLICATIONS

Thomas, V.H. et al. (2006) "The road map to oral bioavailability: an industrial perspective" *Expert Opin Drug Metabol Toxicol*, 2(4):591-608.

U.S. Appl. No. 60/754,381, filed Dec. 28, 2005, by Patricia Hurter.

European Patent Application No. 06848237.1 (U.S. Pat. No. 1993360), filed Mar. 31, 2008, by Vertex Pharmaceuticals Inc.: Notice of Opposition by Georg Kalhammer and Stephan Teipel, dated Nov. 3, 2017 (10 pages).

Ferec, C. et al. (2012) "Assessing the Disease-Liability of Mutations in CFTR" *Cold Spring Harbor Perspect Med*, 2:a009480 (13 pages).

Sekiguchi, K. et al. (1961) "Studies on Absorption of Eutectic Mixture. I. A Comparison of the Behavior of Eutectic Mixture of Sulfathazole and that of Ordinary Sulfathiazole in Man" Chem. Pharm. Bull. 9:866-872.

U.S. Appl. No. 16/035,938, filed Jul. 16, 2018, by Rossitza Gueorguieva Alargova et al.

U.S. Appl. No. 16/059,724, filed Aug. 9, 2018, by Tanoury et al.

Van Es, T. et al. (2001) "N,1-Dialkyl-7-(alkylamino)-4-(alkylimino)-1,4-dihydroguinoline-3-carboxamides and their 4-oxo derivatives: Synthesis and properties" *S. Afr. J. Chem.*, 54:102-117.

Zeitlin, P.L. (2000) "Pharmacologic restoration of ΔF508 CFTR-mediated chloride current" *Kidney International*, 57:832-837.

Zubrick, J.W. (1988) *The Organic Chem Lab Survival Manual. A Student's Guide to Techniques*. New York: John Wiley & Sons, Inc.; 346 pages.

\* cited by examiner

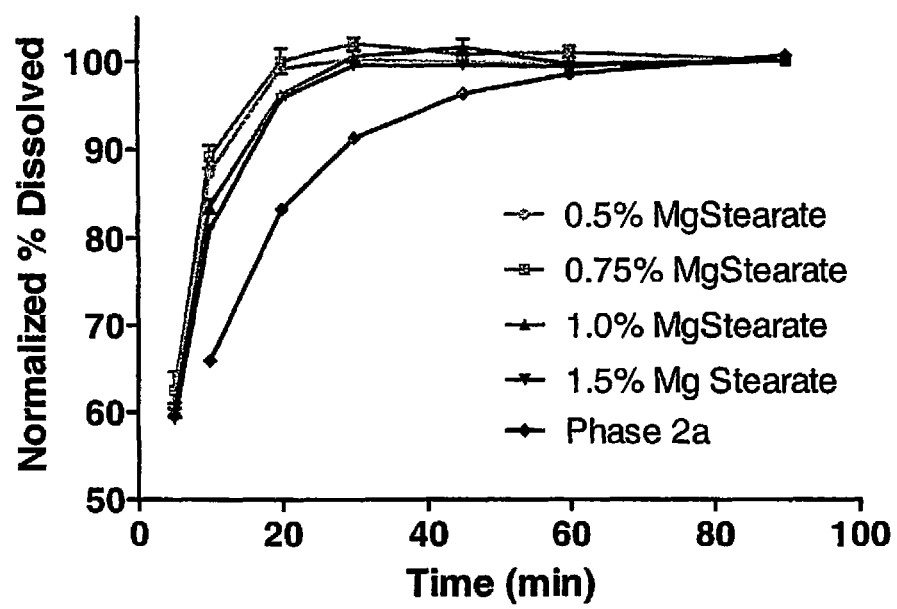

PHARMACEUTICAL COMPOSITION AND ADMINISTRATIONS THEREOF

CROSS-REFERENCE TO RELATED APPLICATIONS

This application claims priority to U.S. Ser. No. 61/088,704 filed on Aug. 13, 2008, U.S. Ser. No. 61/088,801, filed on Aug. 14, 2008, U.S. Ser. No. 61/090,096, filed on Aug. 19, 2008, U.S. Ser. No. 61/146,163, filed on Jan. 21, 2009, U.S. Ser. No. 61/181,527, filed on May 27, 2009, and U.S. Ser. No. 61/183,345, filed on Jun. 2, 2009, each of which is incorporated by reference in their entirety.

FIELD OF THE INVENTION

The present invention relates to pharmaceutical compositions comprising a solid dispersion of N-[2,4-Bis(1,1-dimethylethyl)-5-hydroxyphenyl]-1,4-dihydro-4-oxoquinoline-3-carboxamide, and methods of manufacturing and administering pharmaceutical compositions comprising N-[2,4-Bis(1,1-dimethylethyl)-5-hydroxyphenyl]-1,4-dihydro-4-oxoquinoline-3-carboxamide.

BACKGROUND

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs, known as potentiators that increase the probability of CFTR channel opening represent one potential therapeutic strategy to treat CF.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial Na+ channel, ENaC, Na+/2Cl−/K+ co-transporter, Na+-K+-ATPase pump and the basolateral membrane K+ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the Na+-K+-ATPase pump and Cl ion channels expressed on the basolateral surface of the cell. Secondary active transport of chloride from the luminal side leads to the accumulation of intracellular chloride, which can then passively leave the cell via Cl— channels, resulting in a vectorial transport. Arrangement of Na+/2Cl−/K+ co-transporter, Na+-K+-ATPase pump and the basolateral membrane K+ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

N-[2,4-bis(1,1-dimethylethyl)-5-hydroxyphenyl]-1,4-dihydro-4-oxoquinoline-3-carboxamide is a potent and selective CFTR potentiator of wild-type and mutant (including e.g., ΔF508, R117H, and G551D) forms of human CFTR. N-[2,4-bis(1,1-dimethylethyl)-5-hydroxyphenyl]-1,4-dihydro-4-oxoquinoline-3-carboxamide is useful for treatment of adult patients with cystic fibrosis and at least one G551D-CFTR allele.

Accordingly, there is a need for stable bioavailable pharmaceutical compositions of N-[2,4-bis(1,1-dimethylethyl)-5-hydroxyphenyl]-1,4-dihydro-4-oxoquinoline-3-carboxamide useful for treating patients suffering from CF and methods of administering the same.

SUMMARY OF THE INVENTION

In general, the invention relates to pharmaceutical compositions comprising a solid dispersion of N-[2,4-bis(1,1-dimethylethyl)-5-hydroxyphenyl]-1,4-dihydro-4-oxoquinoline-3-carboxamide ("Compound 1"). The pharmaceutical compositions may also include one or more of the following excipients: a filler, a disintegrant, a glidant, a lubricant, a binder, and a surfactant.

In one embodiment, the present invention provides a pharmaceutical composition comprising a solid dispersion of amorphous Compound 1, wherein the solid dispersion comprises about 25 mg of amorphous Compound 1. In certain embodiments, the solid dispersion comprises about 25 mg of substantially amorphous Compound 1.

In one embodiment, the present invention provides a pharmaceutical composition comprising a solid dispersion of amorphous Compound 1, wherein the solid dispersion comprises about 50 mg of amorphous Compound 1. In certain embodiments, the solid dispersion comprises about 50 mg of substantially amorphous Compound 1.

In one embodiment, the present invention provides a pharmaceutical composition comprising a solid dispersion of amorphous Compound 1, wherein the solid dispersion comprises about 75 mg of amorphous Compound 1. In certain embodiments, the solid dispersion comprises about 75 mg of substantially amorphous Compound 1.

In one embodiment, the present invention provides a pharmaceutical composition comprising a solid dispersion of amorphous Compound 1, wherein the solid dispersion comprises about 100 mg of amorphous Compound 1. In certain embodiments, the solid dispersion comprises about 100 mg of substantially amorphous Compound 1.

In one embodiment, the present invention provides a pharmaceutical composition comprising a solid dispersion of amorphous Compound 1, wherein the solid dispersion comprises about 150 mg of amorphous Compound 1. In certain embodiments, the solid dispersion comprises about 150 mg of substantially amorphous Compound 1.

In one embodiment, the present invention provides a pharmaceutical composition comprising a solid dispersion of amorphous Compound 1, wherein the solid dispersion comprises about 250 mg of amorphous Compound 1. In certain embodiments, the solid dispersion comprises about 250 mg of substantially amorphous Compound 1.

In one aspect, the solid form of Compound 1 in the pharmaceutical composition is a solid dispersion comprising substantially amorphous or amorphous Compound 1 and a polymer, such as hydroxypropylmethylcellulose (HPMC), hydroxypropylmethylcellulose acetate succinate (HPMCAS), vinylpyrrolidone/vinyl acetate copolymer (PVP/VA), polyvinylpyrrolidone (PVP), methacrylic acid/methacrylate copolymers, hydroxypropyl cellulose (HPC), or any combination thereof. Embodiments of this aspect include one or more of the following: The solid dispersion is a powder having mean particle diameter of greater than about 5 μm or the solid dispersion has a bulk density of about 0.10 g/cc or greater.

In some instances, the solid dispersion has a concentration of at least 20 wt % of Compound 1, by weight of the solid dispersion. In other instances, the solid dispersion comprises 80 wt % or less of HPMCAS or PVP/VA. Some solid dispersions comprise from about 40 wt % to about 60 wt % of substantially amorphous or amorphous Compound 1 by weight of the solid dispersion and from about 60 wt % to about 40 wt % of polymer by weight of the solid dispersion. Other solid dispersions comprise from about 65 wt % to about 95 wt % of substantially amorphous or amorphous Compound 1 by weight of the solid dispersion and from about 45 wt % to about 5 wt % of polymer by weight of the solid dispersion.

Solid dispersions can also optionally comprise additives such as a surfactant (e.g., sodium lauryl sulfate (SLS)), which can be present in a concentration of less than 10 wt % of surfactant by weight of solid dispersion.

Still other solid dispersions comprise from about 45 wt % to about 85 wt % of substantially amorphous or amorphous Compound 1, from about 0.45 wt % to about 0.55 wt % of SLS, and from about 14.45 wt % to about 55.55 wt % of HPMCAS or PVP/VA by weight of the solid dispersion.

In still further embodiments, the pharmaceutical compositions also comprise a filler (e.g., lactose, sorbitol, celluloses, calcium phosphates, starches, sugars (e.g., mannitol, sucrose, or the like) or any combination thereof) in concentrations of at least about 10 wt % by weight of the composition; a disintegrant (e.g., sodium croscarmellose, sodium starch glycolate, or a combination thereof) in concentrations of about 10 wt % or less by weight of the composition; a surfactant (e.g., sodium lauryl sulfate, sodium stearyl fumarate (SSF), polyoxyethylene 20 sorbitan mono-oleate, or any combination thereof) in concentrations of about 10 wt % or less by weight of the composition; a binder (e.g., microcrystalline cellulose, dibasic calcium phosphate, sucrose, corn (maize) starch, modified cellulose (e.g., hydroxymethyl cellulose), or any combination thereof) in concentrations of at least about 1 wt % by weight of the composition; a glidant (e.g., colloidal silicon dioxide, talc, or a combination thereof) in concentrations of about 2 wt % or less by weight of the composition; and a lubricant (e.g., magnesium stearate, stearic acid, hydrogenated oil, sodium stearyl fumarate, or any combination thereof) in concentrations of about 2 wt % or less by weight of the composition.

Such pharmaceutical compositions can optionally comprise one or more colorants, fragrances, and/or flavors to enhance its visual appeal, taste, and scent.

Another aspect of the present invention provides a pharmaceutical composition consisting of a tablet that comprises a solid dispersion, a filler, a disintegrant, a surfactant, a binder, a glidant, and a lubricant, wherein the tablet has a dissolution of at least about 50% in about 30 minutes, and the solid dispersion comprises substantially amorphous Compound 1. As noted below, dissolution is measured with a standard USP Type II apparatus that employs a dissolution media of 0.6% sodium lauryl sulfate dissolved in 900 mL of DI water (or a volume of media having the same ratio of SLS to DI water) at a temperature of about 37° C. A single experimental tablet is tested in each test vessel of the apparatus. Dissolution can also be measured with a standard USP Type II apparatus that employs a dissolution media of 0.7% sodium lauryl sulfate dissolved in 900 mL of 50 mM sodium phosphate buffer (pH 6.8) at a temperature of about 37° C. Dissolution can also be measured with a standard USP Type II apparatus that employs a dissolution media of 0.5% sodium lauryl sulfate dissolved in 900 mL of 50 mM sodium phosphate buffer (pH 6.8) at a temperature of about 37° C. A single experimental tablet is tested in each test vessel of the apparatus.

Another aspect of the present invention provides a pharmaceutical composition consisting of a tablet that comprises a solid dispersion comprising amorphous or substantially amorphous Compound 1 and HPMCAS or PVP/VA; and, a filler, a disintegrant, a surfactant, a binder, a glidant, and a lubricant, wherein the tablet has a hardness of at least about 5 Kp.

In yet another aspect, the tablets described herein are coated.

In another aspect, the coated tablets described herein are colored.

In still another aspect, the colored, coated tablets include text or images. For instance, the text or images can be printed on the colored, coated tablet.

In still other aspects, the colored, coated tablets include about 3 wt % of a film coating comprising a blue colorant, such as OPADRY® II. In some embodiments, the colored tablets can be labeled with a logo and text indicating the strength of the active ingredient in the tablet using a black ink, such as Opacode® WB or Opacode® S-1-17823. In still further embodiments, the colored, coated tablets are coated with a colorant, waxed, and then labeled with a logo, other image, and/or text using a suitable ink. In some embodiments, the tablets are coated with about 3 wt % of colorant, and waxed with Carnauba wax powder weighed out in the amount of about 0.01% w/w of the starting tablet core weight. The waxed tablets can be labeled with a logo and text indicating the strength of the active ingredient in the tablet using a suitable ink.

Another aspect of the present invention provides a method of producing a pharmaceutical composition comprising the steps of providing an admixture of a solid dispersion of amorphous Compound 1, a binder, a glidant, a surfactant, a lubricant, a disintegrant, and a filler, and compressing the admixture into a tablet having a dissolution of at least about 50% in about 30 minutes. In one example, the admixture is compressed to a hardness of at least about 5 Kp.

Another aspect of the present invention provides a method of producing a pharmaceutical composition comprising the steps of providing an admixture of a solid dispersion of amorphous Compound 1, a binder, a glidant, a surfactant, a lubricant, a disintegrant, and a filler, and compressing the admixture into a tablet having a dissolution of at least about 70% in about 30 minutes.

Another aspect of the present invention provides a method of administering a pharmaceutical composition by orally administering to a patient at least once per day at least one tablet comprising a solid dispersion of substantially amorphous or amorphous Compound 1, a filler, a binder, a glidant, a disintegrant, a surfactant, and a lubricant, in which the solid dispersion comprises at least about 25 mg of substantially amorphous or amorphous Compound 1. In some embodiments, the tablet is orally administered to the patient once per day. Other tablets useful in this method comprise a solid dispersion containing at least about 50 mg of substantially amorphous or amorphous Compound 1 Some tablets useful in this method comprise a solid dispersion containing at least about 75 mg of substantially amorphous or amorphous Compound 1. Other tablets useful in this method comprise a solid dispersion containing at least about 100 mg of substantially amorphous or amorphous Compound 1. Yet other tablets useful in this method comprise a solid dispersion containing at least about 150 mg of substantially amorphous or amorphous Compound 1. In another method, the administration comprises orally administering to a patient at least once per day at least one tablet comprising a solid dispersion of substantially amorphous or amorphous Compound 1, a filler, a binder, a glidant, a disintegrant, a surfactant, and a lubricant, in which the solid dispersion contains at least about 250 mg of substantially amorphous or amorphous Compound 1.

In some embodiments, the present invention provides for a method of orally administering the pharmaceutical compositions described herein at least once a day. In other embodiments, the present invention provides for a method of orally administering the pharmaceutical composition described herein once a day. In some embodiments, the present invention provides for a method of orally administering the pharmaceutical composition described herein twice a day.

In one aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, Sjogren's disease, Osteoporosis, Osteopenia, Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

BRIEF DESCRIPTION OF THE FIGURES

FIG. 1 presents a graphical illustration of the dissolution profiles of exemplary tablets according to the present invention.

This FIGURE is presented by way of example and is not intended to be limiting.

DETAILED DESCRIPTION

The present invention provides a pharmaceutical composition comprising a solid dispersion of N-[2,4-bis(1,1-dimethylethyl)-5-hydroxyphenyl]-1,4-dihydro-4-oxoquinoline-3-carboxamide, a method of manufacturing a pharmaceutical composition comprising N-[2,4-bis(1,1-dimethylethyl)-5-hydroxyphenyl]-1,4-dihydro-4-oxoquinoline-3-carboxamide, and a method of administering a pharmaceutical composition comprising a solid form of N-[2,4-bis(1,1-dimethylethyl)-5-hydroxyphenyl]-1,4-dihydro-4-oxoquinoline-3-carboxamide.

I. DEFINITIONS

As used herein, the term "active pharmaceutical ingredient" or "API" refers to a biologically active compound. Exemplary APIs include a CF potentiator (e.g., N-[2,4-bis(1,1-dimethylethyl)-5-hydroxyphenyl]-1,4-dihydro-4-oxoquinoline-3-carboxamide).

As used herein, the term "Compound 1" is used interchangeably with "N-[2,4-bis(1,1-dimethylethyl)-5-hydroxyphenyl]-1,4-dihydro-4-oxoquinoline-3-carboxamide", which has the following structure:

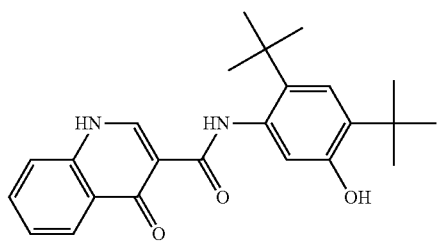 [SMILES: CC(C)(C)c1cc(C(C)(C)C)c(NC(=O)c2c[nH]c3ccccc3c2=O)cc1O]

"Compound 1" also means tautomeric forms such as:

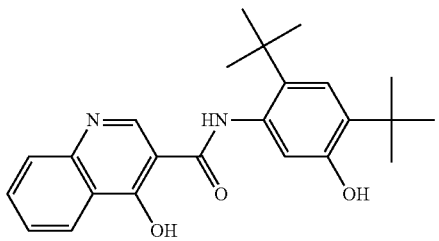 [SMILES: CC(C)(C)c1cc(C(C)(C)C)c(NC(=O)c2cnc3ccccc3c2O)cc1O]

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

As used herein, the term "substantially amorphous" refers to a solid material having little or no long range order in the position of its molecules. For example, substantially amorphous materials have less than about 15% crystallinity (e.g., less than about 10% crystallinity or less than about 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. single molecules, colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include: an amorphous drug in an amorphous polymer; an amorphous drug in crystalline polymer; a crystalline drug in an amorphous polymer; or a crystalline drug in crystalline polymer. In this invention, a solid dispersion can include an amorphous drug in an amorphous polymer or an amorphous drug in crystalline polymer. In some embodiments, a solid dispersion includes the polymer constituting the dispersed phase, and the drug constitutes the continuous phase. Or, a solid dispersion includes the drug constituting the dispersed phase, and the polymer constitutes the continuous phase.

As used herein, the term "solid dispersion" generally refers to a solid dispersion of two or more components, usually one or more drugs (e.g., one drug (e.g., Compound 1)) and polymer, but possibly containing other components such as surfactants or other pharmaceutical excipients, where the drug(s) (e.g., Compound 1) is substantially amorphous (e.g., having about 15% or less (e.g., about 10% or less, or about 5% or less)) of crystalline drug (e.g., N-[2,4-bis(1,1-dimethylethyl)-5-hydroxyphenyl]-1,4-dihydro-4-oxoquinoline-3-carboxamide) or amorphous (i.e., having no crystalline drug), and the physical stability and/or dissolution and/or solubility of the substantially amorphous or amorphous drug is enhanced by the other components. Solid dispersions typically include a compound dispersed in an appropriate carrier medium, such as a solid state carrier. For example, a carrier comprises a polymer (e.g., a water-soluble polymer or a partially water-soluble polymer) and can include optional excipients such as functional excipients (e.g., one or more surfactants) or nonfunctional excipients (e.g., one or more fillers). Another exemplary solid dispersion is a co-precipitate or a co-melt of N-[2,4-bis(1,1-dimethylethyl)-5-hydroxyphenyl]-1,4-dihydro-4-oxoquinoline-3-carboxamide with at least one polymer.

A "Co-precipitate" is a product after dissolving a drug and a polymer in a solvent or solvent mixture followed by the removal of the solvent or solvent mixture. Sometimes the polymer can be suspended in the solvent or solvent mixture. The solvent or solvent mixture includes organic solvents and supercritical fluids. A "co-melt" is a product after heating a drug and a polymer to melt, optionally in the presence of a solvent or solvent mixture, followed by mixing, removal of at least a portion of the solvent if applicable, and cooling to room temperature at a selected rate.

As used herein, "crystallinity" refers to the degree of structural order in a solid. For example, Compound 1, which is substantially amorphous, has less than about 15% crystallinity, or its solid state structure is less than about 15% crystalline. In another example, Compound 1, which is amorphous, has zero (0%) crystallinity.

As used herein, a "CF potentiator" refers to a compound that exhibits biological activity characterized by increasing gating functionality of the mutant CFTR protein present in the cell surface to approximately wild type levels.

As used herein, an "excipient" is an inactive ingredient in a pharmaceutical composition. Examples of excipients include fillers or diluents, surfactants, binders, glidants, lubricants, disintegrants, and the like.

As used herein, a "disintegrant" is an excipient that hydrates a pharmaceutical composition and aids in tablet dispersion. Examples of disintegrants include sodium croscarmellose and/or sodium starch glycolate.

As used herein, a "diluent" or "filler" is an excipient that adds bulkiness to a pharmaceutical composition. Examples of fillers include lactose, sorbitol, celluloses, calcium phosphates, starches, sugars (e.g., mannitol, sucrose, or the like) or any combination thereof.

As used herein, a "surfactant" is an excipient that imparts pharmaceutical compositions with enhanced solubility and/or wetability. Examples of surfactants include sodium lauryl sulfate (SLS), sodium stearyl fumarate (SSF), polyoxyethylene 20 sorbitan mono-oleate (e.g., Tween™), or any combination thereof.

As used herein, a "binder" is an excipient that imparts a pharmaceutical composition with enhanced cohesion or tensile strength (e.g., hardness). Examples of binders include dibasic calcium phosphate, sucrose, corn (maize) starch, microcrystalline cellulose, and modified cellulose (e.g., hydroxymethyl cellulose).

As used herein, a "glidant" is an excipient that imparts a pharmaceutical compositions with enhanced flow properties. Examples of glidants include colloidal silica and/or talc.

As used herein, a "colorant" is an excipient that imparts a pharmaceutical composition with a desired color. Examples of colorants include commercially available pigments such as FD&C Blue #1 Aluminum Lake, FD&C Blue #2, other FD&C Blue colors, titanium dioxide, iron oxide, and/or combinations thereof.

As used herein, a "lubricant" is an excipient that is added to pharmaceutical compositions that are pressed into tablets. The lubricant aids in compaction of granules into tablets and ejection of a tablet of a pharmaceutical composition from a die press. Examples of lubricants include magnesium stearate, stearic acid (stearin), hydrogenated oil, sodium stearyl fumarate, or any combination thereof.

As used herein, "friability" refers to the property of a tablet to remain intact and withhold its form despite an external force of pressure. Friability can be quantified using the mathematical expression presented in equation 1:

$$\% \text{ friability} = 100 \times \frac{(W_0 - W_f)}{W_0} \qquad (1)$$

wherein $W_0$ is the original weight of the tablet and $W_f$ is the final weight of the tablet after it is put through the friabilator.

Friability is measured using a standard USP testing apparatus that tumbles experimental tablets for 100 revolutions. Some tablets of the present invention have a friability of less than about 1% (e.g., less than about 0.75%, less than about 0.50%, or less than about 0.30%)

As used herein, "mean particle diameter" is the average particle diameter as measured using techniques such as laser light scattering, image analysis, or sieve analysis.

As used herein, "bulk density" is the mass of particles of material divided by the total volume the particles occupy. The total volume includes particle volume, inter-particle void volume and internal pore volume. Bulk density is not an intrinsic property of a material; it can change depending on how the material is processed.

II. PHARMACEUTICAL COMPOSITION

In one aspect, the present invention provides a pharmaceutical composition comprising a CF potentiator API (e.g., a solid dispersion of Compound 1).

In one embodiment, the present invention provides a pharmaceutical composition comprising a solid dispersion of substantially amorphous Compound 1, wherein the solid dispersion comprises about 25 mg of substantially amorphous Compound 1.

In one embodiment, the present invention provides a pharmaceutical composition comprising a solid dispersion of substantially amorphous Compound 1, wherein the solid dispersion comprises about 50 mg of substantially amorphous Compound 1.

In one embodiment, the present invention provides a pharmaceutical composition comprising a solid dispersion of substantially amorphous Compound 1, wherein the solid dispersion comprises about 75 mg of substantially amorphous Compound 1.

In one embodiment, the present invention provides a pharmaceutical composition comprising a solid dispersion of substantially amorphous Compound 1, wherein the solid dispersion comprises about 100 mg of substantially amorphous Compound 1.

In one embodiment, the present invention provides a pharmaceutical composition comprising a solid dispersion of substantially amorphous Compound 1, wherein the solid dispersion comprises about 150 mg of substantially amorphous Compound 1.

In one embodiment, the present invention provides a pharmaceutical composition comprising a solid dispersion of substantially amorphous Compound 1, wherein the solid dispersion comprises about 250 mg of substantially amorphous Compound 1.

In one embodiment, the present invention provides a pharmaceutical composition comprising a solid dispersion of amorphous Compound 1, wherein the solid dispersion comprises about 25 mg of amorphous Compound 1.

In one embodiment, the present invention provides a pharmaceutical composition comprising a solid dispersion of amorphous Compound 1, wherein the solid dispersion comprises about 50 mg of amorphous Compound 1.

In one embodiment, the present invention provides a pharmaceutical composition comprising a solid dispersion of amorphous Compound 1, wherein the solid dispersion comprises about 75 mg of amorphous Compound 1.

In one embodiment, the present invention provides a pharmaceutical composition comprising a solid dispersion of amorphous Compound 1, wherein the solid dispersion comprises about 100 mg of amorphous Compound 1.

In one embodiment, the present invention provides a pharmaceutical composition comprising a solid dispersion of amorphous Compound 1, wherein the solid dispersion comprises about 150 mg of amorphous Compound 1.

In one embodiment, the present invention provides a pharmaceutical composition comprising a solid dispersion of amorphous Compound 1, wherein the solid dispersion comprises about 250 mg of amorphous Compound 1.

Another aspect of the present invention provides a pharmaceutical composition comprising a solid dispersion of Compound 1 in which the solid dispersion comprises a polymer.

In one embodiment, the present invention provides a pharmaceutical composition comprising a solid dispersion of substantially amorphous Compound 1 and HPMCAS, wherein the solid dispersion comprises about 25 mg of substantially amorphous Compound 1.

In one embodiment, the present invention provides a pharmaceutical composition comprising a solid dispersion of substantially amorphous Compound 1 and HPMCAS, wherein the solid dispersion comprises about 50 mg of substantially amorphous Compound 1.

In one embodiment, the present invention provides a pharmaceutical composition comprising a solid dispersion of substantially amorphous Compound 1 and HPMCAS, wherein the solid dispersion comprises about 75 mg of substantially amorphous Compound 1.

In one embodiment, the present invention provides a pharmaceutical composition comprising a solid dispersion of substantially amorphous Compound 1 and HPMCAS, wherein the solid dispersion comprises about 100 mg of substantially amorphous Compound 1.

In one embodiment, the present invention provides a pharmaceutical composition comprising a solid dispersion of substantially amorphous Compound 1 and HPMCAS, wherein the solid dispersion comprises about 150 mg of substantially amorphous Compound 1.

In one embodiment, the present invention provides a pharmaceutical composition comprising a solid dispersion of substantially amorphous Compound 1 and HPMCAS, wherein the solid dispersion comprises about 250 mg of substantially amorphous Compound 1.

In one embodiment, the present invention provides a pharmaceutical composition comprising a solid dispersion of amorphous Compound 1 and HPMCAS, wherein the solid dispersion comprises about 25 mg of amorphous Compound 1.

In one embodiment, the present invention provides a pharmaceutical composition comprising a solid dispersion of amorphous Compound 1 and HPMCAS, wherein the solid dispersion comprises about 50 mg of amorphous Compound 1.

In one embodiment, the present invention provides a pharmaceutical composition comprising a solid dispersion of amorphous Compound 1 and HPMCAS, wherein the solid dispersion comprises about 75 mg of amorphous Compound 1.

In one embodiment, the present invention provides a pharmaceutical composition comprising a solid dispersion of amorphous Compound 1 and HPMCAS, wherein the solid dispersion comprises about 100 mg of amorphous Compound 1.

In one embodiment, the present invention provides a pharmaceutical composition comprising a solid dispersion of amorphous Compound 1 and HPMCAS, wherein the solid dispersion comprises about 150 mg of amorphous Compound 1.

In one embodiment, the present invention provides a pharmaceutical composition comprising a solid dispersion of amorphous Compound 1 and HPMCAS, wherein the solid dispersion comprises about 250 mg of amorphous Compound 1.

In one embodiment, the present invention provides a pharmaceutical composition comprising a solid dispersion of substantially amorphous Compound 1 and PVP/VA, wherein the solid dispersion comprises about 25 mg of substantially amorphous Compound 1.

In one embodiment, the present invention provides a pharmaceutical composition comprising a solid dispersion of substantially amorphous Compound 1 and PVP/VA, wherein the solid dispersion comprises about 50 mg of substantially amorphous Compound 1.

In one embodiment, the present invention provides a pharmaceutical composition comprising a solid dispersion of substantially amorphous Compound 1 and PVP/VA, wherein the solid dispersion comprises about 75 mg of substantially amorphous Compound 1.

In one embodiment, the present invention provides a pharmaceutical composition comprising a solid dispersion of substantially amorphous Compound 1 and PVP/VA, wherein the solid dispersion comprises about 100 mg of substantially amorphous Compound 1.

In one embodiment, the present invention provides a pharmaceutical composition comprising a solid dispersion of substantially amorphous Compound 1 and PVP/VA, wherein the solid dispersion comprises about 150 mg of substantially amorphous Compound 1.

In one embodiment, the present invention provides a pharmaceutical composition comprising a solid dispersion of substantially amorphous Compound 1 and PVP/VA, wherein the solid dispersion comprises about 250 mg of substantially amorphous Compound 1.

In one embodiment, the present invention provides a pharmaceutical composition comprising a solid dispersion of amorphous Compound 1 and PVP/VA, wherein the solid dispersion comprises about 25 mg of amorphous Compound 1.

In one embodiment, the present invention provides a pharmaceutical composition comprising a solid dispersion of amorphous Compound 1 and PVP/VA, wherein the solid dispersion comprises about 50 mg of amorphous Compound 1.

In one embodiment, the present invention provides a pharmaceutical composition comprising a solid dispersion of amorphous Compound 1 and PVP/VA, wherein the solid dispersion comprises about 75 mg of amorphous Compound 1.

In one embodiment, the present invention provides a pharmaceutical composition comprising a solid dispersion of amorphous Compound 1 and PVP/VA, wherein the solid dispersion comprises about 100 mg of amorphous Compound 1.

In one embodiment, the present invention provides a pharmaceutical composition comprising a solid dispersion of amorphous Compound 1 and PVP/VA, wherein the solid dispersion comprises about 150 mg of amorphous Compound 1.

In one embodiment, the present invention provides a pharmaceutical composition comprising a solid dispersion of amorphous Compound 1 and PVP/VA, wherein the solid dispersion comprises about 250 mg of amorphous Compound 1.

One aspect of the present invention provides a pharmaceutical composition comprising a CF potentiator API (e.g., a solid dispersion of Compound 1) and other excipients (e.g., a filler, a disintegrant, a surfactant, a binder, a glidant, a colorant, a lubricant, or any combination thereof).

In one embodiment, the present invention provides a pharmaceutical composition comprising:
a. a solid dispersion of substantially amorphous Compound 1 and a polymer;
b. a filler;
c. a disintegrant;
d. a surfactant;
e. a binder;
f. a glidant; and
g. a lubricant,
wherein the solid dispersion comprises about 25 mg of substantially amorphous Compound 1.

In one embodiment, the present invention provides a pharmaceutical composition comprising:
a. a solid dispersion of substantially amorphous Compound 1 and a polymer;
b. a filler;
c. a disintegrant;
d. a surfactant;
e. a binder;
f. a glidant; and
g. a lubricant,
wherein the solid dispersion comprises about 50 mg of substantially amorphous Compound 1.

In another embodiment, the present invention provides a pharmaceutical composition comprising:
a. a solid dispersion of substantially amorphous Compound 1 and a polymer;
b. a filler;
c. a disintegrant;
d. a surfactant;
e. a binder;
f. a glidant; and
g. a lubricant,
wherein the solid dispersion comprises about 75 mg of substantially amorphous Compound 1.

In one embodiment, the present invention provides a pharmaceutical composition comprising:
a. a solid dispersion of substantially amorphous Compound 1 and a polymer;
b. a filler;
c. a disintegrant;
d. surfactant;
e. a binder;
f. a glidant; and
g. a lubricant,
wherein the solid dispersion comprises about 100 mg of substantially amorphous Compound 1.

In one embodiment, the present invention provides a pharmaceutical composition comprising:
a. a solid dispersion of substantially amorphous Compound 1 and a polymer;
b. a filler;
c. a disintegrant;
d. a surfactant;
e. a binder;
f. a glidant; and
g. a lubricant,
wherein the solid dispersion comprises about 150 mg of substantially amorphous Compound 1.

In another embodiment, the present invention provides a pharmaceutical composition comprising:
a. a solid dispersion of substantially amorphous Compound 1 and a polymer;
b. a filler;
c. a disintegrant;
d. a surfactant;
e. a binder;
f. a glidant; and
g. a lubricant,
wherein the solid dispersion comprises about 250 mg of substantially amorphous Compound 1.

In one embodiment, the present invention provides a pharmaceutical composition comprising:
a. a solid dispersion of amorphous Compound 1 and a polymer;
b. a filler;
c. a disintegrant;
d. a surfactant;
e. a binder;
f. a glidant; and
g. a lubricant,
wherein the solid dispersion comprises about 25 mg of amorphous Compound 1.

In one embodiment, the present invention provides a pharmaceutical composition comprising:
a. a solid dispersion of amorphous Compound 1 and a polymer;
b. a filler;
c. a disintegrant;
d. a surfactant;
e. a binder;
f. a glidant; and
g. a lubricant,
wherein the solid dispersion comprises about 50 mg of amorphous Compound 1.

In another embodiment, the present invention provides a pharmaceutical composition comprising:
a. a solid dispersion of amorphous Compound 1 and a polymer;
b. a filler;
c. a disintegrant;
d. a surfactant;
e. a binder;
f. a glidant; and
g. a lubricant,
wherein the solid dispersion comprises about 75 mg of amorphous Compound 1.

In one embodiment, the present invention provides a pharmaceutical composition comprising:

a. a solid dispersion of amorphous Compound 1 and a polymer;
b. a filler;
c. a disintegrant;
d. a surfactant;
e. a binder;
f. a glidant; and
g. a lubricant,
wherein the solid dispersion comprises about 100 mg of amorphous Compound 1.

In one embodiment, the present invention provides a pharmaceutical composition comprising:
a. a solid dispersion of amorphous Compound 1 and a polymer;
b. a filler;
c. a disintegrant;
d. a surfactant;
e. a binder;
f. a glidant; and
g. a lubricant,
wherein the solid dispersion comprises about 150 mg of amorphous Compound 1.

In another embodiment, the present invention provides a pharmaceutical composition comprising:
a. a solid dispersion of amorphous Compound 1 and a polymer;
b. a filler;
c. a disintegrant;
d. a surfactant;
e. a binder;
f. a glidant; and
g. a lubricant,
wherein the solid dispersion comprises about 250 mg of amorphous Compound 1.

In one embodiment, the present invention provides a pharmaceutical composition comprising:
a. a solid dispersion of substantially amorphous Compound 1 and PVP/VA;
b. a filler;
c. a disintegrant;
d. a surfactant;
e. a binder;
f. a glidant; and
g. a lubricant,
wherein the solid dispersion comprises about 25 mg of substantially amorphous Compound 1.

In one embodiment, the present invention provides a pharmaceutical composition comprising:
a. a solid dispersion of substantially amorphous Compound 1 and PVP/VA;
b. a filler;
c. a disintegrant;
d. a surfactant;
e. a binder;
f. a glidant; and
g. a lubricant,
wherein the solid dispersion comprises about 50 mg of substantially amorphous Compound 1.

In another embodiment, the present invention provides a pharmaceutical composition comprising:
a. a solid dispersion of substantially amorphous Compound 1 and PVP/VA;
b. a filler;
c. a disintegrant;
d. a surfactant;
e. a binder;
f. a glidant; and
g. a lubricant,
wherein the solid dispersion comprises about 75 mg of substantially amorphous Compound 1.

In one embodiment, the present invention provides a pharmaceutical composition comprising:
a. a solid dispersion of substantially amorphous Compound 1 and PVP/VA;
b. a filler;
c. a disintegrant;
d. a surfactant;
e. a binder;
f. a glidant; and
g. a lubricant,
wherein the solid dispersion comprises about 100 mg of substantially amorphous Compound 1.

In one embodiment, the present invention provides a pharmaceutical composition comprising:
a. a solid dispersion of substantially amorphous Compound 1 and PVP/VA;
b. a filler;
c. a disintegrant;
d. a surfactant;
e. a binder;
f. a glidant; and
g. a lubricant,
wherein the solid dispersion comprises about 150 mg of substantially amorphous Compound 1.

In another embodiment, the present invention provides a pharmaceutical composition comprising:
a. a solid dispersion of substantially amorphous Compound 1 and PVP/VA;
b. a filler;
c. a disintegrant;
d. a surfactant;
e. a binder;
f. a glidant; and
g. a lubricant,
wherein the solid dispersion comprises about 250 mg of substantially amorphous Compound 1.

In one embodiment, the present invention provides a pharmaceutical composition comprising:
a. a solid dispersion of amorphous Compound 1 and PVP/VA;
b. a filler;
c. a disintegrant;
d. a surfactant;
e. a binder;
f. a glidant; and
g. a lubricant,
wherein the solid dispersion comprises about 25 mg of amorphous Compound 1.

In one embodiment, the present invention provides a pharmaceutical composition comprising:
a. a solid dispersion of amorphous Compound 1 and PVP/VA;
b. a filler;
c. a disintegrant;
d. a surfactant;
e. a binder;
f. a glidant; and
g. a lubricant,
wherein the solid dispersion comprises about 50 mg of amorphous Compound 1.

In another embodiment, the present invention provides a pharmaceutical composition comprising:
a. a solid dispersion of amorphous Compound 1 and PVP/VA;

b. a filler;
c. a disintegrant;
d. a surfactant;
e. a binder;
f. a glidant; and
g. a lubricant,
wherein the solid dispersion comprises about 75 mg of amorphous Compound 1.

In one embodiment, the present invention provides a pharmaceutical composition comprising:
a. a solid dispersion of amorphous Compound 1 and PVP/VA;
b. a filler;
c. a disintegrant;
d. a surfactant;
e. a binder;
f. a glidant; and
g. a lubricant,
wherein the solid dispersion comprises about 100 mg of amorphous Compound 1.

In one embodiment, the present invention provides a pharmaceutical composition comprising:
a. a solid dispersion of amorphous Compound 1 and PVP/VA;
b. a filler;
c. a disintegrant;
d. a surfactant;
e. a binder;
f. a glidant; and
g. a lubricant,
wherein the solid dispersion comprises about 150 mg of amorphous Compound 1.

In another embodiment, the present invention provides a pharmaceutical composition comprising:
a. a solid dispersion of amorphous Compound 1 and PVP/VA;
b. a filler;
c. a disintegrant;
d. a surfactant;
e. a binder;
f. a glidant; and
g. a lubricant,
wherein the solid dispersion comprises about 250 mg of amorphous Compound 1.

In one embodiment, the present invention provides a pharmaceutical composition comprising:
a. a solid dispersion of substantially amorphous Compound 1 and HPMCAS;
b. a filler;
c. a disintegrant;
d. a surfactant;
e. a binder;
f. a glidant; and
g. a lubricant,
wherein the solid dispersion comprises about 25 mg of substantially amorphous Compound 1.

In one embodiment, the present invention provides a pharmaceutical composition comprising:
a. a solid dispersion of substantially amorphous Compound 1 and HPMCAS;
b. a filler;
c. a disintegrant;
d. a surfactant;
e. a binder;
f. a glidant; and
g. a lubricant,
wherein the solid dispersion comprises about 50 mg of substantially amorphous Compound 1.

In another embodiment, the present invention provides a pharmaceutical composition comprising:
a. a solid dispersion of substantially amorphous Compound 1 and HPMCAS;
b. a filler;
c. a disintegrant;
d. a surfactant;
e. a binder;
f. a glidant; and
g. a lubricant,
wherein the solid dispersion comprises about 75 mg of substantially amorphous Compound 1.

In one embodiment, the present invention provides a pharmaceutical composition comprising:
a. a solid dispersion of substantially amorphous Compound 1 and HPMCAS;
b. a filler;
c. a disintegrant;
d. a surfactant;
e. a binder;
f. a glidant; and
g. a lubricant,
wherein the solid dispersion comprises about 100 mg of substantially amorphous Compound 1.

In one embodiment, the present invention provides a pharmaceutical composition comprising:
a. a solid dispersion of substantially amorphous Compound 1 and HPMCAS;
b. a filler;
c. a disintegrant;
d. a surfactant;
e. a binder;
f. a glidant; and
g. a lubricant,
wherein the solid dispersion comprises about 150 mg of substantially amorphous Compound 1.

In another embodiment, the present invention provides a pharmaceutical composition comprising:
a. a solid dispersion of substantially amorphous Compound 1 and HPMCAS;
b. a filler;
c. a disintegrant;
d. a surfactant;
e. a binder;
f. a glidant; and
g. a lubricant,
wherein the solid dispersion comprises about 250 mg of substantially amorphous Compound 1.

In one embodiment, the present invention provides a pharmaceutical composition comprising:
a. a solid dispersion of amorphous Compound 1 and HPMCAS;
b. a filler;
c. a disintegrant;
d. a surfactant;
e. a binder;
f. a glidant; and
g. a lubricant,
wherein the solid dispersion comprises about 25 mg of amorphous Compound 1.

In one embodiment, the present invention provides a pharmaceutical composition comprising:
a. a solid dispersion of amorphous Compound 1 and HPMCAS;
b. a filler;

c. a disintegrant;
d. a surfactant;
e. a binder;
f. a glidant; and
g. a lubricant, wherein the solid dispersion comprises about 50 mg of amorphous Compound 1.

In another embodiment, the present invention provides a pharmaceutical composition comprising:
a. a solid dispersion of amorphous Compound 1 and HPMCAS;
b. a filler;
c. a disintegrant;
d. a surfactant;
e. a binder;
f. a glidant; and
g. a lubricant, wherein the solid dispersion comprises about 75 mg of amorphous Compound 1.

In one embodiment, the present invention provides a pharmaceutical composition comprising:
a. a solid dispersion of amorphous Compound 1 and HPMCAS;
b. a filler;
c. a disintegrant;
d. a surfactant;
e. a binder;
f. a glidant; and
g. a lubricant, wherein the solid dispersion comprises about 100 mg of amorphous Compound 1.

In one embodiment, the present invention provides a pharmaceutical composition comprising:
a. a solid dispersion of amorphous Compound 1 and HPMCAS;
b. a filler;
c. a disintegrant;
d. a surfactant;
e. a binder;
f. a glidant; and
g. a lubricant, wherein the solid dispersion comprises about 150 mg of amorphous Compound 1.

In another embodiment, the present invention provides a pharmaceutical composition comprising:
a. a solid dispersion of amorphous Compound 1 and HPMCAS;
b. a filler;
c. a disintegrant;
d. a surfactant;
e. a binder;
f. a glidant; and
g. a lubricant, wherein the solid dispersion comprises about 250 mg of amorphous Compound 1.

In one embodiment, the pharmaceutical composition comprises a solid dispersion, a filler, a disintegrant, a surfactant, a binder, a glidant, and a lubricant, wherein the solid dispersion comprises Compound 1 and a polymer.

In other embodiments, the pharmaceutical composition comprises a solid dispersion a filler, a disintegrant, a surfactant, a binder, a glidant, and a lubricant, wherein the solid dispersion comprises from about 45 wt % to about 65 wt % (e.g., about 50 wt %) of Compound 1 by weight of the dispersion and a polymer.

In some embodiments, the pharmaceutical composition comprises a solid dispersion a filler, a disintegrant, a surfactant, a binder, a glidant, and a lubricant, wherein the solid dispersion comprises from about 75 wt % to about 95 wt % (e.g., about 80 wt %) of Compound 1 by weight of the dispersion and a polymer.

Suitable solid dispersions of Compound 1, i.e., N-[2,4-bis(1,1-dimethylethyl)-5-hydroxyphenyl]-1,4-dihydro-4-oxoquinoline-3-carboxamide, include, without limitation, those dispersions described in PCT publication no. WO 2007/079139, which is hereby incorporated by reference in its entirety.

In one embodiment, the pharmaceutical composition of the present invention comprises a solid dispersion of Compound 1. For example, the solid dispersion comprises substantially amorphous Compound 1, where Compound 1 is less than about 15% (e.g., less than about 10% or less than about 5%) crystalline, and at least one polymer. In another example, the solid dispersion comprises amorphous Compound 1, i.e., Compound 1 has about 0% crystallinity. The concentration of Compound 1 in the solid dispersion depends on several factors such as the amount of pharmaceutical composition needed to provide a desired amount of Compound 1 and the desired dissolution profile of the pharmaceutical composition.

Polymers useful in these solid dispersions are inert, pharmaceutically acceptable polymers that are at least partially soluble in water or biological fluids. Polymers can include homopolymers (e.g., polysaccharides) or copolymers (e.g., block copolymers). In one example, the solid dispersion comprises substantially amorphous or amorphous N-[2,4-bis(1,1-dimethylethyl)-5-hydroxyphenyl]-1,4-dihydro-4-oxoquinoline-3-carboxamide and at least one polymer independently selected from hydroxypropylmethylcellulose (HPMC), hydroxypropylmethylcellulose acetate succinate (HPMCAS), vinylpyrrolidone/vinyl acetate copolymer (PVP/VA), polyvinylpyrrolidone (PVP), methacrylic acid/methacrylate copolymers, hydroxypropyl cellulose (HPC), or any combination thereof. In another example, the solid dispersion comprises substantially amorphous or amorphous N-[2,4-bis(1,1-dimethylethyl)-5-hydroxyphenyl]-1,4-dihydro-4-oxoquinoline-3-carboxamide and HPMCAS or PVP/VA.

In another embodiment, the pharmaceutical composition comprises a solid dispersion that contains substantially amorphous Compound 1 and HPMCAS or PVP/VA, in which the solid dispersion has a mean particle diameter, measured by light scattering (e.g., using a Malvern Mastersizer available from Malvern Instruments in England) of greater than about 5 µm (e.g., greater than about 6 µm, greater than about 7 µm, greater than about 8 µm, or greater than about 10 µm). For example, the pharmaceutical composition comprises a solid dispersion that contains amorphous Compound 1 and HPMCAS or PVP/VA, in which the solid dispersion has a mean particle diameter, measured by light scattering, of greater than about 5 µm (e.g., greater than about 6 µm, greater than about 7 µm, greater than about 8 µm, or greater than about 10 µm). In another example, the pharmaceutical composition comprises a solid dispersion comprising substantially amorphous Compound 1 and HPMCAS, in which the solid dispersion has a mean particle diameter, measured by light scattering, of from about 7 µm to about 25 µm. For instance, the pharmaceutical composition comprises a solid dispersion comprising amorphous Compound 1 and HPMCAS, in which the solid dispersion has a mean particle diameter, measured by light scattering, of from about 7 µm to about 25 µm. In yet another example, the pharmaceutical composition comprises a solid dispersion comprising substantially amorphous Compound 1 and HPMCAS, in which the solid dispersion has a mean particle diameter, measured by light scattering, of from about 10 μm to about 35 μm. For instance, the pharmaceutical composition comprises a solid dispersion comprising amorphous Compound 1 and HPMCAS, in which the solid dispersion has a mean particle diameter, measured by light scattering, of from about 10 μm to about 35 μm. In another example, the pharmaceutical composition comprises a solid dispersion comprising substantially amorphous Compound 1 and HPMCAS or PVP/VA, in which the solid dispersion has a bulk density of about 0.10 g/cc or greater (e.g., 0.15 g/cc or greater, 0.17 g/cc or greater). For instance, the pharmaceutical composition comprising a solid dispersion comprising amorphous Compound 1 and HPMCAS or PVP/VA, in which the solid dispersion has a bulk density of about 0.10 g/cc or greater (e.g., 0.15 g/cc or greater, 0.17 g/cc or greater). In another instance, the pharmaceutical composition comprises a solid dispersion that comprises substantially amorphous Compound 1 and HPMCAS or PVP/VA, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc). In still another instance, the pharmaceutical composition comprises a solid dispersion that includes amorphous Compound 1 and HPMCAS or PVP/VA, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc). In another example, the pharmaceutical composition comprises a solid dispersion that comprises substantially amorphous Compound 1 and HPMCAS, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc). For instance, the pharmaceutical composition includes a solid dispersion that comprises amorphous Compound 1 and HPMCAS, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc).

Alternative solid dispersions comprise substantially amorphous or amorphous Compound 1 and HPMCAS or PVP/VA, wherein substantially amorphous Compound 1 or amorphous Compound 1 is present in an amount of at least 20 wt % (e.g., at least 40 wt %, at least 45 wt %, at least 49 wt %, or at least 50 wt %) by weight of the solid dispersion. In some embodiments, the solid dispersion comprises HPMCAS or PVP/VA and from about 20 wt % to about 99 wt % (e.g., from about 40 wt % to about 90 wt %, from about 42 wt % to about 88 wt %, from about 45 wt % to about 85 wt %, or from about 50 wt % to about 80 wt %) of substantially amorphous or amorphous Compound 1 by weight of the solid dispersion. For example, the solid dispersion comprises HPMCAS or PVP/VA and from about 40 wt % to about 60 wt % (e.g., from about 42 wt % to about 57 wt %, from about 45 wt % to about 55 wt %, or from about 47 wt % to about 53 wt %) of substantially amorphous or amorphous Compound 1 by weight of the solid dispersion. In another example, the solid dispersion comprises HPMCAS or PVP/VA and from about 65 wt % to about 95 wt % (e.g., from about 67 wt % to about 92 wt %, from about 70 wt % to about 90 wt %, or from about 72 wt % to about 88 wt %) of substantially amorphous Compound 1 or amorphous Compound 1 by weight of the solid dispersion.

In other embodiments, the solid dispersion comprises 80 wt % or less (e.g., 60 wt % or less, 55 wt % or less, or 50 wt % or less) of polymer (e.g., HPMCAS, PVP/VA, PVP, methacrylic acid/methacrylate copolymer, HPC, or any combination thereof) by weight of solid dispersion. In some instances, the solid dispersion comprises from about 1 wt % to about 80 wt % (e.g., from about 10 wt % to about 60 wt %) of polymer (e.g., HPMCAS, PVP/VA, PVP, methacrylic acid/methacrylate copolymer, HPC, or any combination thereof).

Some solid dispersions comprise from about 40 wt % to about 60 wt % (e.g., from about 42 wt % to about 57 wt %, from about 45 wt % to about 55 wt %, or from about 47 wt % to about 53 wt %) of substantially amorphous Compound 1 by weight of the solid dispersion and from about 60 wt % to about 40 wt % of polymer (e.g., HPMCAS, PVP/VA, PVP, methacrylic acid/methacrylate copolymer, HPC, or any combination thereof). Alternative solid dispersions comprise from about 40 wt % to about 60 wt % (e.g., from about 42 wt % to about 57 wt %, from about 45 wt % to about 55 wt %, or from about 47 wt % to about 53 wt %) of amorphous Compound 1 by weight of the solid dispersion and from about 60 wt % to about 40 wt % of polymer (e.g., HPMCAS, PVP/VA, PVP, methacrylic acid/methacrylate copolymer, HPC, or any combination thereof).

Other solid dispersions comprise from about 65 wt % to about 95 wt % (e.g., from about 67 wt % to about 92 wt %, from about 70 wt % to about 90 wt %, or from about 72 wt % to about 88 wt %) of substantially amorphous Compound 1 by weight of the solid dispersion and from about 45 wt % to about 5 wt % of polymer (e.g., HPMCAS, PVP/VA, PVP, methacrylic acid/methacrylate copolymer, HPC, or any combination thereof). For instance, the solid dispersion comprises from about 65 wt % to about 95 wt % (e.g., from about 67 wt % to about 92 wt %, from about 70 wt % to about 90 wt %, or from about 72 wt % to about 88 wt %) of amorphous Compound 1 by weight of the solid dispersion and from about 45 wt % to about 5 wt % of polymer (e.g., HPMCAS, PVP/VA, PVP, methacrylic acid/methacrylate copolymer, HPC, or any combination thereof).

Solid dispersions useful in embodiments of the present invention can optionally comprise a surfactant. Suitable surfactants include sodium lauryl sulfate (SLS), sodium stearyl fumarate (SSF), polyoxyethylene 20 sorbitan mono-oleate (e.g., Tween™), any combination thereof, or the like. In one example, the solid dispersion comprises less than 5 wt % (less than 3.0 wt %, less than 1.5 wt %, or less than 1.0 wt %) of surfactant by weight of solid dispersion. In another example, the solid dispersion comprises from about 0.30 wt % to about 0.80 wt % (e.g., from about 0.35 wt % to about 0.70 wt %, from about 0.40 wt % to about 0.60 wt %, or from about 0.45 wt % to about 0.55 wt %) of surfactant by weight of solid dispersion.

In alternative embodiments, the solid dispersion comprises from about 45 wt % to about 85 wt % of substantially amorphous or amorphous Compound 1, from about 0.45 wt % to about 0.55 wt % of SLS, and from about 14.45 wt % to about 55.55 wt % of HPMCAS or PVP/VA by weight of the solid dispersion. One exemplary solid dispersion contains about 50 wt % of substantially amorphous or amorphous Compound 1, about 49.5 wt % of HPMCAS or PVP/VA, and about 0.5 wt % of SLS, by weight of the solid dispersion. Another exemplary solid dispersion contains about 80 wt % of substantially amorphous or amorphous Compound 1, about 19.5 wt % of HPMCAS or PVP/VA, and about 0.5 wt % of SLS.

In alternative embodiments, the solid dispersion comprises from about 45 wt % to about 85 wt % of substantially amorphous or amorphous Compound 1, from about 0.45 wt % to about 0.55 wt % of SLS, and from about 14.45 wt % to about 55.55 wt % of HPMCAS by weight of the solid dispersion. One exemplary solid dispersion contains about 50 wt % of substantially amorphous or amorphous Compound 1, about 49.5 wt % of HPMCAS, and about 0.5 wt % of SLS, by weight of the solid dispersion. Another exemplary solid dispersion contains about 80 wt % of substantially amorphous or amorphous Compound 1, about 19.5 wt % of HPMCAS or PVP/VA, and about 0.5 wt % of SLS.

In addition to the solid dispersion of Compound 1, pharmaceutical compositions of the present invention also comprise one or more excipients such as fillers, disintegrants, surfactants, binders, glidants, lubricants, colorants, or fragrances.

Fillers suitable for the present invention are compatible with the ingredients of the pharmaceutical composition, i.e., they do not substantially reduce the solubility, the hardness, the chemical stability, the physical stability, or the biological activity of the pharmaceutical composition. Exemplary fillers include lactose, sorbitol, celluloses, calcium phosphates, starches, sugars (e.g., mannitol, sucrose, or the like), or any combination thereof. In one embodiment, the pharmaceutical composition comprises at least one filler in an amount of at least about 10 wt % (e.g., at least about 20 wt %, at least about 25 wt %, or at least about 27 wt %) by weight of the composition. For example, the pharmaceutical composition comprises from about 10 wt % to about 60 wt % (e.g., from about 20 wt % to about 55 wt %, from about 25 wt % to about 50 wt %, or from about 27 wt % to about 45 wt %) of filler, by weight of the composition. In another example, the pharmaceutical composition comprises at least about 20 wt % (e.g., at least 25 wt % or at least 27 wt %) of lactose, by weight of the composition. In yet another example, the pharmaceutical composition comprises from about 20 wt % to about 60 wt % (e.g., from about 25 wt % to about 55 wt % or from about 27 wt % to about 45 wt %) of lactose, by weight of the composition.

Disintegrants suitable for the present invention enhance the dispersal of the pharmaceutical composition and are compatible with the ingredients of the pharmaceutical composition, i.e., they do not substantially reduce the chemical stability, the physical stability, the hardness, or the biological activity of the pharmaceutical composition. Exemplary disintegrants include sodium croscarmellose, sodium starch glycolate, or a combination thereof. In one embodiment, the pharmaceutical composition comprises disintegrant in an amount of about 10 wt % or less (e.g., about 7 wt % or less, about 6 wt % or less, or about 5 wt % or less) by weight of the composition. For example, the pharmaceutical composition comprises from about 1 wt % to about 10 wt % (e.g., from about 1.5 wt % to about 7.5 wt % or from about 2.5 wt % to about 6 wt %) of disintegrant, by weight of the composition. In another example, the pharmaceutical composition comprises about 10 wt % or less (e.g., 7 wt % or less, 6 wt % or less, or 5 wt % or less) of sodium croscarmellose, by weight of the composition. In yet another example, the pharmaceutical composition comprises from about 1 wt % to about 10 wt % (e.g., from about 1.5 wt % to about 7.5 wt % or from about 2.5 wt % to about 6 wt %) of sodium croscarmellose, by weight of the composition. In some examples, the pharmaceutical composition comprises from about 0.1% to about 10 wt % (e.g., from about 0.5 wt % to about 7.5 wt % or from about 1.5 wt % to about 6 wt %) of disintegrant, by weight of the composition. In still other examples, the pharmaceutical composition comprises from about 0.5% to about 10 wt % (e.g., from about 1.5 wt % to about 7.5 wt % or from about 2.5 wt % to about 6 wt %) of disintegrant, by weight of the composition.

Surfactants suitable for the present invention enhance the solubility of the pharmaceutical composition and are compatible with the ingredients of the pharmaceutical composition, i.e., they do not substantially reduce the chemical stability, the physical stability, the hardness, or the biological activity of the pharmaceutical composition. Exemplary surfactants include sodium lauryl sulfate (SLS), sodium stearyl fumarate (SSF), polyoxyethylene 20 sorbitan mono-oleate (e.g., Tween™), any combination thereof, or the like. In one embodiment, the pharmaceutical composition comprises a surfactant in an amount of about 10 wt % or less (e.g., about 5 wt % or less, about 2 wt % or less, about 1 wt % or less, about 0.8 wt % or less, or about 0.6 wt % or less) by weight of the composition. For example, the pharmaceutical composition includes from about 10 wt % to about 0.1 wt % (e.g., from about 5 wt % to about 0.2 wt % or from about 2 wt % to about 0.3 wt %) of surfactant, by weight of the composition. In another example, the pharmaceutical composition comprises 10 wt % or less (e.g., about 5 wt % or less, about 2 wt % or less, about 1 wt % or less, about 0.8 wt % or less, or about 0.6 wt % or less) of sodium lauryl sulfate, by weight of the composition. In yet another example, the pharmaceutical composition comprises from about 10 wt % to about 0.1 wt % (e.g., from about 5 wt % to about 0.2 wt % or from about 2 wt % to about 0.3 wt %) of sodium lauryl sulfate, by weight of the composition.

Binders suitable for the present invention enhance the tablet strength of the pharmaceutical composition and are compatible with the ingredients of the pharmaceutical composition, i.e., they do not substantially reduce the chemical stability, the physical stability, or the biological activity of the pharmaceutical composition. Exemplary binders include microcrystalline cellulose, dibasic calcium phosphate, sucrose, corn (maize) starch, modified cellulose (e.g., hydroxymethyl cellulose), or any combination thereof. In one embodiment, the pharmaceutical composition comprises a binder in an amount of at least about 1 wt % (e.g., at least about 10 wt %, at least about 15 wt %, at least about 20 wt %, or at least about 22 wt %) by weight of the composition. For example, the pharmaceutical composition comprises from about 5 wt % to about 50 wt % (e.g., from about 10 wt % to about 45 wt % or from about 20 wt % to about 45 wt %) of binder, by weight of the composition. In another example, the pharmaceutical composition comprises at least about 1 wt % (e.g., at least about 10 wt %, at least about 15 wt %, at least about 20 wt %, or at least about 22 wt %) of microcrystalline cellulose, by weight of the composition. In yet another example, the pharmaceutical composition comprises from about 5 wt % to about 50 wt % (e.g., from about 10 wt % to about 45 wt % or from about 20 wt % to about 45 wt %) of microcrystalline cellulose, by weight of the composition.

Glidants suitable for the present invention enhance the flow properties of the pharmaceutical composition and are compatible with the ingredients of the pharmaceutical composition, i.e., they do not substantially reduce the solubility, the hardness, the chemical stability, the physical stability, or the biological activity of the pharmaceutical composition. Exemplary glidants include colloidal silicon dioxide, talc, or a combination thereof. In one embodiment, the pharmaceutical composition comprises a glidant in an amount of 2 wt % or less (e.g., 1.75 wt %, 1.25 wt % or less, or 1.00 wt % or less) by weight of the composition. For example, the pharmaceutical composition comprises from about 2 wt % to about 0.05 wt % (e.g., from about 1.5 wt % to about 0.07 wt % or from about 1.0 wt % to about 0.09 wt %) of glidant, by weight of the composition. In another example, the pharmaceutical composition comprises 2 wt % or less (e.g., 1.75 wt %, 1.25 wt % or less, or 1.00 wt % or less) of colloidal silicon dioxide, by weight of the composition. In yet another example, the pharmaceutical composition comprises from about 2 wt % to about 0.05 wt % (e.g., from about 1.5 wt % to about 0.07 wt % or from about 1.0 wt % to about 0.09 wt %) of colloidal silicon dioxide, by weight of the composition.

Lubricants suitable for the present invention improve the compression and ejection of compressed pharmaceutical compositions from a die press and are compatible with the ingredients of the pharmaceutical composition, i.e., they do not substantially reduce the solubility, the hardness, or the biological activity of the pharmaceutical composition. Exemplary lubricants include magnesium stearate, stearic acid (stearin), hydrogenated oil, sodium stearyl fumarate, or any combination thereof. In one embodiment, the pharmaceutical composition comprises a lubricant in an amount of 2 wt % or less (e.g., 1.75 wt %, 1.25 wt % or less, or 1.00 wt % or less) by weight of the composition. For example, the pharmaceutical composition comprises from about 2 wt % to about 0.10 wt % (e.g., from about 1.5 wt % to about 0.15 wt % or from about 1.3 wt % to about 0.30 wt %) of lubricant, by weight of the composition. In another example, the pharmaceutical composition comprises 2 wt % or less (e.g., 1.75 wt %, 1.25 wt % or less, or 1.00 wt % or less) of magnesium stearate, by weight of the composition. In yet another example, the pharmaceutical composition comprises from about 2 wt % to about 0.10 wt % (e.g., from about 1.5 wt % to about 0.15 wt % or from about 1.3 wt % to about 0.30 wt %) of magnesium stearate, by weight of the composition.

Pharmaceutical compositions of the present invention can optionally comprise one or more colorants, flavors, and/or fragrances to enhance the visual appeal, taste, and/or scent of the composition. Suitable colorants, flavors, or fragrances are compatible with the ingredients of the pharmaceutical composition, i.e., they do not substantially reduce the solubility, the chemical stability, the physical stability, the hardness, or the biological activity of the pharmaceutical composition. In one embodiment, the pharmaceutical composition comprises a colorant, a flavor, and/or a fragrance. For example, the pharmaceutical composition comprises less than about 1 wt % (e.g., less than about 0.75 wt % or less than about 0.5 wt %) of each optionally ingredient, i.e., colorant, flavor and/or fragrance, by weight of the composition. In another example, the pharmaceutical composition comprises less than about 1 wt % (e.g., less than about 0.75 wt % or less than about 0.5 wt %) of a colorant. In still another example, the pharmaceutical composition comprises less than about 1 wt % (e.g., less than about 0.75 wt % or less than about 0.5 wt %) of a blue colorant (e.g., FD&C Blue #1 and/or FD&C Blue #2 Aluminum Lake, commercially available from Colorcon, Inc. of West Point, Pa.)

In some embodiments, the pharmaceutical composition can be made into tablets and the tablets can be coated with a colorant and optionally labeled with a logo, other image and/or text using a suitable ink. In still other embodiments, the pharmaceutical composition can be made into tablets and the tablets can be coated with a colorant, waxed, and optionally labeled with a logo, other image and/or text using a suitable ink. Suitable colorants and inks are compatible with the ingredients of the pharmaceutical composition, i.e., they do not substantially reduce the solubility, the chemical stability, the physical stability, the hardness, or the biological activity of the pharmaceutical composition. The suitable colorants and inks can be any color and are water based or solvent based. In one embodiment, tablets made from the pharmaceutical composition are coated with a colorant and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a blue colorant (e.g., OPADRY® II, commercially available from Colorcon, Inc. of West Point, Pa.). The colored tablets can be labeled with a logo and text indicating the strength of the active ingredient in the tablet using a black ink (e.g., Opacode® WB, commercially available from Colorcon, Inc. of West Point, Pa.). In another embodiment, tablets made from the pharmaceutical composition are coated with a colorant, waxed, and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a blue colorant (e.g., OPADRY® II, commercially available from Colorcon, Inc. of West Point, Pa.). The colored tablets can be waxed with Carnauba wax powder weighed out in the amount of about 0.01% w/w of the starting tablet core weight. The waxed tablets can be labeled with a logo and text indicating the strength of the active ingredient in the tablet using a black ink (e.g., Opacode® S-1-17823—a solvent based ink, commercially available from Colorcon, Inc. of West Point, Pa.).

One exemplary pharmaceutical composition comprises from about 5 wt % to about 50 wt % (e.g., from about 5 wt % to about 25 wt %, from about 15 wt % to about 40 wt %, or from about 30 wt % to about 50 wt %) of a solid dispersion, by weight of the composition, comprising from about 40 wt % to about 60 wt % of substantially amorphous Compound 1, by weight of the dispersion, and from about 60 wt % to about 40 wt % of a polymer, by weight of the dispersion; from about 25 wt % to about 50 wt % of a filler; from about 1 wt % to about 10 wt % of a disintegrant; from about 2 wt % to about 0.3 wt % of a surfactant; from about 5 wt % to about 50 wt % of a binder; from about 2 wt % to about 0.05 wt % of a glidant; and from about 2 wt % to about 0.1 wt % of a lubricant. Or, the pharmaceutical composition comprises from about 5 wt % to about 50 wt % (e.g., from about 5 wt % to about 25 wt %, from about 15 wt % to about 40 wt %, or from about 30 wt % to about 50 wt %) of a solid dispersion, by weight of the composition, comprising from about 40 wt % to about 60 wt % of amorphous Compound 1, by weight of the dispersion, and from about 60 wt % to about 40 wt % of a polymer, by weight of the dispersion; from about 25 wt % to about 50 wt % of a filler; from about 1 wt % to about 10 wt % of a disintegrant; from about 2 wt % to about 0.3 wt % of a surfactant; from about 5 wt % to about 50 wt % of a binder; from about 2 wt % to about 0.05 wt % of a glidant; and from about 2 wt % to about 0.1 wt % of a lubricant.

Another exemplary pharmaceutical composition comprises from about 5 wt % to about 50 wt % (e.g., from about 5 wt % to about 25 wt %, from about 15 wt % to about 40 wt %, or from about 30 wt % to about 50 wt %) of a solid dispersion, by weight of the composition, comprising from about 70 wt % to about 90 wt % of substantially amorphous Compound 1, by weight of the dispersion, and from about 30 wt % to about 10 wt % of a polymer, by weight of the dispersion; from about 25 wt % to about 50 wt % of a filler; from about 1 wt % to about 10 wt % of a disintegrant; from about 2 wt % to about 0.3 wt % of a surfactant; from about 5 wt % to about 50 wt % of a binder; from about 2 wt % to about 0.05 wt % of a glidant; and from about 2 wt % to about 0.1 wt % of a lubricant. Or, the pharmaceutical composition comprises from about 5 wt % to about 50 wt % (e.g., from about 5 wt % to about 25 wt %, from about 15 wt % to about 40 wt %, or from about 30 wt % to about 50 wt %) of a solid dispersion, by weight of the composition, comprising from about 70 wt % to about 90 wt % of amorphous Compound 1, by weight of the dispersion, and from about 30 wt % to about 10 wt % of a polymer, by weight of the dispersion; from about 25 wt % to about 50 wt % of a filler; from about 1 wt % to about 10 wt % of a disintegrant; from about 2 wt % to about 0.3 wt % of a surfactant; from about 5 wt % to about 50 wt % of a binder; from about 2 wt % to about 0.05 wt % of a glidant; and from about 2 wt % to about 0.1 wt % of a lubricant.

One pharmaceutical composition of the present invention comprises about 15 wt % of a solid dispersion by weight of the composition, wherein the dispersion comprises about 50 wt % of substantially amorphous Compound 1 by weight of the dispersion, about 49.5 wt % of HPMCAS by weight of the dispersion, and about 0.5 wt % SLS by weight of the dispersion; about 35 wt % of microcrystalline cellulose by weight of the composition; about 43 wt % of lactose by weight of the composition; about 5 wt % of sodium croscarmellose by weight of the composition; about 0.5 wt % of SLS by weight of the composition; about 0.125 wt % of colloidal silicon dioxide by weight of the composition; and about 0.5 wt % of magnesium stearate by weight of the composition. Or, the pharmaceutical composition of the present invention comprises about 15 wt % of a solid dispersion by weight of the composition, wherein the dispersion comprises about 50 wt % of amorphous Compound 1 by weight of the dispersion, about 49.5 wt % of HPMCAS by weight of the dispersion, and about 0.5 wt % SLS by weight of the dispersion; about 35 wt % of microcrystalline cellulose by weight of the composition; about 43 wt % of lactose by weight of the composition; about 5 wt % of sodium croscarmellose by weight of the composition; about 0.5 wt % of SLS by weight of the composition; about 0.125 wt % of colloidal silicon dioxide by weight of the composition; and about 0.5 wt % of magnesium stearate by weight of the composition.

Another pharmaceutical composition of the present invention comprises about 31 wt % of a solid dispersion by weight of the composition, wherein the dispersion comprises about 50 wt % of substantially amorphous Compound 1 by weight of the dispersion, about 49.5 wt % of HPMCAS by weight of the dispersion, and about 0.5 wt % SLS by weight of the dispersion; about 25 wt % of microcrystalline cellulose by weight of the composition; about 38 wt % of lactose by weight of the composition; about 5 wt % of sodium croscarmellose by weight of the composition; about 0.5 wt % of SLS by weight of the composition; about 0.125 wt % of colloidal silicon dioxide by weight of the composition; and about 0.5 wt % of magnesium stearate by weight of the composition. Or, the pharmaceutical composition of the present invention comprises about 31 wt % of a solid dispersion by weight of the composition, wherein the dispersion comprises about 50 wt % of amorphous Compound 1 by weight of the dispersion, about 49.5 wt % of HPMCAS by weight of the dispersion, and about 0.5 wt % SLS by weight of the dispersion; about 25 wt % of microcrystalline cellulose by weight of the composition; about 38 wt % of lactose by weight of the composition; about 5 wt % of sodium croscarmellose by weight of the composition; about 0.5 wt % of SLS by weight of the composition; about 0.125 wt % of colloidal silicon dioxide by weight of the composition; and about 0.5 wt % of magnesium stearate by weight of the composition.

Another pharmaceutical composition of the present invention comprises about 40 wt % of a solid dispersion by weight of the composition, wherein the dispersion comprises about 80 wt % of substantially amorphous Compound 1 by weight of the dispersion, about 19.5 wt % of PVP/VA by weight of the dispersion, and about 0.5 wt % SLS by weight of the dispersion; about 27 wt % of microcrystalline cellulose by weight of the composition; about 27 wt % of lactose by weight of the composition; about 3 wt % of sodium croscarmellose by weight of the composition; about 0.5 wt % of SLS by weight of the composition; about 1 wt % of colloidal silicon dioxide by weight of the composition; about 1 wt % of magnesium stearate by weight of the composition, and about 0.4 wt % of colorant by weight of the composition. Or, the pharmaceutical composition of the present invention comprises about 40 wt % of a solid dispersion by weight of the composition, wherein the dispersion comprises about 80 wt % of amorphous Compound 1 by weight of the dispersion, about 195 wt % of PVP/VA by weight of the dispersion, and about 0.5 wt % SLS by weight of the dispersion; about 27 wt % of microcrystalline cellulose by weight of the composition; about 27 wt % of lactose by weight of the composition; about 3 wt % of sodium croscarmellose by weight of the composition; about 0.5 wt % of SLS by weight of the composition; about 1 wt % of colloidal silicon dioxide by weight of the composition; about 1 wt % of magnesium stearate by weight of the composition, and about 0.4 wt % of colorant by weight of the composition.

Another pharmaceutical composition of the present invention comprises about 40 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 27 wt % of microcrystalline cellulose by weight of the composition; about 27 wt % of lactose by weight of the composition; about 3 wt % of sodium croscarmellose by weight of the composition; about 0.5 wt % of SLS by weight of the composition; about 1 wt % of colloidal silicon dioxide by weight of the composition; about 1 wt % of magnesium stearate by weight of the composition, and about 0.4 wt % of colorant by weight of the composition. Or, the pharmaceutical composition of the present invention comprises about 40 wt % of a solid dispersion by weight of the composition, wherein the dispersion comprises about 80 wt % of amorphous Compound 1 by weight of the dispersion, about 19.5 wt % of HPMCAS by weight of the dispersion, and about 0.5 wt % SLS by weight of the dispersion; about 27 wt % of microcrystalline cellulose by weight of the composition; about 27 wt % of lactose by weight of the composition; about 3 wt % of sodium croscarmellose by weight of the composition; about 0.5 wt % of SLS by weight of the composition; about 1 wt % of colloidal silicon dioxide by weight of the composition; about 1 wt % of magnesium stearate by weight of the composition, and about 0.4 wt % of colorant by weight of the composition.

In still another pharmaceutical composition of the present invention comprises about 34.5 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30 wt % of lactose by weight of the composition; about 3 wt % of sodium croscarmellose by weight of the composition; about 0.5 wt % of SLS by weight of the composition; about 1 wt % of colloidal silicon dioxide by weight of the composition; about 1 wt % of magnesium stearate by weight of the composition.

In yet a further pharmaceutical composition of the present invention, a caplet shaped pharmaceutical tablet composition having a hardness of 9.5 Kp±15 percent comprises about 34 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30 wt % of lactose by weight of the composition; about 3 wt % of sodium croscarmellose by weight of the composition; about 0.5 wt % of SLS by weight of the composition; about 1 wt % of colloidal silicon dioxide by weight of the composition; and about 1 wt % of magnesium stearate by weight of the composition. In certain embodiments, the caplet shaped pharmaceutical tablet contains 150 mg of Compound 1. In certain embodiments, the caplet shaped pharmaceutical tablet contains 100 mg of Compound 1.

In still another pharmaceutical composition of the present invention, a caplet shaped pharmaceutical tablet composition having an initial hardness of 11 Kp±20 percent comprises about 40 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30 wt % of lactose by weight of the composition; about 3 wt % of sodium croscarmellose by weight of the composition; about 0.5 wt % of SLS by weight of the composition; about 1 wt % of colloidal silicon dioxide by weight of the composition; and about 1 wt % of magnesium stearate by weight of the composition. In certain embodiments, the caplet shaped pharmaceutical tablet contains 150 mg of Compound 1.

In still another pharmaceutical composition of the present invention, a caplet shaped pharmaceutical tablet composition having an initial hardness of 11 Kp±20 percent comprises about 34.1 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30.4 wt % of lactose by weight of the composition; about 3 wt % of sodium croscarmellose by weight of the composition; about 0.5 wt % of SLS by weight of the composition; about 1 wt % of colloidal silicon dioxide by weight of the composition; and about 1 wt % of magnesium stearate by weight of the composition. In some aspects, the caplet shaped pharmaceutical tablet composition contains 100 mg of Compound 1. In other aspects, the caplet shaped pharmaceutical tablet composition includes a colorant coating and a printed logo or text. In some embodiments of this aspect, the caplet shaped pharmaceutical tablet composition includes a blue OPADRY® II coating and a water or solvent based ink logo or text. In certain embodiments, the caplet shaped pharmaceutical tablet contains 150 mg of Compound 1.

In another pharmaceutical composition of the present invention, a caplet shaped pharmaceutical tablet composition having an initial hardness of between about 6 and 16 Kp comprises about 34.1 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30.5 wt % of microcrystalline cellulose by weight of the composition; about 30.4 wt % of lactose by weight of the composition; about 3 wt % of sodium croscarmellose by weight of the composition; about 0.5 wt % of SLS by weight of the composition; about 0.5 wt % of colloidal silicon dioxide by weight of the composition; and about 1 wt % of magnesium stearate by weight of the composition. In some aspects, the caplet shaped pharmaceutical tablet composition contains 100 mg of Compound 1. In some further aspects, the caplet shaped pharmaceutical tablet composition comprises a colorant coated, a wax coating, and a printed logo or text. In some embodiments of this aspect, the caplet shaped pharmaceutical tablet includes a blue OPADRY® II coating and a water or solvent based ink logo or text. In some instances, the colorant coating is blue OPADRY® II. In some instances, the wax coating comprises Carnauba wax. In certain aspects, the ink for the printed logo or text is a solvent based ink. In some aspects, the caplet shaped pharmaceutical tablet composition contains 150 mg of Compound 1.

In still another pharmaceutical composition of the present invention, a pharmaceutical tablet composition having an initial hardness of between about 9 and 21 Kp comprises about 34.1 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30.5 wt % of microcrystalline cellulose by weight of the composition; about 30.4 wt % of lactose by weight of the composition; about 3 wt % of sodium croscarmellose by weight of the composition; about 0.5 wt % of SLS by weight of the composition; about 0.5 wt % of colloidal silicon dioxide by weight of the composition; and about 1 wt % of magnesium stearate by weight of the composition. In some embodiments, the caplet shaped pharmaceutical tablet composition contains 150 mg of Compound 1. In some aspects, the caplet shaped pharmaceutical tablet composition further comprises a colorant coated, a wax coating, and a printed logo or text. In some instances, the tablet includes a blue OPADRY® II coating and a water or solvent based ink logo or text. In still other instances, the wax coating comprises Carnauba wax. In some embodiments, the ink for the printed logo or text is a solvent based ink. In some aspects, the caplet shaped pharmaceutical tablet composition contains 100 mg of Compound 1.

In yet a further pharmaceutical composition of the present invention, a pharmaceutical composition comprises about 34 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30 wt % of lactose by weight of the composition; about 3 wt % of sodium croscarmellose by weight of the composition; about 0.5 wt % of SLS by weight of the composition; about 1 wt % of colloidal silicon dioxide by weight of the composition; and about 1 wt % of magnesium stearate by weight of the composition. In certain embodiments, the pharmaceutical composition contains 150 mg of Compound 1. In other embodiments, the pharmaceutical composition contains 100 mg of Compound 1.

In still another pharmaceutical composition of the present invention, a pharmaceutical composition comprises about 40 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30 wt % of lactose by weight of the composition; about 3 wt % of sodium croscarmellose by weight of the composition; about 0.5 wt % of SLS by weight of the composition; about 1 wt % of colloidal silicon dioxide by weight of the composition; and about 1 wt % of magnesium stearate by weight of the composition. In certain embodiments, the pharmaceutical composition contains 150 mg of Compound 1. In other embodiments, the pharmaceutical composition contains 100 mg of Compound 1.

In still another pharmaceutical composition of the present invention, a pharmaceutical composition comprises about 34.1 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30 wt % of microcrystalline cellulose by weight of the composition; about 30.4 wt % of lactose by weight of the composition; about 3 wt % of sodium croscarmellose by weight of the composition; about 0.5 wt % of SLS by weight of the composition; about 1 wt % of colloidal silicon dioxide by weight of the composition; and about 1 wt % of magnesium stearate by weight of the composition. In some aspects, the pharmaceutical composition contains 100 mg of Compound 1. In other embodiments, the pharmaceutical composition contains 150 mg of Compound 1. In other aspects, the pharmaceutical composition is formed as a tablet composition that includes a colorant coating and a printed logo or text. In some embodiments of this aspect, the pharmaceutical tablet composition includes a blue OPADRY® II coating and a water or solvent based ink logo or text.

In another pharmaceutical composition of the present invention, a pharmaceutical composition comprises about 34.1 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30.5 wt % of microcrystalline cellulose by weight of the composition; about 30.4 wt % of lactose by weight of the composition; about 3 wt % of sodium croscarmellose by weight of the composition; about 0.5 wt % of SLS by weight of the composition; about 0.5 wt % of colloidal silicon dioxide by weight of the composition; and about 1 wt % of magnesium stearate by weight of the composition. In some aspects, the pharmaceutical tablet contains 100 mg of Compound 1. In other embodiments, the pharmaceutical composition contains 150 mg of Compound 1. In some further aspects, the pharmaceutical composition is formed as a tablet and comprises a colorant coated, a wax coating, and a printed logo or text. In some embodiments of this aspect, the pharmaceutical tablet includes a blue OPADRY® II coating and a water or solvent based ink logo or text. In some instances, the colorant coating is blue OPADRY® II. In some instances, the wax coating comprises Carnauba wax. In certain aspects; the ink for the printed logo or text is a solvent based ink.

It is also noted that pharmaceutical compositions of the present invention can be processed into a tablet form, capsule form, or suspension that is suited for oral administration or can be reconstituted in an aqueous solvent (e.g., DI water or saline) for oral, IV, or inhalation (e.g., nebulizer) administration.

Another aspect of the present invention provides a pharmaceutical composition consisting of a tablet that includes a CF potentiator API (e.g., a solid dispersion of N-[2,4-bis(1,1-dimethylethyl)-5-hydroxyphenyl]-1,4-dihydro-4-oxoquinoline-3-carboxamide) and other excipients (e.g., a filler, a disintegrant, a surfactant, a binder, a glidant, a colorant, a lubricant, or any combination thereof), each of which is described above and in the Examples below, wherein the tablet has a dissolution of at least about 50% (e.g., at least about 60%, at least about 70%, at least about 80%, at least about 90%, or at least about 99%) in about 30 minutes. In one example, the pharmaceutical composition consists of a tablet that includes a CF potentiator API (e.g., a solid dispersion of Compound 1) and other excipients (e.g., a filler, a disintegrant, a surfactant, a binder, a glidant, a colorant, a lubricant, or any combination thereof), each of which is described above and in the Examples below, wherein the tablet has a dissolution of from about 50% to about 100% (e.g., from about 55% to about 95% or from about 60% to about 90%) in about 30 minutes. In another example, the pharmaceutical composition consists of a tablet that comprises a solid dispersion comprising substantially amorphous or amorphous Compound 1 and HPMCAS or PVP/VA; and, a filler, a disintegrant, a surfactant, a binder, a glidant, and a lubricant, wherein the tablet has a dissolution of at least about 50% (e.g., at least about 60%, at least about 70%, at least about 80%, at least about 90%, or at least about 99%) in about 30 minutes. In still another example, the pharmaceutical composition consists of a tablet that comprises a solid dispersion comprising substantially amorphous or amorphous Compound 1 and HPMCAS or PVP/VA; and, a filler, a disintegrant, a surfactant, a binder, a glidant, and a lubricant, wherein the tablet has a dissolution of from about 50% to about 100% (e.g., from about 55% to about 95% or from about 60% to about 90%) in about 30 minutes.

In one embodiment, the tablet comprises a solid dispersion comprising at least about 25 mg (e.g., at least about 30 mg, at least about 40 mg, or at least about 50 mg) of substantially amorphous or amorphous Compound 1; and PVP/VA and SLS. In another embodiment, the tablet comprises a solid dispersion comprising at least about 25 mg (e.g., at least about 30 mg, at least about 40 mg, at least about 50 mg, at least about 100 mg, or at least 150 mg) of substantially amorphous or amorphous Compound 1; and HPMCAS and SLS.

Dissolution can be measured with a standard USP Type II apparatus that employs a dissolution media of 0.6% sodium lauryl sulfate dissolved in 900 mL of DI water, stirring at about 50-75 rpm at a temperature of about 37° C. A single experimental tablet is tested in each test vessel of the apparatus. Dissolution can also be measured with a standard USP Type H apparatus that employs a dissolution media of 0.7% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus. Dissolution can also be measured with a standard USP Type II apparatus that employs a dissolution media of 0.5% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus.

Another aspect of the present invention provides a pharmaceutical composition consisting of a tablet that comprises a CF potentiator API (e.g., a solid dispersion of Compound 1) and other excipients (e.g., a filler, a disintegrant, a surfactant, a binder, a glidant, a colorant, a lubricant, or any combination thereof), each of which is described above and in the Examples below, wherein the tablet has a hardness of at least about 5 Kp. In one example, the pharmaceutical composition consists of a tablet that comprises a CF potentiator API (e.g., a solid dispersion of Compound 1) and other excipients (e.g., a filler, a disintegrant, a surfactant, a binder, a glidant, a colorant, a lubricant, or any combination thereof), each of which is described above and in the Examples below, wherein the tablet has a hardness of at least about 5 Kp (e.g., at least about 5.5, at least about 6 Kp, or at least about 7 Kp).

III. METHOD OF PRODUCING A PHARMACEUTICAL COMPOSITION

Another aspect of the present invention provides a method of producing a pharmaceutical composition comprising providing an admixture of a solid dispersion of substantially amorphous or amorphous N-[2,4-Bis(1,1-dimethylethyl)-5-hydroxyphenyl]-1,4-dihydro-4-oxoquinoline-3-carboxamide, a binder, a glidant, a surfactant, a lubricant, a disintegrant, and a filler, and compressing the admixture into a tablet having a dissolution of at least about 50% in about 30 minutes.

Each of the ingredients of this admixture is described above and in the Examples below. Furthermore, the admixture can comprise optional additives such as one or more colorants, one or more flavors, and/or one or more fragrances as described above and in the Examples below. And, the relative concentrations (e.g., wt %) of each of these ingredients (and any optional additives) in the admixture is also presented above and in the Examples below. The ingredients constituting the admixture can be provided sequentially or in any combination of additions; and, the ingredients or combination of ingredients can be provided in any order. In one embodiment the lubricant is the last component added to the admixture.

In one embodiment, the admixture comprises a solid dispersion of substantially amorphous Compound 1, a binder, a glidant, a surfactant, a lubricant, a disintegrant, and a filler, wherein each of these ingredients is provided in a powder form (e.g., provided as particles having a mean diameter, measured by light scattering, of 250 μm or less (e.g., 150 μm or less, 100 μm or less, 50 μm or less, 45 μm or less, 40 μm or less, or 35 μm or less)). For instance, the admixture comprises a solid dispersion of amorphous Compound 1, a binder, a glidant, a surfactant, a lubricant, a disintegrant, and a filler, wherein each of these ingredients is provided in a powder form (e.g., provided as particles having a mean diameter, measured by light scattering, of 250 μm or less (e.g., 150 μm or less, 100 μm or less, 50 μm or less, 45 μm or less, 40 μm or less, or 35 μm or less)).

In another embodiment, the admixture comprises a solid dispersion of substantially amorphous Compound 1, a binder, a glidant, a surfactant, a lubricant, a disintegrant, and a filler, wherein each of these ingredients is substantially free of water. Each of the ingredients comprises less than 5 wt % (e.g., less than 2 wt %, less than 1 wt %, less than 0.75 wt %, less than 0.5 wt %, or less than 0.25 wt %) of water by weight of the ingredient. For instance, the admixture comprises a solid dispersion of amorphous Compound 1, a binder, a glidant, a surfactant, a lubricant, a disintegrant, and a filler, wherein each of these ingredients is substantially free of water. To wit, each of the ingredients comprises less than 5 wt % (e.g., less than 2 wt %, less than 1 wt %, less than 0.75 wt %, less than 0.5 wt %, or less than 0.25 wt %) of water by weight of the ingredient.

In another embodiment, compressing the admixture into a tablet is accomplished by filling a form (e.g., a mold) with the admixture and applying pressure to admixture. This can be accomplished using a die press or other similar apparatus. It is also noted that the application of pressure to the admixture in the form can be repeated using the same pressure during each compression or using different pressures during the compressions. In another example, the admixture is compressed using a die press that applies sufficient pressure to form a tablet having a dissolution of about 50% or more at about 30 minutes (e.g., about 55% or more at about 30 minutes or about 60% or more at about 30 minutes). For instance, the admixture is compressed using a die press to produce a tablet hardness of at least about 5 Kp (at least about 5.5 Kp, at least about 6 Kp, at least about 7 Kp, at least about 11 Kp, or at least 21 Kp). In some instances, the admixture is compressed to produce a tablet hardness of between about 6 and 21 Kp.

In some embodiments, tablets comprising a pharmaceutical composition as described herein can be coated with about 3.0 wt % of a film coating comprising a colorant by weight of the tablet. In certain instances, the colorant suspension or solution used to coat the tablets comprises about 20% w/w of solids by weight of the colorant suspension or solution. In still further instances, the coated tablets can be labeled with a logo, other image or text.

In another embodiment, the method of producing a pharmaceutical composition comprises providing an admixture of a solid dispersion of substantially amorphous Compound 1, a binder, a glidant, a surfactant, a lubricant, a disintegrant, and a filler; mixing the admixture until the admixture is substantially homogenous, and compressing the admixture into a tablet as described above or in the Examples below. Or, the method of producing a pharmaceutical composition comprises providing an admixture of a solid dispersion of amorphous Compound 1, a binder, a glidant, a surfactant, a lubricant, a disintegrant, and a filler; mixing the admixture until the admixture is substantially homogenous, and compressing the admixture into a tablet as described above or in the Examples below. For example, the admixture is mixed by stirring, blending, shaking, or the like using hand mixing, a mixer, a blender, any combination thereof, or the like.

When ingredients or combinations of ingredients are added sequentially, mixing can occur between successive additions, continuously throughout the ingredient addition, after the addition of all of the ingredients or combinations of ingredients, or any combination thereof. The admixture is mixed until it has a substantially homogenous composition.

IV. ADMINISTRATION OF A PHARMACEUTICAL FORMULATION

In another aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia; Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Another aspect of the present invention provides a method of administering a pharmaceutical composition by orally administering to a patient at least once per day the composition comprising a solid dispersion of substantially amorphous or amorphous Compound 1, in which the solid dispersion comprises at least about 25 mg of substantially amorphous or amorphous Compound 1.

Another aspect of the present invention provides a method of administering a pharmaceutical composition by orally administering to a patient at least once per day the composition comprising a solid dispersion of substantially amorphous or amorphous Compound 1, in which the solid dispersion comprises at least about 50 mg of substantially amorphous or amorphous Compound 1.

Another aspect of the present invention provides a method of administering a pharmaceutical composition by orally administering to a patient at least once per day the composition comprising a solid dispersion of substantially amorphous or amorphous Compound 1, in which the solid dispersion comprises at least about 75 mg of substantially amorphous or amorphous Compound 1.

Another aspect of the present invention provides a method of administering a pharmaceutical composition by orally administering to a patient at least once per day the composition comprising a solid dispersion of substantially amorphous or amorphous Compound 1, in which the solid dispersion comprises at least about 100 mg of substantially amorphous or amorphous Compound 1.

Another aspect of the present invention provides a method of administering a pharmaceutical composition by orally administering to a patient at least once per day the composition comprising a solid dispersion of substantially amorphous or amorphous Compound 1, in which the solid dispersion comprises at least about 150 mg of substantially amorphous or amorphous Compound 1.

Another aspect of the present invention provides a method of administering a pharmaceutical composition by orally administering to a patient at least once per day the composition comprising a solid dispersion of substantially amorphous or amorphous Compound 1, in which the solid dispersion comprises at least about 250 mg of substantially amorphous or amorphous Compound 1.

Another aspect of the present invention provides a method of administering a pharmaceutical composition by orally administering to a patient twice per day the composition comprising a solid dispersion of substantially amorphous or amorphous Compound 1, in which the solid dispersion comprises at least about 25 mg of substantially amorphous or amorphous Compound 1.

Another aspect of the present invention provides a method of administering a pharmaceutical composition by orally administering to a patient twice per day the composition comprising a solid dispersion of substantially amorphous or amorphous Compound 1, in which the solid dispersion comprises at least about 50 mg of substantially amorphous or amorphous Compound 1.

Another aspect of the present invention provides a method of administering a pharmaceutical composition by orally administering to a patient twice per day the composition comprising a solid dispersion of substantially amorphous or amorphous Compound 1, in which the solid dispersion comprises at least about 75 mg of substantially amorphous or amorphous Compound 1.

Another aspect of the present invention provides a method of administering a pharmaceutical composition by orally administering to a patient twice per day the composition comprising a solid dispersion of substantially amorphous or amorphous Compound 1, in which the solid dispersion comprises at least about 100 mg of substantially amorphous or amorphous Compound 1.

Another aspect of the present invention provides a method of administering a pharmaceutical composition by orally administering to a patient twice per day the composition comprising a solid dispersion of substantially amorphous or amorphous Compound 1, in which the solid dispersion comprises at least about 150 mg of substantially amorphous or amorphous Compound 1.

Another aspect of the present invention provides a method of administering a pharmaceutical composition by orally administering to a patient twice per day the composition comprising a solid dispersion of substantially amorphous or amorphous Compound 1, in which the solid dispersion comprises at least about 250 mg of substantially amorphous or amorphous Compound 1.

Another aspect of the present invention provides a method of administering a pharmaceutical composition by orally administering to a patient once every 12 hours. The composition comprises a solid dispersion of substantially amorphous or amorphous Compound 1, in which the solid dispersion comprises at least about 25 mg of substantially amorphous or amorphous Compound 1.

Another aspect of the present invention provides a method of administering a pharmaceutical composition by orally administering to a patient once every 12 hours. The composition comprises a solid dispersion of substantially amorphous or amorphous Compound 1, in which the solid dispersion comprises at least about 50 mg of substantially amorphous or amorphous Compound 1.

Another aspect of the present invention provides a method of administering a pharmaceutical composition by orally administering to a patient once every 12 hours. The composition comprising a solid dispersion of substantially amorphous or amorphous Compound 1, in which the solid dispersion comprises at least about 75 mg of substantially amorphous or amorphous Compound 1.

Another aspect of the present invention provides a method of administering a pharmaceutical composition by orally administering to a patient once every 12 hours day. The composition comprising a solid dispersion of substantially amorphous or amorphous Compound 1, in which the solid dispersion comprises at least about 100 mg of substantially amorphous or amorphous Compound 1.

Another aspect of the present invention provides a method of administering a pharmaceutical composition by orally administering to a patient once every 12 hours. The composition comprising a solid dispersion of substantially amorphous or amorphous Compound 1, in which the solid dispersion comprises at least about 150 mg of substantially amorphous or amorphous Compound 1.

Another aspect of the present invention provides a method of administering a pharmaceutical composition by orally administering to a patient once every 12 hours. The composition comprising a solid dispersion of substantially amorphous or amorphous Compound 1, in which the solid dispersion comprises at least about 250 mg of substantially amorphous or amorphous Compound 1.

In still other aspects of the present invention, a pharmaceutical composition as described herein is orally administered to a patient once every 24 hours.

Another aspect of the present invention provides a method of administering a pharmaceutical composition by orally administering to a patient once per day the composition comprising a solid dispersion of substantially amorphous or amorphous Compound 1, in which the solid dispersion comprises at least about 25 mg of substantially amorphous or amorphous Compound 1.

Another aspect of the present invention provides a method of administering a pharmaceutical composition by orally administering to a patient once per day the composition comprising a solid dispersion of substantially amorphous or amorphous Compound 1, in which the solid dispersion comprises at least about 50 mg of substantially amorphous or amorphous Compound 1.

Another aspect of the present invention provides a method of administering a pharmaceutical composition by orally administering to a patient once per day the composition comprising a solid dispersion of substantially amorphous or amorphous Compound 1, in which the solid dispersion comprises at least about 75 mg of substantially amorphous or amorphous Compound 1.

Another aspect of the present invention provides a method of administering a pharmaceutical composition by orally administering to a patient once per day the composition comprising a solid dispersion of substantially amorphous or amorphous Compound 1, in which the solid dispersion comprises at least about 100 mg of substantially amorphous or amorphous Compound 1.

Another aspect of the present invention provides a method of administering a pharmaceutical composition by orally administering to a patient once per day the composition comprising a solid dispersion of substantially amorphous or amorphous Compound 1, in which the solid dispersion comprises at least about 150 mg of substantially amorphous or amorphous Compound 1.

Another aspect of the present invention provides a method of administering a pharmaceutical composition by orally administering to a patient once per day the composition comprising a solid dispersion of substantially amorphous or amorphous Compound 1, in which the solid dispersion comprises at least about 250 mg of substantially amorphous or amorphous Compound 1.

Another aspect of the present invention provides a method of administering a pharmaceutical composition comprising orally administering to a patient at least once per day at least one tablet comprising a pharmaceutical composition containing a solid dispersion of substantially amorphous Compound 1, a filler, a binder, a glidant, a disintegrant, a surfactant, and a lubricant, each of which is described above and in the Examples below, wherein the solid dispersion comprises at least 25 mg (e.g., at least 35 mg, at least 40 mg, or at least 45 mg) of substantially amorphous Compound 1.

In some embodiments, the present invention provides a method of administering a pharmaceutical composition comprising orally administering to a patient at least one tablet comprising:
  a. a solid dispersion comprising about 25 mg of substantially amorphous or amorphous Compound 1;
  b. a filler;
  c. a disintegrant;
  d. a surfactant;
  e. a binder;
  f. a glidant; and
  g. a lubricant.

In some embodiments, the present invention provides a method of administering a pharmaceutical composition comprising orally administering to a patient at least one tablet comprising:
  a. a solid dispersion comprising about 50 mg of substantially amorphous or amorphous Compound 1;
  b. a filler;
  c. a disintegrant;
  d. a surfactant;
  e. a binder;
  f. a glidant; and
  g. a lubricant.

In some embodiments, the present invention provides a method of administering a pharmaceutical composition comprising orally administering to a patient at least one tablet comprising:
  a. a solid dispersion comprising about 75 mg of substantially amorphous or amorphous Compound 1;
  b. a filler;
  c. a disintegrant;
  d. a surfactant;

e. a binder;
f. a glidant; and
g. a lubricant.

In some embodiments, the present invention provides a method of administering a pharmaceutical composition comprising orally administering to a patient at least one tablet comprising:
a. a solid dispersion comprising about 100 mg of substantially amorphous or amorphous Compound 1;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 150 mg of substantially amorphous or amorphous Compound 1;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 250 mg of substantially amorphous or amorphous Compound 1;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 25 mg of substantially amorphous or amorphous Compound 1 and PVP/VA;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 50 mg of substantially amorphous or amorphous Compound 1 and PVP/VA;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 75 mg of substantially amorphous or amorphous Compound 1 and PVP/VA;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 100 mg of substantially amorphous or amorphous Compound 1 and PVP/VA;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 150 mg of substantially amorphous or amorphous Compound 1 and PVP/VA;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 250 mg of substantially amorphous or amorphous Compound 1 and PVP/VA;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 25 mg of substantially amorphous or amorphous Compound 1 and HPMCAS;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 50 mg of substantially amorphous or amorphous Compound 1 and HPMCAS;
b. a filler;
c. a disintegrant;

d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 75 mg of substantially amorphous or amorphous Compound 1 and HPMCAS;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 100 mg of substantially amorphous or amorphous Compound 1 and HPMCAS;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 150 mg of substantially amorphous or amorphous Compound 1 and HPMCAS;
b. a filler;
c. a disintegrant;
d. a surfactant;
e. a binder;
f. a glidant; and
g. a lubricant.

In some embodiments, the present invention provides a method of administering a pharmaceutical composition comprising orally administering to a patient at least one tablet comprising:
a. a solid dispersion comprising about 250 mg of substantially amorphous or amorphous Compound 1 and HPMCAS;
b. a filler;
c. a disintegrant;
d. a surfactant;
e. a binder;
f. a glidant; and
g. a lubricant.

In some embodiments, the present invention provides for a method of orally administering the pharmaceutical composition described herein once a day. In other embodiments, the present invention provides for a method of orally administering the pharmaceutical composition described herein twice a day.

Another aspect of the present invention provides a method of administering a pharmaceutical composition by orally administering to a patient at least once per day at least one tablet comprising a solid dispersion of substantially amorphous or amorphous Compound 1, a filler, a binder, a glidant, a disintegrant, a surfactant, and a lubricant, in which the solid dispersion comprises at least about 25 mg of substantially amorphous or amorphous Compound 1. In some embodiments, the tablet is orally administered to the patient once per day. In another method, the administration comprises orally administering to a patient twice per day at least one tablet comprising a solid dispersion of substantially amorphous or amorphous Compound 1, a filler, a binder, a glidant, a disintegrant, a surfactant, and a lubricant, in which the solid dispersion contains at least about 25 mg of substantially amorphous or amorphous Compound 1. Some tablets useful in this method comprise a solid dispersion containing at least about 50 mg of substantially amorphous or amorphous Compound 1. In another method, the administration includes orally administering to a patient twice per day at least one tablet comprising a solid dispersion of substantially amorphous or amorphous Compound 1, a filler, a binder, a glidant, a disintegrant, a surfactant, and a lubricant, in which the solid dispersion contains at least about 50 mg of substantially amorphous or amorphous Compound 1. Some tablets useful in this method comprise a solid dispersion containing at least about 75 mg of substantially amorphous or amorphous Compound 1. In another method, the administration includes orally administering to a patient twice per day at least one tablet comprising a solid dispersion of substantially amorphous or amorphous Compound 1, a filler, a binder, a glidant, a disintegrant, a surfactant, and a lubricant, in which the solid dispersion contains at least about 75 mg of substantially amorphous or amorphous Compound 1. Another aspect of the present invention provides a method of administering a pharmaceutical composition by orally administering to a patient at least once per day at least one tablet comprising a solid dispersion of substantially amorphous or amorphous Compound 1, a filler, a binder, a glidant, a disintegrant, a surfactant, and a lubricant, in which the solid dispersion comprises at least about 100 mg of substantially amorphous or amorphous Compound 1. In some embodiments, the tablet is orally administered to the patient once per day. In another method, the administration comprises orally administering to a patient twice per day at least one tablet comprising a solid dispersion of substantially amorphous or amorphous Compound 1, a filler, a binder, a glidant, a disintegrant, a surfactant, and a lubricant, in which the solid dispersion contains at least about 100 mg of substantially amorphous or amorphous Compound 1. Other tablets useful in this method comprise a solid dispersion containing at least about 150 mg of substantially amorphous or amorphous Compound 1. In another method, the administration includes orally administering to a patient twice per day at least one tablet comprising a solid dispersion of substantially amorphous or amorphous Compound 1, a filler, a binder, a glidant, a disintegrant, a surfactant, and a lubricant, in which the solid dispersion contains at least about 150 mg of substantially amorphous or amorphous Compound 1. In another method, the administration includes orally administering to a patient at least once per day at least one tablet comprising a solid dispersion of substantially amorphous or amorphous Compound 1, a filler, a binder, a glidant, a disintegrant, a surfactant, and a lubricant, in which the solid dispersion contains at least about 250 mg of substantially amorphous or amorphous Compound 1. In another method, the administration includes orally administering to a patient once per day at least one tablet comprising a solid dispersion of substantially amorphous or amorphous Compound 1, a filler, a binder, a glidant, a disintegrant, a surfactant, and a lubricant, in which the solid dispersion contains at least about 250 mg of substantially amorphous or amorphous Compound 1. In another method, the administration includes orally administering to a patient twice per day at least one tablet comprising a solid dispersion of substantially amorphous or amorphous Compound 1, a filler, a binder, a glidant, a disintegrant, a surfactant, and a lubricant, in which the solid dispersion contains at least about 250 mg of substantially amorphous or amorphous Compound 1.

In one embodiment, the method of administering a pharmaceutical composition including orally administering to a patient at least once per day at least one tablet including a pharmaceutical composition containing a solid dispersion of amorphous Compound 1, a filler, a binder, a glidant, a disintegrant, a surfactant, and a lubricant, each of which is described above and in the Examples below, wherein the solid dispersion comprises at least 25 mg (e.g., at least 35 mg, at least 40 mg, or at least 45 mg) of substantially amorphous Compound 1.

In one embodiment, the method of administering a pharmaceutical composition includes orally administering to a patient at least once per day at least one tablet comprising a pharmaceutical composition containing a solid dispersion of substantially amorphous Compound 1, a filler, a binder, a glidant, a disintegrant, a surfactant, and a lubricant, wherein the solid dispersion comprises from about 30 mg to about 300 mg (e.g., from about 40 mg to about 280 mg or from about 45 mg to about 260 mg, or from about 50 mg to about 200 mg) of substantially amorphous Compound 1. Or, the method of administering a pharmaceutical composition includes orally administering to a patient at least once per day at least one tablet comprising a pharmaceutical composition containing a solid dispersion of amorphous Compound 1, a filler, a binder, a glidant, a disintegrant, a surfactant, and a lubricant, wherein the solid dispersion comprises from about 30 mg to about 300 mg (e.g., from about 40 mg to about 280 mg or from about 45 mg to about 260 mg, or from about 50 mg to about 200 mg) of amorphous Compound 1.

In another embodiment, the method of administering a pharmaceutical composition includes orally administering to a patient once per day at least one tablet comprising a pharmaceutical composition containing a solid dispersion of Compound 1, a filler, a binder, a glidant, a disintegrant, a surfactant, and a lubricant, each of which is described above and in the Examples below, wherein the solid dispersion comprises at least 25 mg (e.g., at least 35 mg, at least 40 mg, at least 45 mg, at least 75 mg, at least about 100 mg, at least about 150 mg, or at least 250 mg,) of substantially amorphous Compound 1 or amorphous Compound 1. For example, the method of administering a pharmaceutical composition includes orally administering to a patient once per day one tablet comprising a pharmaceutical composition containing a solid dispersion of Compound 1, a filler, a binder, a glidant, a disintegrant, a surfactant, and a lubricant, wherein the solid dispersion comprises at least 75 mg (e.g., at least 100 mg, at least 125 mg, at least 140 mg, at least 150 mg, or at least 250 mg) of substantially amorphous Compound 1 or amorphous Compound 1. In another example, the method of administering a pharmaceutical composition includes orally administering to a patient once per day a plurality of tablets (e.g., two tablets, three tablets, four or five tablets), wherein each tablet comprises a pharmaceutical composition comprising a solid dispersion of substantially amorphous Compound 1 or amorphous Compound 1, a filler, a binder, a glidant, a disintegrant, a surfactant, and a lubricant, wherein the solid dispersion comprises at least 25 mg (e.g., at least 35 mg, at least 40 mg, at least 45 mg, at least 75 mg, at least about 150 mg, or at least 250 mg,) of substantially amorphous Compound 1 or amorphous Compound 1.

In another embodiment, the method of administering a pharmaceutical composition includes orally administering to a patient twice per day at least one tablet comprising a pharmaceutical composition containing a solid dispersion of Compound 1, a filler, a binder, a glidant, a disintegrant, a surfactant, and a lubricant, each of which is described above and in the Examples below, wherein the solid dispersion comprises at least 25 mg (e.g., at least 35 mg, at least 40 mg, at least 45 mg, at least 50 mg, at least 75 mg, at least about 150 mg, or at least 250 mg,) of substantially amorphous Compound 1 or amorphous Compound 1. For example, the method of administering a pharmaceutical composition includes orally administering to a patient twice per day one tablet comprising a pharmaceutical composition containing a solid dispersion of Compound 1, a filler, a binder, a glidant, a disintegrant, a surfactant, and a lubricant, wherein the solid dispersion comprises at least 75 mg (e.g., at least 100 mg, at least 125 mg, at least 140 mg, at least 150 mg, or at least 250 mg) of substantially amorphous Compound 1 or amorphous Compound 1. In another example, the method of administering a pharmaceutical composition includes orally administering to a patient twice per day a plurality of tablets (e.g., two tablets, three tablets, four or five tablets), wherein each tablet comprises a pharmaceutical composition comprising a solid dispersion of substantially amorphous Compound 1 or amorphous Compound 1, a filler, a binder, a glidant, a disintegrant, a surfactant, and a lubricant, wherein the solid dispersion comprises at least 25 mg (e.g., at least 35 mg, at least 40 mg, at least 45 mg, at least 50 mg, at least 75 mg, at least about 150 mg, or at least 250 mg,) of substantially amorphous Compound 1 or amorphous Compound 1.

It is noted that the methods of administration of the present invention can optionally include orally administering a beverage (water, milk, or the like), food, and/or additional pharmaceutical compositions including additional APIs. When the method of administration includes orally administering a beverage (water, milk, or the like), food (including a standard high fat high calorie CF meal or snack), and/or additional pharmaceutical compositions including additional APIs, the oral administration of the beverage, food, and/or additional API can occur concurrently with the oral administration of the tablet, prior to the oral administration of the tablet, and/or after the administration of the tablet. For instance, in one example, the method of administering a pharmaceutical composition includes orally administering to a patient at least once per day at least one tablet comprising a pharmaceutical composition containing a solid dispersion of substantially amorphous Compound 1 or amorphous Compound 1, a filler, a binder, a glidant, a disintegrant, a surfactant, a lubricant, and a second API. In another example, the method of administering a pharmaceutical composition includes orally administering to a patient at least once per day at least one tablet comprising a pharmaceutical composition comprising a solid dispersion of substantially amorphous Compound 1 or amorphous Compound 1, a filler, a binder, a glidant, a disintegrant, a surfactant, and a lubricant, wherein the solid dispersion comprises at least 25 mg (e.g., at least 35 mg, at least 45 mg, or at least 50 mg) of substantially amorphous Compound 1 or amorphous Compound 1, and orally administering to a patient at least once per day a second pharmaceutical composition comprising a second API. In still other examples, the method of administering a pharmaceutical composition includes orally administering to a patient every 12 hours at least one tablet comprising a pharmaceutical composition as described herein, in which the tablet is administered about 30 minutes after consuming a high fat, high calorie CF meal or snack.

It will also be appreciated that the compound and pharmaceutically acceptable compositions of the present invention can be employed in combination therapies, that is, the compound and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, bronchodialator, an anti-biotic, an anti-infective agent, an anti-inflammatory agent, a CFTR modulator other than Compound 1 of the present invention, or a nutritional agent.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetras odium ([[(3S,5R)-5-(4-amino-2-oxopyrimidin-1-yl)-3-hydroxyoxolan-2-yl]methoxy-hydroxyphosphoryl][[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl) cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

VI. EXAMPLES

In order that the invention described herein may be more fully understood, the following examples are set forth. It should be understood that these examples are for illustrative purposes only and are not to be construed as limiting this invention in any manner.

A. Manufacture of Tablets

Intermediate A

A solvent system of methylethyl ketone (MEK) and DI water, formulated according to the ratio 90 wt % MEK/10 wt % DI water, was added to a reactor equipped with a magnetic stirrer and thermal circuit. Into this solvent system, hypromellose acetate succinate polymer (HG grade, commercially available from Biddle Sawyer Corporation in New York, N.Y. or Shin-Etsu Chemical Co. in Tokyo, Japan), sodium lauryl sulfate (SLS), and N-[2,4-bis(1,1-dimethylethyl)-5-hydroxyphenyl]-1,4-dihydro-4-oxoquinoline-3-carboxamide were added according to the ratio 49.5 wt % hypromellose acetate succinate/0.5 wt % sodium lauryl sulfate (SLS)/50 wt % N-[2,4-bis(1,1-dimethylethyl)-5-hydroxyphenyl]-1,4-dihydro-4-oxoquinoline-3-carboxamide. The resulting mixture contained 20 wt % dissolved solids. The actual amounts of ingredients and amounts of solvents used to generate this mixture are recited in Table A1, below:

TABLE A1

| Solid Spray Dispersion Ingredients for Intermediate A | | |
| --- | --- | --- |
|  | Units | Batch |
| N-[2,4-Bis(1,1-dimethylethyl)-5-hydroxyphenyl]-1,4-dihydro-4-oxoquinoline-3-carboxamide | Kg | 9.00 |
| hypromellose acetate succinate | Kg | 8.91 |
| SLS | Kg | 0.09 |
| Total Solids | Kg | 18.00 |
| MEK | Kg | 64.80 |
| Water | Kg | 7.20 |
| Total Solvents | Kg | 72.00 |
| Total Spray Solution Weight | Kg | 90.00 |

The mixture was mixed at room temperature until it was substantially homogenous and all components were substantially dissolved.

A spray drier, Niro Mobile Minor Spray Dryer with extended chamber, fitted with a 1.3 mm two-fluid atomizer situated approximately 5 cm from the top of the spray drying vessel was used in accordance with the spray dry parameters in Table A2.

TABLE A2

Dry spray process parameters used to generate Intermediate A.

| Parameter | Value |
|---|---|
| Atomization Flow Rate | 10.5 kg/hr |
| Feed Flow Rate | 7 kg/hr |
| Inlet Temperature | ~105° C. |
| Outlet Temperature | 40° C. ± 5° C. |
| Vacuum Dryer Temperature | 55° C. |
| Vacuum Drying Time | 24 hours |

An inertial cyclone separated the product from the process gas and solvent vapors, and a filter bag collected the fine particles not separated by the cyclone. The resultant product was transferred to a vacuum tray dryer for drying to reduce residual solvents to a level of less than about 5000 ppm and to generate dry Intermediate A.

Intermediate B

A solvent system of MEK, DI water, and acetone, formulated according to the ratio 65 wt % MEK/9 wt % DI water/26 wt % acetone, was heated to a temperature of 20-30° C. in a reactor equipped with a magnetic stirrer and thermal circuit. Into this solvent system, a copolymer of vinylpyrrolidone and vinyl acetatepolyvinylpyrrolidone (PVP VA-64 commercially available from Shanghai Lite Chemical Technology Co., Ltd. Shanghai, China), SLS, and N-[2,4-Bis(1,1-dimethylethyl)-5-hydroxyphenyl]-1,4-dihydro-4-oxoquinoline-3-carboxamide were added according to the ratio 19.5 wt % PVPVA-64/0.5 wt % sodium lauryl sulfate/80 wt % N-[2,4-Bis(1,1-dimethylethyl)-5-hydroxyphenyl]-1,4-dihydro-4-oxoquinoline-3-carboxamide. The resulting mixture contained 11.5 wt % solids. The actual amounts of ingredients and solvents used to generate this mixture are recited in Table B1, below:

TABLE B1

Solid Spray Dispersion Ingredients for Intermediate B

| | Units | Batch 1 |
|---|---|---|
| N-[2,4-Bis(1,1-dimethylethyl)-5-hydroxyphenyl]-1,4-dihydro-4-oxoquinoline-3-carboxamide | Kg | 24.00 |
| PVPVA-64 | Kg | 5.850 |
| SLS | Kg | 0.1500 |
| Total Solids | Kg | 30.00 |
| MEK | Kg | 150.1 |
| Water | Kg | 20.78 |
| Acetone | Kg | 60.03 |
| Total Solvents | Kg | 230.9 |
| Total Spray Solution Weight | Kg | 260.9 |

The mixture was maintained at a temperature of 20-30° C. and mixed until it was substantially homogenous and all components were substantially dissolved.

A spray drier, Niro Production Minor Spray Dryer, fitted with pressure nozzles (Spray Systems Maximum Passage series SK-MFP having orifice size 72), was used under normal spray drying mode, following the dry spray process parameters recited in Table B2, below. The spray nozzle was situated approximately 5 cm from the top of the spray drying vessel.

TABLE B2

Dry spray process parameters used to generate Intermediate B.

| Parameter | Value |
|---|---|
| Feed Pressure | 30-100 bar |
| Feed Flow Rate | 15-25 Kg/hr |
| Inlet Temperature | 85-125° C. |
| Outlet Temperature | 45-75° C. |
| Vacuum Dryer Temperature | 55° C. ± 5° C. |
| Vacuum Drying Time | 24 hours |

A high efficiency cyclone separated the wet product from the spray gas and solvent vapors. The wet product was transferred to a tray vacuum dryer for drying to reduce residual solvents to a level of less than about 5000 ppm and to generate dry Intermediate B.

Intermediate C:

A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and N-[2,4-Bis(1,1-dimethylethyl)-5-hydroxyphenyl]-1,4-dihydro-4-oxoquinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 12.5 wt % solids. The actual amounts of ingredients and solvents used to generate this mixture are recited in Table C1, below:

TABLE C1

Solid Spray Dispersion Ingredients for Intermediate C.

| | Units | Batch |
|---|---|---|
| N-[2,4-Bis(1,1-dimethylethyl)-5-hydroxyphenyl]-1,4-dihydro-4-oxoquinoline-3-carboxamide | Kg | 24.00 |
| HPMCAS | Kg | 5.850 |
| SLS | Kg | 0.1500 |
| Total Solids | Kg | 30.00 |
| MEK | Kg | 189.0 |
| Water | Kg | 21.00 |
| Total Solvents | Kg | 210.0 |
| Total Spray Solution Weight | Kg | 260.9 |

The mixture was maintained at a temperature of 20-30° C. and mixed until it was substantially homogenous and all components were substantially dissolved.

A spray drier, Niro Production Minor Spray Dryer, fitted with pressure nozzles (Spray Systems Maximum Passage series SK-MFP having orifice size 72), was used under normal spray drying mode, following the dry spray process parameters recited in Table C2, below. The spray nozzle was situated approximately 5 cm from the top of the spray drying vessel.

TABLE C2

Dry spray process parameters used to generate Intermediate C.

| Parameter | Target Value |
|---|---|
| Feed Pressure | 30-100 bar |
| Feed Flow Rate | 15-25 Kg/hr |
| Inlet Temperature | 85-125° C. |

TABLE C2-continued

Dry spray process parameters used to generate Intermediate C.

| Parameter | Target Value |
| --- | --- |
| Outlet Temperature | 45-75° C. |
| Vacuum Dryer Temperature | 55° C. (+/−5° C.) |
| Vacuum Drying Time | 24 hours |

A high efficiency cyclone separated the wet product from the spray gas and solvent vapors. The wet product was transferred to a tray vacuum dryer for drying to reduce residual solvents to a level of less than about 5000 ppm and to generate dry Intermediate C.

Intermediate D:

A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and N-[2,4-Bis(1,1-dimethylethyl)-5-hydroxyphenyl]-1,4-dihydro-4-oxo quinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 12.5 wt % solids. The actual amounts of ingredients and solvents used to generate this mixture are recited in Table D1, below:

TABLE D1

Solid Spray Dispersion Ingredients for Intermediate D.

| | Units | Batch |
| --- | --- | --- |
| N-[2,4-Bis(1,1-dimethylethyl)-5-hydroxyphenyl]-1,4-dihydro-4-oxoquinoline-3-carboxamide | Kg | 1.60 |
| HPMCAS | Kg | 0.390 |
| SLS | Kg | 0.010 |
| Total Solids | Kg | 2.00 |
| MEK | Kg | 12.6 |
| Water | Kg | 1.40 |
| Total Solvents | Kg | 14.0 |
| Total Spray Solution Weight | Kg | 16.0 |

The mixture was maintained at a temperature of 20-30° C. and mixed until it was substantially homogenous and all components were substantially dissolved.

A spray drier, Niro Mobil Minor Spray Dryer fitted with a 1.0 mm two fluid nozzle, was used in normal spray drying mode, following the dry spray process parameters recited in Table D2, below.

TABLE D2

Dry spray process parameters used to generate Intermediate D.

| Parameter | Value |
| --- | --- |
| Atomization Ratio | 1.5 |
| Feed Flow Rate | 4.5-5.0 Kg/hr |
| Outlet Temperature | 60° C. |
| Vacuum Dryer Temperature | 55° C. (+/−5° C.) |
| Vacuum Drying Time | 192 hours |

A high efficiency cyclone separated the wet product from the spray gas and solvent vapors. The wet product contained 6.3% MEK and 0.7% Water and had a mean particle size of 7 um and a bulk density of 0.23 g/cc. The wet product was transferred to a tray vacuum dryer for drying to reduce residual solvents to a level of less than about 5000 ppm and to generate dry Intermediate D. The dry Intermediate D contained <0.5% MEK and 0.3% Water.

Intermediate E:

A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and N-[2,4-Bis(1,1-dimethylethyl)-5-hydroxyphenyl]-1,4-dihydro-4-oxoquinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 10.5 wt % solids. The actual amounts of ingredients and solvents used to generate this mixture are recited in Table E1, below:

TABLE E1

Solid Spray Dispersion Ingredients for Intermediate E.

| | Units | Batch |
| --- | --- | --- |
| N-[2,4-Bis(1,1-dimethylethyl)-5-hydroxyphenyl]-1,4-dihydro-4-oxoquinoline-3-carboxamide | Kg | 43.93 |
| HPMCAS | Kg | 10.72 |
| SLS | Kg | 0.2750 |
| Total Solids | Kg | 54.93 |
| MEK | Kg | 421.8 |
| Water | Kg | 46.90 |
| Total Solvents | Kg | 468.7 |
| Total Spray Solution Weight | Kg | 523.6 |

The mixture temperature was adjusted to a range of 30-45° C. and mixed until it was substantially homogenous and all components were substantially dissolved.

A spray drier, Niro PSD4 Commercial Spray Dryer, fitted with pressure nozzles (Spray Systems Maximum Passage series SK-MFP having orifice/core size 54/21, 53/21 or 52/21) equipped with anti-bearding cap, was used under normal spray drying mode, following the dry spray process parameters recited in Table E2, below.

TABLE E2

Dry spray process parameters used to generate Intermediate E.

| Parameter | Value |
| --- | --- |
| Feed Pressure | 20-40 bar |
| Feed Flow Rate | 90-160 Kg/hr |
| Inlet Temperature | 75-125° C. |
| Outlet Temperature | 35-55° C. |
| Vacuum Dryer Temperature | 80° C. (+/−5° C.) |
| Vacuum Drying Time | 156 hours |

A high efficiency cyclone separated the wet product from the spray gas and solvent vapors. The wet product contained 8.8-12.5% wt. MEK/Water a mean particle size of 16-24 um and a bulk density of 0.28-0.36 g/cc. The wet product was transferred to a 350L stainless steel double cone vacuum dryer for drying to reduce residual solvents to a level of less than about 5000 ppm and to generate dry Intermediate E. The dry Intermediate E contained <0.3% MEK and 0.8% Water.

Intermediate F:

A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and N-[2,4-Bis(1,1-dimethylethyl)-5-hydroxyphenyl]-1,4-dihydro-4-oxoquinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 10.5 wt % solids. The actual amounts of ingredients and solvents used to generate this mixture are recited in Table F1, below:

TABLE F1

Solid Spray Dispersion Ingredients for Intermediate F.

|  | Units | Batch |
| --- | --- | --- |
| N-[2,4-Bis(1,1-dimethylethyl)-5-hydroxyphenyl]-1,4-diliydro-4-oxoquinoline-3-carboxamide | Kg | 70.0 |
| HPMCAS | Kg | 17.1 |
| SLS | Kg | 0.438 |
| Total Solids | Kg | 87.5 |
| MEK | Kg | 671 |
| Water | Kg | 74.6 |
| Total Solvents | Kg | 746 |
| Total Spray Solution Weight | Kg | 833 |

The mixture temperature was adjusted to a range of 20-45° C. and mixed until it was substantially homogenous and all components were substantially dissolved.

A spray drier, Niro PSD4 Commercial Spray Dryer, fitted with pressure nozzle (Spray Systems Maximum Passage series SK-MFP having orifice/core size 54/21) equipped with anti-bearding cap, was used under normal spray drying mode, following the dry spray process parameters recited in Table F2, below.

TABLE F2

Dry spray process parameters used to generate Intermediate F.

| Parameter | Value |
| --- | --- |
| Feed Pressure | 20 bar |
| Feed Flow Rate | 92-100 Kg/hr |
| Inlet Temperature | 93-99° C. |
| Outlet Temperature | 53-57° C. |
| Vacuum Dryer Temperature | 80° C. for 2 hours then 110° C. (+/−5° C.) |
| Vacuum Drying Time | 20-24 hours |

A high efficiency cyclone separated the wet product from the spray gas and solvent vapors. The wet product contained 8.5-9.7% MEK and 0.56-0.83% Water and had a mean particle size of 17-19 um and a bulk density of 0.27-0.33 g/cc. The wet product was transferred to a 4000L stainless steel double cone vacuum dryer for drying to reduce residual solvents to a level of less than about 5000 ppm and to generate dry Intermediate F. The dry Intermediate F contained <0.03% MEK and 0.3% Water.

Intermediate G:

A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and N-[2,4-Bis(1,1-dimethylethyl)-5-hydroxyphenyl]-1,4-dihydro-4-oxoquinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 10.5 wt % solids. The actual amounts of ingredients and solvents used to generate this mixture are recited in Table G1, below:

TABLE G1

Solid Spray Dispersion Ingredients for Intermediate G.

|  | Units | Batch |
| --- | --- | --- |
| N-[2,4-Bis(1,1-dimethylethyl)-5-hydroxyphenyl]-1,4-dihydro-4-oxoquinoline-3-carboxamide | Kg | 24.0 |
| HPMCAS | Kg | 5.85 |
| SLS | Kg | 0.15 |
| Total Solids | Kg | 30.0 |
| MEK | Kg | 230.1 |
| Water | Kg | 25.6 |
| Total Solvents | Kg | 255.7 |
| Total Spray Solution Weight | Kg | 285.7 |

The mixture temperature was adjusted to a range of 20-45° C. and mixed until it was substantially homogenous and all components were substantially dissolved.

A spray drier, Niro Production Minor Spray Dryer, fitted with pressure nozzle (Spray Systems Maximum Passage series SK-MFP having orifice size 72) was used under normal spray drying mode, following the dry spray process parameters recited in Table G2, below.

TABLE G2

Dry spray process parameters used to generate Intermediate G.

| Parameter | Value |
| --- | --- |
| Feed Pressure | 33 bar |
| Feed Flow Rate | 18-24 Kg/hr |
| Inlet Temperature | 82-84° C. |
| Outlet Temperature | 44-46° C. |
| Vacuum Dryer Temperature | 80° C. for 2 hours then 110° C. (+/−5° C.) |
| Vacuum Drying Time | 48 hours |

A high efficiency cyclone separated the wet product from the spray gas and solvent vapors. The wet product contained 10.8% MEK and 0.7% Water and had a mean particle size of 19 um and a bulk density of 0.32 g/cc. The wet product was transferred to a 4000L stainless steel double cone vacuum dryer for drying to reduce residual solvents to a level of less than about 5000 ppm and to generate dry Intermediate. The dry Intermediate G contained <0.05% MEK and 0.7% Water.

Example 1: Exemplary Tablet 1 (Formulated to have 25 mg of Compound 1)

A batch of round core ⅜" tablets was formulated to have approximately 25 mg of Compound 1 per tablet using the amounts of ingredients recited in Table 1, below.

TABLE 1

Ingredients for Exemplary Tablet 1.

| Tablet Formulation | Percent Dose % Wt./Wt. | Dose (mg) | Batch (g) |
|---|---|---|---|
| Intermediate A | 15.29% | 51.23 | 512.5 |
| Microcrystalline cellulose | 35.00% | 117.25 | 1172 |
| Lactose | 43.85% | 146.00 | 1460 |
| Sodium croscarmellose | 5.000% | 16.75 | 167.5 |
| SLS | 0.500% | 1.675 | 16.75 |
| Colloidal silicon dioxide | 0.125% | 0.4188 | 4.188 |
| Magnesium stearate | 0.50% | 1.675 | 16.75 |
| Total | 100% | 335 | 3350 |

Intermediate A, microcrystalline cellulose (FMC MCC Avicel® PH102, commercially available from FMC BioPolymer Corporation of Philadelphia, Pa.), lactose (Foremost FastFlo® Lactose #316 commercially available from Foremost Farms USA of Baraboo, Wis.), sodium croscarmellose (FMC Ac-Di-Sol®, commercially available from FMC BioPolymer Corporation of Philadelphia, Pa.), SLS, and colloidal silicon dioxide (Cabot Cab-O-Sil® M-5P Fumed Silicon Dioxide, commercially available from Cabot Corporation of Alpharetta, Ga.) were sieved through a 20 mesh screen to remove lumps.

Each of the sieved ingredients was added to a 16 quart V-blender in the following order:
1) lactose;
2) SLS;
3) sodium croscarmellose;
4) colloidal silicon dioxide;
5) Intermediate A; and
6) microcrystalline cellulose PH101

The mixture was blended for 25 minutes in a V-blender at 20-24 rpm. Magnesium stearate was sieved through a 30 mesh screen to remove lumps, and added to the mixture, which was blended for another 3 minutes.

Once the final blend has been completed, the mixture was transferred to a Piccola B-Tooling, 10 Station rotary tablet press (half tooled) for compression. Pressing the mixture into tablets generated ⅜" round tablets having approximately 25 mg of N-[2,4-Bis(1,1-dimethylethyl)-5-hydroxyphenyl]-1,4-dihydro-4-oxoquinoline-3-carboxamide.

Example 2: Exemplary Tablet 2 (Formulated to have 50 mg of Compound 1)

A batch of round core ⅜" tablets was formulated to have about 50 mg of Compound 1 per tablet using the amounts of ingredients recited in Table 2, below.

TABLE 2

Ingredients for Exemplary Tablet 2.

| Tablet Formulation | Percent Dose % Wt./Wt. | Dose (mg) | Batch (g) |
|---|---|---|---|
| Intermediate A | 30.60% | 102.50 | 1025.0 |
| Microcrystalline cellulose | 25.00% | 83.75 | 837.5 |
| Lactose | 38.28% | 128.23 | 1282.3 |
| Sodium croscarmellose | 5.000% | 16.75 | 167.5 |
| SLS | 0.500% | 1.675 | 16.75 |
| Colloidal silicon dioxide | 0.125% | 0.4188 | 4.188 |
| Magnesium stearate | 0.50% | 1.675 | 16.75 |
| Total | 100% | 335 | 3350 |

Intermediate A, microcrystalline cellulose, lactose, sodium croscarmellose, SLS, and colloidal silicon dioxide were sieved through a 20 mesh screen to remove lumps, and each of the sieved ingredients was added to a 16 quart V-blender in the following order:
1) lactose;
2) SLS;
3) sodium croscarmellose;
4) colloidal silicon dioxide;
5) Intermediate A; and
6) microcrystalline cellulose PH101

The mixture was blended for 25 minutes in a V-blender at 20-24 rpm. Magnesium stearate was sieved through a 30 mesh screen to remove lumps, and added to the mixture, which was blended for another 3 minutes.

Once the final blend has been completed, the mixture was transferred to a Piccola B-Tooling, 10 Station rotary tablet press (half tooled) for compression. Pressing the mixture into tablets generated ⅜" round tablets having approximately 50 mg of N-[2,4-Bis(1,1-dimethylethyl)-5-hydroxyphenyl]-1,4-dihydro-4-oxoquinoline-3-carboxamide.

Example 3: Exemplary Tablet 3 (Formulated with PVP/VA Polymer to have 150 mg of Compound 1)

A batch of caplet-shaped tablets was formulated to have about 150 mg of Compound 1 per tablet using the amounts of ingredients recited in Table 3, below.

TABLE 3

Ingredients for Exemplary Tablet 3.

| Tablet Formulation | Percent Dose % Wt./Wt. | Dose (mg) | Batch (g) |
|---|---|---|---|
| Intermediate B | 40.000% | 187.50 | 240.00 |
| Microcrystalline cellulose | 27.063% | 126.86 | 162.38 |
| Lactose | 27.063% | 126.86 | 162.38 |
| Sodium croscarmellose | 3.000% | 14.06 | 18.00 |
| SLS | 0.500% | 2.34 | 3.00 |
| Colloidal silicon dioxide | 1.000% | 4.69 | 6.00 |
| Coloring | 0.375% | 1.76 | 2.25 |
| Magnesium stearate | 1.000% | 4.69 | 6.00 |
| Total | 100% | 469 | 600 |

A glidant blend of colloidal silicon dioxide (Cabot Cab-O-Sil® M-5P Fumed Silicon Dioxide) and SLS was produced by hand mixing these two ingredients, in the amounts given in Table 3, and filtering the resulting mix through a 70 mesh screen sieve. A color blend of coloring (Colorcon Blue #1 Aluminum Lake #5516) and sodium croscarmellose (FMC Ac-Di-Sol®) was produced by hand mixing these two ingredients, in the amounts given in Table 3, and filtering the resulting mix through a 70 mesh screen sieve. The glidant blend and the color blend were hand mixed and added to a 2 L blending container. Intermediate B was added to this mixture in the 2 L blending container, and the contents 2 L blending container were hand mixed and filtered through a 30 mesh screen sieve. The resulting mixture was mixed on a Turbula mixer for 20 minutes at a rate of 22 rpm.

The microcrystalline cellulose (FMC MCC Avicel® PH102) and lactose (Foremost FastFlo® Lactose #316) were each filtered through a 30 mesh screen sieve and added to the blending container. The resulting mixture was mixed on a Turbula mixer for 20 minutes at a rate of 22 rpm.

Magnesium Stearate was filtered through a 70 mesh screen sieve and added to the mixture in the blending container, and the resulting mixture was mixed for 5 minutes at a rate of 22 rpm.

The resulting mixture was compressed into tablets using a gravity fed boot tooled with 0.64"×0.32" caplet type B tooling set to produce a tablet having an initial hardness of about 8 Kp±15%.

Example 4: Exemplary Tablet 4 (Formulated with HPMCAS Polymer to have 150 mg of Compound 1)

A batch of caplet-shaped tablets was formulated to have about 150 mg of Compound 1 per tablet using the amounts of ingredients recited in Table 4, below.

TABLE 4

Ingredients for Exemplary Tablet 4.

| Tablet Formulation | Percent Dose % Wt./Wt. | Dose (mg) | Batch (g) |
|---|---|---|---|
| Intermediate C | 34.091% | 187.50 | 204.55 |
| Microcrystalline cellulose | 30.017% | 165.09 | 180.10 |
| Lactose | 30.017% | 165.09 | 180.10 |
| Sodium croscarmellose | 3.000% | 16.50 | 18.00 |
| SLS | 0.500% | 2.75 | 3.00 |
| Colloidal silicon dioxide | 1.000% | 5.50 | 6.00 |
| Coloring | 0.375% | 2.06 | 2.25 |
| Magnesium stearate | 1.000% | 5.50 | 6.00 |
| Total | 100% | 550 | 600 |

A glidant blend of colloidal silicon dioxide (Cabot Cab-O-Sil® M-5P Fumed Silicon Dioxide) and SLS was produced by hand mixing these two ingredients, in the amounts given in Table 4, and filtering the resulting mix through a 70 mesh screen sieve. A color blend including coloring (Colorcon Blue #1 Aluminum Lake #5516) and sodium croscarmellose (FMC Ac-Di-Sol®) was produced by hand mixing these two ingredients, in the amounts given in Table 4, and filtering the resulting mix through a 70 mesh screen sieve. The glidant blend and the color blend were hand mixed and added to a 2 L blending container. Intermediate C was added to this mixture in the 2 L blending container, and the contents 2 L blending container were hand mixed and filtered through a 30 mesh screen sieve. The resulting mixture was mixed on a Turbula mixer for 20 minutes at a rate of 22 rpm.

The microcrystalline cellulose (FMC MCC Avicel® PH102) and lactose (Foremost FastFlo® Lactose #316) were each filtered through a 30 mesh screen sieve and added to the blending container. The resulting mixture was mixed on a Turbula mixer for 20 minutes at a rate of 22 rpm.

Magnesium stearate was filtered through a 70 mesh screen sieve and added to the mixture in the blending container, and the resulting mixture was mixed for 5 minutes at a rate of 22 rpm.

The resulting mixture was compressed into tablets using a tablet press tooled with 0.64"×0.32" caplet type B tooling set to produce a tablet having an initial hardness of about 9.5 Kp±15%.

Example 5: Exemplary Tablet 5 (Formulated with HPMCAS Polymer to have 150 mg of Compound 1)

A batch of caplet-shaped tablets was formulated to have about 150 mg of Compound 1 per tablet using the amounts of ingredients recited in Table 5, below.

TABLE 5

Ingredients for Exemplary Tablet 5.

| Tablet Formulation | Percent Dose % Wt./Wt. | Dose (mg) | Batch (g) |
|---|---|---|---|
| Intermediate G | 34.564% | 190.10 | 21000.00 |
| Microcrystalline cellulose | 29.968% | 164.82 | 18207.62 |
| Lactose | 29.968% | 164.82 | 18207.62 |
| Sodium croscarmellose | 3.000% | 16.50 | 1822.71 |
| SLS | 0.500% | 2.75 | 303.78 |
| Colloidal silicon dioxide | 1.000% | 5.50 | 607.57 |
| Magnesium stearate | 1.000% | 5.50 | 607.57 |
| Total | 100% | 550 | 607560 |

A blend of colloidal silicon dioxide (Cabot Cab-O-Sil® M-5P Fumed Silicon Dioxide), SLS, sodium croscarmellose (FMC Ac-Di-Sol®), and approximately 10% of the lactose (Foremost FastFlo® Lactose #316) given in Table 5 was produced by mixing these ingredients in a V-blender to provide about 125 inversions. This mixture, Preblend 1, was cone-milled through a 40 mesh screen sieve, collected and stored for subsequent use.

Approximately 20% of the lactose (Foremost FastFlo® Lactose #316) given in Table 5 was cone-milled through a 30 mesh screen sieve, collected and stored for subsequent use as Preblend 2. Intermediate G was filtered through a 30 mesh screen, collected and stored for subsequent use as Preblend 3. The microcrystalline cellulose (FMC MCC Avicel® PH102) was filtered through a 30 mesh screen, collected and stored for subsequent use as Preblend 4.

A V-blender was charged with Preblend 2, the remaining 70% of the lactose (Foremost FastFlo® Lactose #316) given in Table 3, Preblend 3, Preblend 1, and Preblend 4, in that order, and blended for about 500 inversions. The blended mixture was tested for uniformity.

Magnesium Stearate was filtered through a 70 mesh screen sieve and added to the mixture in the blending container, and the resulting mixture was mixed to provide about 125 inversions.

The resulting mixture was compressed into tablets using a Killian T100 press tooled with 0.64"×032" caplet type B tooling set to produce a tablet having an initial hardness of about 11 Kp±20%.

Example 6: Exemplary Tablet 6 (Formulated with HPMCAS Polymer to have 100 mg of Compound 1)

A batch of caplet-shaped tablets was formulated to have about 150 mg of Compound 1 per tablet using the amounts of ingredients recited in Table 6, below.

TABLE 6

Ingredients for Exemplary Tablet 6.

| Tablet Formulation | Percent Dose % Wt./Wt. | Dose (mg) | Batch (g) |
|---|---|---|---|
| Intermediate G | 34.564% | 126.73 | 9000.06 |
| Microcrystalline cellulose | 29.968% | 109.88 | 7803.32 |
| Lactose | 29.968% | 109.88 | 7803.32 |
| Sodium croscarmellose | 3.000% | 11.00 | 781.17 |
| SLS | 0.500% | 1.83 | 130.19 |

TABLE 6-continued

Ingredients for Exemplary Tablet 6.

| Tablet Formulation | Percent Dose % Wt./Wt. | Dose (mg) | Batch (g) |
|---|---|---|---|
| Colloidal silicon dioxide | 1.000% | 3.67 | 260.39 |
| Magnesium stearate | 1.000% | 3.67 | 260.39 |
| Total | 100% | 367 | 26040 |

A blend of colloidal silicon dioxide (Cabot Cab-O-Sil® M-5P Fumed Silicon Dioxide), SLS, sodium croscarmellose (FMC Ac-Di-Sol®), and approximately 10% of the lactose (Foremost FastFlo® Lactose #316) given in Table 6 was produced by mixing these ingredients in a V-blender to provide about 125 inversions. This mixture, Preblend 1, was cone-milled through a 40 mesh screen sieve, collected and stored for subsequent use.

Approximately 20% of the lactose (Foremost FastFlo® Lactose #316) given in Table 6 was cone-milled through a 30 mesh screen sieve, collected and stored for subsequent use as Preblend 2. Intermediate G was filtered through a 30 mesh screen, collected and stored for subsequent use as Preblend 3. The microcrystalline cellulose (FMC MCC Avicel® PH102) was filtered through a 30 mesh screen, collected and stored for subsequent use as Preblend 4.

A V-blender was charged with Preblend 2, the remaining 70% of the lactose (Foremost FastFlo® Lactose #316) given in Table 3, Preblend 3, Preblend 1, and Preblend 4, in that order, and blended for about 500 inversions. The blended mixture was tested for uniformity.

Magnesium Stearate was filtered through a 70 mesh screen sieve and added to the mixture in the blending container, and the resulting mixture was mixed to provide about 125 inversions.

The resulting mixture was compressed into tablets using a Killian T100 press tooled with 0.64"×0.32" caplet type B tooling set to produce a tablet having an initial hardness of about 11 Kp±20%.

Example 7: Exemplary Tablets 7 and 8 (Tablet 5 and 6 with Spray-Coating

A batch of caplet-shaped tablets from Example 5 and 6 was spray-coated with OPADRY® II (Blue, Colorcon) to a weight gain of about 3.0% using a 24" coating pan configured with the parameters in Table 7 followed by logo printing using Opacode® WB (Black, Colorcon).

TABLE 7

Spray-Coating Process Parameters

| Coating Parameters 24" Pan | Target |
|---|---|
| Pan Load (kg) | 15 |
| Inlet Temperature (° C.)* | * |
| Pan Speed (rpm) | 14 |
| Jog Time | TBD |
| # of Spray Guns | 2 |
| Solids Content (% w/w) | 20 |
| Gun to Bed Distance (inches) | 6 |
| Inlet Air How (cfm) | 250, 300** |
| Spray Rate (g/min) | 70 |
| Exhaust Temperature (° C.) | 50 |

TABLE 7-continued

Spray-Coating Process Parameters

| Coating Parameters 24" Pan | Target |
|---|---|
| Atomization Pressure (psi) | 25 |
| Pattern Pressure (psi) | 25 |

*Inlet temperature is monitored to achieve target exhaust temperature. Initial inlet temperature should be set at about 75° C. to achieve target exhaust temp.
**The target Inlet Air Flow was 250, 300 for Tablet 7 and Tablet 8, respectively.

The OPADRY® II suspension was prepared by measuring an amount of de-ionized water which when combined with OPADRY® II would produce a total solids content of 20% w/w. The water is mixed to a vortex followed by addition of OPADRY® II over a period of approximately 5 minutes. Once the OPADRY® II powder was wetted, mixing was continued to ensure that all solid material is well-dispersed. The suspension is then charged into a Thomas 24" pan coating instrument using coating conditions outlined in Table 7.

Core tablets are placed into the coating pan and prewarmed. The inlet temperature was increased from room temperature to about 55° C. and then increased as necessary to provide the exhaust temperature in Table 7. The coating process was performed with 20% w/w OPADRY® II (85 Series Blue) coating dispersion to obtain a target weight gain of about 3%. The coated tablets were then allowed to tumble for about 2 minutes without spraying. The bed temperature was then allowed to cool to about 35° C.

Once coated with OPADRY® II, the tablets are then labeled using a Hartnett Delta tablet printer charged with Opacode® WB.

Example 8: Exemplary Tablet 9 (Formulated with HPMCAS Polymer to have 100 mg of Compound 1)

A batch of caplet-shaped tablets was formulated to have about 100 mg of Compound 1 per tablet using the amounts of ingredients recited in Table 8, below.

TABLE 8

Ingredients for Exemplary Tablet 9.

| Tablet Formulation | Percent Dose % Wt./Wt. | Dose (mg) | Batch (g) |
|---|---|---|---|
| Intermediate F | 34.09% | 125.1 | 23.86 |
| Microcrystalline cellulose | 30.51% | 112.0 | 21.36 |
| Lactose | 30.40% | 111.6 | 21.28 |
| Sodium croscarmellose | 3.000% | 11.01 | 2.100 |
| SLS | 0.500% | 1.835 | 0.3500 |
| Colloidal silicon dioxide | 0.500% | 1.835 | 0.3500 |
| Magnesium stearate | 1.000% | 3.670 | 0.7000 |
| Total | 100% | 367 | 70 |

The colloidal silicon dioxide (Cabot Cab-O-Sil® M-5P Fumed Silicon Dioxide) and the microcrystalline cellulose (FMC MCC Avicel® PH102) were passed through a 30 mesh screen.

The sodium croscarmellose (FMC Ac-Di-Sol®), SLS, Intermediate F, and lactose (Foremost FastFlo® Lactose #316) were also passed, individually in the preceding order, through the same 30 mesh screen. A nitrogen purge was used when screening Intermediate F. The screened components were loaded into a 10 cubic feet V-blender, which was purged with nitrogen, and blended for about 180 (+/−10) inversions.

The Magnesium Stearate was filtered through a 40 mesh screen sieve into the blending container and mixed to provide about 54 inversions.

The resulting mixture was compressed into tablets using a fully tooled 36 Fette 2090 press with 0.568"×0.2885" caplet type B tooling set to produce a tablet having an initial target hardness of about 10 Kp±20%.

Example 9: Exemplary Tablet 10 (Tablet 9 with Spray-Coating)

A batch of caplet-shaped tablets from Example 8 was spray-coated with OPADRY® II (Blue, Colorcon) to a weight gain of about 3.0% using a 24" coating pan configured with the parameters in Table 9 followed by wax coating and then printing using Opacode® S-1-17823 (Solvent based Black, Colorcon).

TABLE 9

Spray-Coating Process Parameters

| Coating Parameters 24" Pan | Target |
|---|---|
| Pan Load (kg) | 14 |
| Inlet Temperature (° C.)* | * |
| Pan Speed (rpm) | 10 |
| Jog Time (sec) | |
| # of Spray Guns | 2 |
| Solids Content (% w/w) | 20 |
| Gun to Bed Distance (inches) | 6 |
| Inlet Air Flow (cfm) | 300 |
| Spray Rate (g/min) | 35 |
| Exhaust Temperature (° C.) | 50 |
| Atomization Pressure (psi) | 42 |

*Inlet temperature is monitored to achieve target exhaust temperature. Initial inlet temperature should be set at about 75° C. to achieve target exhaust temp.

The OPADRY® II suspension was prepared by measuring an amount of de-ionized water which when combined with OPADRY® II would produce a total solids content of 20% w/w. The water is mixed to a vortex followed by addition of OPADRY® II over a period of approximately 5 minutes. Once the OPADRY® II powder was wetted, mixing was continued to ensure that all solid material is well-dispersed. The suspension is then charged into a Thomas 24" pan coating instrument using coating conditions outlined in Table 9.

Uncoated tablets are placed into the coating pan and pre-warmed. The inlet was increased from room temperature to about 55° C. and then increased as necessary to provide the exhaust temperature in Table 9. The coating process was performed with 20% w/w OPADRY® II (85 Series Blue) coating dispersion to obtain a target weight gain of about 3%. The coated tablets were then allowed to tumble for about 2 minutes without spraying. The bed temperature was then allowed to cool to about 35° C.

Upon cooling, the Carnauba wax powder was weighed out in the amount of about 0.01% w/w of the starting tablet core weight. With the air flow off, the carnauba wax powder was sprinkled evenly on the tablet bed. The pan bed was turned on to the speed indicated in Table 9. After 5 minutes, the air flow was turned on (without heating) to the setting indicated in Table 9. After about one minute the air flow and pan were turned off.

Once coated with OPADRY® II, the tablets are then labeled using a Hartnett Delta tablet printer charged with Opacode® S-1-17823.

Example 10: Exemplary Tablet 11 (Formulated with HPMCAS Polymer to have 150 mg of Compound 1)

A batch of caplet-shaped tablets was formulated to have about 100 mg of Compound 1 per tablet using the amounts of ingredients recited in Table 11, below.

TABLE 10

Ingredients for Exemplary Tablet 11.

| Tablet Formulation | Percent Dose % Wt./Wt. | Dose (mg) | Batch (g) |
|---|---|---|---|
| Intermediate F | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

The colloidal silicon dioxide (Cabot Cab-O-Sil® M-5P Fumed Silicon Dioxide) and the microcrystalline cellulose (FMC MCC Avicel® PH102) were passed through a 30 mesh screen.

The sodium croscarmellose (FMC Ac-Di-Sol®), SLS, Intermediate F, and lactose (Foremost FastFlo® Lactose #316) were also passed, individually in the preceding order, through the same 30 mesh screen. A nitrogen purge was used when screening Intermediate F. The screened components were loaded into a 10 cubic feet V-blender, which was purged with nitrogen, and blended for about 180 (+/−10) inversions.

The Magnesium Stearate was filtered through a 40 mesh screen sieve into the blending container and mixed to provide about 54 inversions.

The resulting mixture was compressed into tablets using a fully tooled 36 Fette 2090 press with 0.568"×0.2885" caplet type B tooling set to produce a tablet having an initial target hardness of about 10 Kp±20%.

Example 11: Exemplary Tablet 12 (Tablet 11 with Spray-Coating)

A batch of caplet-shaped tablets from Example 10 was spray-coated with OPADRY® II (Blue, Colorcon) to a weight gain of about 3.0% using a 24" coating pan configured with the parameters in Table 11 followed by wax coating and then printing using Opacode® S-1-17823 (Solvent based Black, Colorcon).

TABLE 11

Spray-Coating Process Parameters

| Coating Parameters 24" Pan | Target |
|---|---|
| Pan Load (kg) | 14 |
| Inlet Temperature (° C.)* | * |
| Pan Speed (rpm) | 10 |
| Jog Time (sec) | 2-5 sec every 60 sec |
| # of Spray Guns | 2 |
| Solids Content (% w/w) | 20 |
| Gun to Bed Distance (inches) | 6 |
| Inlet Air Flow (cfm) | 300 |
| Spray Rate (g/min) | 35 |

TABLE 11-continued

Spray-Coating Process Parameters

| Coating Parameters 24" Pan | Target |
|---|---|
| Exhaust Temperature (° C.) | 50 |
| Atomization Pressure (psi) | 42 |

*Inlet temperature is monitored to achieve target exhaust temperature. Initial inlet temperature should be set at about 75° C. to achieve target exhaust temp.

The OPADRY® II suspension was prepared by measuring an amount of de-ionized water which when combined with OPADRY® II would produce a total solids content of 20% w/w. The water is mixed to a vortex followed by addition of OPADRY® II over a period of approximately 5 minutes. Once the OPADRY® II powder was wetted, mixing was continued to ensure that all solid material is well-dispersed. The suspension is then charged into a Thomas 24" pan coating instrument using coating conditions outlined in Table 11.

Uncoated tablets are placed into the coating pan and pre-warmed. The inlet was increased from room temperature to about 55° C. and then increased as necessary to provide the exhaust temperature in Table 9. The coating process was performed with 20% w/w OPADRY® II (85 Series Blue) coating dispersion to obtain a target weight gain of about 3%. The coated tablets were then allowed to tumble for about 2 minutes without spraying. The bed temperature was then allowed to cool to about 35° C.

Upon cooling, the Carnauba wax powder was weighed out in the amount of about 0.01% w/w of the starting tablet core weight. With the air flow off, the carnauba wax powder was sprinkled evenly on the tablet bed. The pan bed was turned on to the speed indicated in Table 11. After 5 minutes, the air flow was turned on (without heating) to the setting indicated in Table 11. After about one minute the air flow and pan were turned off.

Once coated with OPADRY® II, the tablets are then labeled using a Hartnett Delta tablet printer charged with Opacode® S-1-17823.

B. Administration of Pharmaceutical Formulations

Example 12: Exemplary Administration A

Human patients are orally administered a pharmaceutical formulation according to Table 12:

TABLE 12

Exemplary administration A of pharmaceutical formulations of the present invention.

| Frequency of dosing (per day) | Tablet Description | Conditions |
|---|---|---|
| One administration | 3 × 50 mg Tablets of Example 2 | Administered with 240 mL of water under fasting conditions |
| One administration | 150 mg Tablet of Example 3 | Administered with 240 mL of water under fasting conditions |
| One administration | 150 mg Tablet of Example 3 | Administered with 240 mL of water, 30 minutes after start of a high fat breakfast |
| One administration | 150 mg Tablet of Example 4 | Administered with 240 mL of water under fasting conditions |
| One administration | 150 mg Tablet of Example 4 | Administered with 240 mL of water, 30 minutes after start of a high fat breakfast |

The pharmaceutical formulations are administered to subjects between 7:00 AM and 9:00 AM, and the pharmaceutical formulation is given at approximately the same time (within a 1-hour window) on each dosing occasion. For administrations that occur under patient fasting, food is allowed 4 hours after the pharmaceutical formulation is administered. For administrations that permit feeding, breakfast is given about 30 minutes prior to the dosing time and is consumed in about 25 minutes. In each of these administrations, the patient is instructed not to lie down for 4 hours after taking the study drug.

Example 13: Exemplary Administration B

Human patients are orally administered a pharmaceutical formulation according to Table 13:

TABLE 13

Exemplary administration B of pharmaceutical formulations of the present invention.

| Frequency of dosing | Dosage |
|---|---|
| 12 hr. intervals | 25 mg Tablet of Example 1 |
| 12 hr. intervals | 1 × 25 mg Tablet of Example 1, and 1 × 50 mg Tablet of Example 2 |
| 12 hr. intervals | 3 × 50 mg Tablet of Example 2 |
| 12 hr. intervals | 5 × 50 mg Tablet of Example 2 |
| 12 hr. intervals | 150 mg Tablet of Example 5 |
| 12 hr. intervals | 100 mg Tablet of Example 6 |

The pharmaceutical formulations are administered to patients approximately every 12 hours.

Example 14: Dissolution Profile of Several Exemplary Tablets

Referring to FIG. 1, the dissolution profiles of several exemplary tablets are graphically illustrated. It is noted that each of the exemplary tablets illustrated in FIG. 1 are at least 50% dissolved at about 30 minutes.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A pharmaceutical composition comprising a solid dispersion, wherein the solid dispersion comprises:

a) 80% of amorphous or substantially amorphous N-[2,4-Bis(1,1-dimethylethyl)-5-hydroxyphenyl]-1,4-dihydro-4-oxoquinoline-3-carboxamide (Compound 1) by weight of the dispersion, wherein substantially amorphous Compound 1 comprises less than 15% crystalline Compound 1, b) 19.5% of hydroxypropylmethylcellulose acetate succinate (HPMCAS) by weight of the dispersion, and c) 0.5% of sodium lauryl sulfate (SLS) by weight of the dispersion.

2. The pharmaceutical composition of claim 1, wherein the composition further comprises 30.5% of microcrystalline cellulose by weight of the composition.

3. The pharmaceutical composition of claim 1, wherein the composition further comprises 30.4% of lactose by weight of the composition.

4. The pharmaceutical composition of claim 1, wherein the composition further comprises 3% of sodium croscarmellose by weight of the composition.

5. The pharmaceutical composition of claim 1, wherein the composition further comprises 0.5% of SLS by weight of the composition.

6. The pharmaceutical composition of claim 1, wherein the composition further comprises 0.5% of colloidal silicon dioxide by weight of the composition.

7. The pharmaceutical composition of claim 1, wherein the composition further comprises 1.0% of magnesium stearate by weight of the composition.

8. The pharmaceutical composition of claim 1, wherein the composition further comprises a coating.

9. The pharmaceutical composition of claim 1, wherein the composition has a hardness of 98 N (10 kp)±20 percent.

10. The pharmaceutical composition of claim 1, wherein the composition contains 150 mg of Compound 1.

11. The pharmaceutical composition of claim 1, wherein the composition contains 100 mg of Compound 1.

12. The pharmaceutical composition of claim 1, comprising 34.1% of the solid dispersion by weight of the composition.

13. The pharmaceutical composition of claim 1, wherein substantially amorphous Compound 1 comprises less than 5% crystalline Compound 1.

14. A pharmaceutical table comprising:
a. a solid dispersion in an amount ranging from 30% to 50% by weight of the tablet, wherein the dispersion comprises:
  i) 80% of amorphous or substantially amorphous N-[2,4-Bis(1,1-dimethylethyl)-5-hydroxyphenyl]-1,4-dihydro-4-oxoquinoline-3-carboxamide (Compound 1) by weight of the dispersion, wherein substantially amorphous Compound 1 comprises less than 15% crystalline Compound 1,
  ii) 19.5% of hydroxypropylmethyl cellulose acetate succinate (HPMCAS) by weight of the dispersion, and
  iii) 0.5% of sodium lauryl sulfate (SLS) by weight of the dispersion;
b. a filler, in an amount ranging from 25% to 50% by weight of the tablet;
c. a disintegrant, in an amount ranging from 1% to 10% by weight of the tablet;
d. a surfactant, in an amount ranging from 0.3% to 2% by weight of the tablet;
e. a binder, in an amount ranging from 20% to 45% by weight of the tablet;
f. a glidant, in an amount ranging from 0.09% to 1.0% by weight of the tablet; and
g. a lubricant, in an amount ranging from 0.1% to 2% by weight of the tablet.

15. The pharmaceutical tablet of claim 14, wherein substantially amorphous Compound 1 comprises less than 5% crystalline Compound 1.

16. The pharmaceutical composition of claim 1, comprising:
a. 34.1 wt % of a solid dispersion comprising:
  i) 80% of amorphous or substantially amorphous Compound 1 by weight of the dispersion, wherein substantially amorphous Compound 1 comprises less than 15% crystalline Compound 1,
  ii) 19.5% of HPMCAS by weight of the dispersion, and
  iii) 0.5% of SLS by weight of the dispersion;
b. 30.5% of microcrystalline cellulose by weight of the composition;
c. 30.4% of lactose by weight of the composition;
d. 3% of sodium croscarmellose by weight of the composition;
e. 0.5% of SLS by weight of the composition;
f. 0.5% of colloidal silicon dioxide by weight of the composition; and
g. 1.0% of magnesium stearate by weight of the composition.

17. The pharmaceutical composition of claim 16, wherein substantially amorphous Compound 1 comprises less than 5% crystalline Compound 1.

18. The pharmaceutical composition of claim 1, wherein the pharmaceutical composition is formulated as a tablet.

19. The tablet of claim 18, wherein the tablet further comprises 30.5% of microcrystalline cellulose by weight of the tablet.

20. The tablet of claim 18, wherein the tablet further comprises 30.4% of lactose by weight of the tablet.

21. The tablet of claim 18, wherein the tablet further comprises 3% of sodium croscarmellose by weight of the tablet.

22. The tablet of claim 18, wherein the tablet further comprises 0.5% of SLS by weight of the tablet.

23. The tablet of claim 18, wherein the tablet further comprises 0.5% of colloidal silicon dioxide by weight of the tablet.

24. The tablet of claim 18, wherein the tablet further comprises 1.0% of magnesium stearate by weight of the tablet.

25. The tablet of claim 18, comprising 34.1% of the solid dispersion by weight of the tablet.

26. The tablet of claim 18, comprising:
a. 34.1 wt % of a solid dispersion comprising:
  i) 80% of amorphous or substantially amorphous Compound 1 by weight of the dispersion, wherein substantially amorphous Compound 1 comprises less than 15% crystalline Compound 1,
  ii) 19.5% of HPMCAS by weight of the dispersion, and
  iii) 0.5% of SLS by weight of the dispersion;
b. 30.5% of microcrystalline cellulose by weight of the tablet;
c. 30.4% of lactose by weight of the tablet;
d. 3% of sodium croscarmellose by weight of the tablet;
e. 0.5% of SLS by weight of the tablet;
f. 0.5% of colloidal silicon dioxide by weight of the tablet; and
g. 1.0% of magnesium stearate by weight of the tablet.

* * * * *

UNITED STATES PATENT AND TRADEMARK OFFICE
CERTIFICATE OF CORRECTION

PATENT NO. : 10,646,481 B2
APPLICATION NO. : 15/253636
DATED : May 12, 2020
INVENTOR(S) : William Rowe et al.

Page 1 of 1

It is certified that error appears in the above-identified patent and that said Letters Patent is hereby corrected as shown below:

In the Claims

Claim 14, Column 63, Line 43, "table" should read --tablet--.

Claim 14, Column 63, Line 53, "hydroxypropylmethyl cellulose" should read --hydroxypropylmethylcellulose--.

Signed and Sealed this
Fourteenth Day of July, 2020

Andrei Iancu
*Director of the United States Patent and Trademark Office*